(12) United States Patent
Hickman et al.

(10) Patent No.: US 9,289,488 B2
(45) Date of Patent: Mar. 22, 2016

(54) VACCINE ENGINEERING

(75) Inventors: David Hickman, Saint-Sulpice (CH); Maria Pilar Lopez-Deber, Lausanne (CH); Andreas Muhs, Cugy (CH)

(73) Assignee: AC Immune SA, Lausanne (CH)

( * ) Notice: Subject to any disclaimer, the term of this patent is extended or adjusted under 35 U.S.C. 154(b) by 385 days.

(21) Appl. No.: 13/816,461

(22) PCT Filed: Aug. 12, 2011

(86) PCT No.: PCT/EP2011/063933
§ 371 (c)(1),
(2), (4) Date: Feb. 11, 2013

(87) PCT Pub. No.: WO2012/020124
PCT Pub. Date: Feb. 16, 2012

(65) Prior Publication Data
US 2013/0287838 A1    Oct. 31, 2013

(30) Foreign Application Priority Data
Aug. 12, 2010 (EP) .................................. 10172619

(51) Int. Cl.
*A61K 39/385* (2006.01)
*A61K 39/00* (2006.01)
*C07K 16/18* (2006.01)

(52) U.S. Cl.
CPC ........... *A61K 39/385* (2013.01); *A61K 39/0007* (2013.01); *C07K 16/18* (2013.01); *A61K 2039/55555* (2013.01); *A61K 2039/6018* (2013.01); *A61K 2039/64* (2013.01); *G01N 2405/00* (2013.01); *G01N 2440/10* (2013.01)

(58) Field of Classification Search
None
See application file for complete search history.

(56) References Cited

U.S. PATENT DOCUMENTS

| | | | |
|---|---|---|---|
| 4,565,696 A | 1/1986 | Heath et al. | |
| 5,540,935 A | 7/1996 | Miyazaki et al. | |
| 5,672,662 A | 9/1997 | Harris et al. | |
| 5,721,106 A | 2/1998 | Maggio et al. | |
| 5,885,613 A | 3/1999 | Holland et al. | |
| 6,169,166 B1 | 1/2001 | Brun et al. | |
| 6,521,211 B1 | 2/2003 | Unger et al. | |
| 6,521,635 B1 | 2/2003 | Bates et al. | |
| 7,378,469 B2 | 5/2008 | Kozlowski | |
| 7,807,175 B2 * | 10/2010 | Pfeifer et al. | 424/194.1 |
| 2002/0025312 A1 | 2/2002 | Tagawa et al. | |
| 2003/0108551 A1 | 6/2003 | Nicolau et al. | |
| 2004/0180002 A1 | 9/2004 | Young et al. | |
| 2004/0242845 A1 | 12/2004 | Nicolau et al. | |
| 2004/0248799 A1 | 12/2004 | Holaday et al. | |
| 2007/0032408 A1 | 2/2007 | Holmes et al. | |
| 2008/0233181 A1 | 9/2008 | Nagy et al. | |

FOREIGN PATENT DOCUMENTS

| | | |
|---|---|---|
| AU | 2004/262472 A1 | 2/2005 |
| EP | 0203676 A2 | 12/1986 |
| EP | 1 270 592 B1 | 9/2004 |
| JP | 7-291853 | 11/1995 |
| JP | 8-501925 | 3/1996 |
| JP | 11-152234 | 6/1998 |
| JP | 2002-500165 A1 | 7/1999 |
| JP | 2003-518151 | 6/2001 |
| JP | 2002-047298 A | 2/2002 |
| WO | WO 93/25700 A1 | 12/1993 |
| WO | WO 94/10198 A1 | 5/1994 |
| WO | WO 96/25435 A1 | 8/1996 |
| WO | WO 98/46636 A2 | 10/1998 |
| WO | WO 99/27944 A1 | 6/1999 |
| WO | 99/41279 A2 | 8/1999 |
| WO | WO 99/41279 A2 | 8/1999 |
| WO | WO 99/42130 A1 | 8/1999 |
| WO | WO 00/72876 A2 | 12/2000 |
| WO | WO 00/72880 A2 | 12/2000 |
| WO | WO 01/18169 A2 | 3/2001 |
| WO | WO 01/62284 A2 | 8/2001 |
| WO | WO 02/09748 A1 | 2/2002 |
| WO | WO 02/21141 A2 | 3/2002 |
| WO | WO 02/074243 A3 | 9/2002 |
| WO | 03/000719 A2 | 1/2003 |
| WO | WO 03/015812 A2 | 2/2003 |
| WO | WO 03/039467 A2 | 5/2003 |
| WO | WO 2004/013172 A2 | 2/2004 |
| WO | WO 2004/069182 A2 | 8/2004 |
| WO | WO 2005/081872 A2 | 9/2005 |
| WO | WO 2006/066003 A2 | 6/2006 |
| WO | WO 2007/068411 A2 | 6/2007 |
| WO | WO 2007/068412 A2 | 6/2007 |
| WO | WO 2010/115843 A2 | 10/2010 |

OTHER PUBLICATIONS

JP Office Action issued in Appl. No: 2006-554250, pp. 1-4, Dec. 15, 2010.
Japanese Office Action issued in JP Application No. 2006-554250, JP Office Action, pp. 1-10, Sep. 21, 2011.
Amyloid, Wikipedia—http://en.wikipedia.org/wiki/Amyloid, pp. 1-6, Sep. 21, 2009.
Definition of Amyloid, MedicineNet.com, pp. 1, Aug. 4, 2009.
Pegasys as Treatment for People with Hepatitis B, Website—Medical Brochure information, pp. 1-2, May 16, 2007.
Japanese Office Action—Application No. 2011-131772 (with English translation), pp. 1-6, Feb. 21, 2013.
Chinese Office Action—Application No. 2005-800125877, pp. 1-2, Jan. 20, 2012.

(Continued)

*Primary Examiner* — Yunsoo Kim
(74) *Attorney, Agent, or Firm* — F. Brent Nix, Esq.; Johnson, Marcou & Isaacs, LLC

(57) ABSTRACT

The method and constructs disclosed and claimed herein allow to control peptide conformation by modulation of the peptide lipidation pattern, spacer and liposome composition, or via co-administration with small molecules. Accordingly, this technology can be applied to the rational design of liposomal vaccines and for the generation of safer and more efficacious therapies for a range of human disease, in particular those based on misfolded proteins.

18 Claims, 9 Drawing Sheets

(56) References Cited

OTHER PUBLICATIONS

Figure 1:
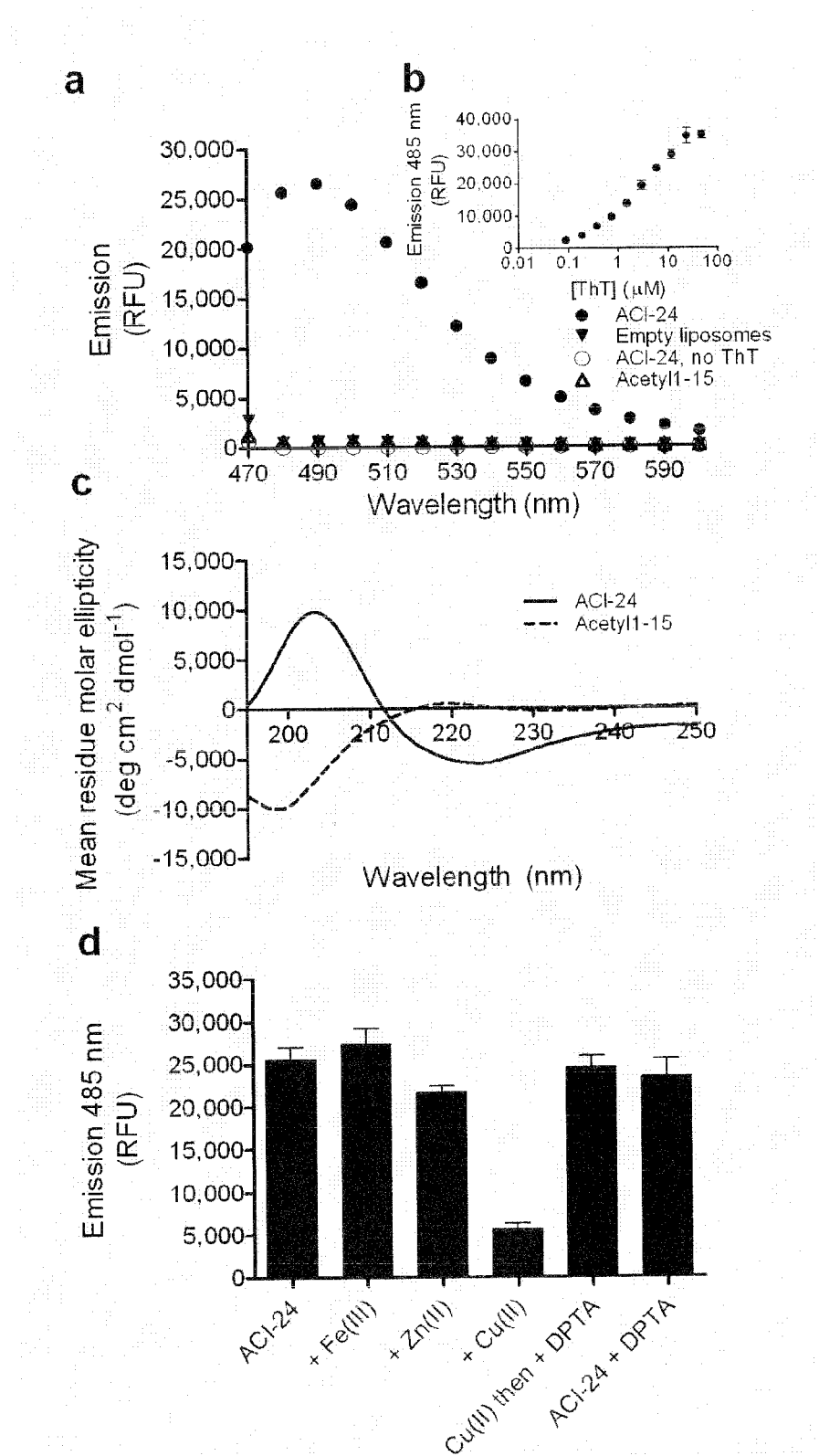

Sigma-Aldrich—FLUKA AG—Cat. No. 79898—O-[2-(boc-amino)-ethyl]-O'[2-(diglycolyl-amino)ethyl]decaehtylene glycol, *FLUKA AG*, pp. 1, Jan. 1, 2002.

Abuchowski, Alteration of Immunological Properties of Bovine Serum Albumin by Covalent Attachment of Polyethylene Glycol, *The Journal of Biological Chemistry*, vol. 252 (11), pp. 3578-3581, Jan. 1, 1977.

Abuchowski et al., Effect of Covalent Attachment of Polyethylene Glycol on Immunogenicity and Circulating Life of Bovine Liver Catalase, *The Journal of Biological Chemistry*, vol. 252 (11), pp. 3582-3586, Jan. 1, 1977.

Allen et al., Liposomes Containing Synthetic Lipid Derivatives of Poly(ehtylene glycol) Show Prolonged Circulation Half-lives in Vivo (Applicants only have Abstract), *Biochim Biophys Acta*, vol. 1066(1), pp. 29-36, Jul. 1, 1991.

Barret et al., Evaluation of Quinacrine Treatment for Prion Diseases, *Journal of Virology*, vol. 77 (13), pp. 8462-8469, Jan. 1, 2003.

Bashir et al., Generation of a Monoclonal Antibody to P-Glycoprotein Peptides using Tuberculin-PPD as a Carrier, *Virchows Arch.*, vol. 432, pp. 279-287, Jan. 1, 1998.

Candido et al., Local Administration of Dendritic Cells Inhibits Established Breast Tumor Growth: Implications for Apoptosis-Inducing Agents, *Cancer Research*, vol. 61, pp. 228-236, Jan. 1, 2001.

Chen et al., Internal Duplication and Homology with Bacterial Transport Proteins in the mdrl (P-Glycoprotein) Gene from Multidrug-Resistant Human Cells, *Cell*, vol. 47, pp. 381-389, Jan. 1, 1986.

De Gioia et al., Conformational Polymorphism of the Amyloidogenic and Neurotoxic Peptide Homologous to Residues 106-126 of the Prior Protein, *The Journal of Biological Chemistry*, vol. 269 (11), pp. 7859-7862, Mar. 18, 1994.

Deprez et al., Comparative Efficiency of Simple Lipoprotein Constructs for in vivo Induction of Virus-Specific CTL, *Vaccine*, vol. 14 (5), pp. 375-382, Jan. 1, 1998.

Endicott et al., The Biochemistry of P-Glycoprotein-Mediated Multidrug Resistance, *Annual Reviews Biochemistry*, vol. 58, pp. 137-171, Jan. 1, 1989.

Felix, Arthur, Site-Specific Poly(ethylene glycol)ylation of Peptides, *American Chemical Society—ACS Symposium Seminar*, vol. 680, pp. 218-238, Jan. 1, 1997.

Fleiner et al., Studies on Protein-Liposome Coupling Using Novel Thiol-Reactive Coupling Lipids: Influence of Spacer Length and Polarity, *Bioconjugate Chemistry*, vol. 12, pp. 470-475, Jan. 1, 2001.

Fries et al., Liposomal of Malaria Vaccine in Humans: A Safe and Potent Adjuvant Strategy, *Proceedings of the National Academy of Science USA*, vol. 89, pp. 358-362, Jan. 1, 1992.

Fukuda et al., Synthesis, Aggregation, and Neurotoxicity of the Alzheimer's Aβ1-42 Amyloid Peptide and Its Isoaspartyl Isomers, *Bioorganic and Medicinal Chemistry*, vol. 9, pp. 953-956, Jan. 1, 1999.

Gaertner et al., Site-Specific Attachment of Functionalized Poly(ethylene glycol) to the Amino Terminis of Proteins, *Bioconjugate Chemistry*, vol. 7, pp. 38-44, Jan. 1, 1996.

Gatouillat et al., Immunization with Lipsome-Anchored Pegylated Peptides Modulates Doxorubicin Sensitivity in P-Glycoprotein-Expressing P388 Cells, *Science Direct—Cancer Letters*, vol. 257, pp. 165-171, Jan. 1, 2007.

Goldsby et al., Immunology—Chapter 19 Vaccines, *Immunology—Fourth Edition*, pp. 449-465, Jan. 1, 2002.

Grace et al., Site of Pegylation and Polyethylene Glycol Molecule Size Attenuate Interferon-a Antiviral and Antiproliferative Activities through the JAK/STAT Signaling Pathway, *The Journal of Biological Chemistry*, vol. 280 (8), pp. 6327-6337, Jan. 1, 2005.

Gura, Systems for Identifying New Drugs Often Faulty, *Science*, vol. 278, pp. 1041-1042, Nov. 7, 1997.

Janssen et al., Peptide-targeted PEG-liposomes in Anti-angiogenic Therapy, *International Journal of Pharmaceutics*, vol. 254, pp. 55-58, Jan. 1, 2003.

Juliano et al., A Surface Glycoprotein Modulating Drug Permeability in Chinese Hamster Ovary Cell Mutants, *Biochmica et Biophysica Acta*, vol. 455, pp. 152-162, Jan. 1, 1976.

Kaiser, J., First Pass at Cancer Genome Reveals Complex Landscape, *Science*, vol. 313, pp. 1370, Sep. 8, 2006.

Kim, Y., Office Action issued in copending U.S. Appl. No. 10/958,211, filed Oct. 4, 2004, pp. 1-8, Dec. 18, 2009.

Kim, Y., Office Action issued in copending U.S. Appl. No. 10/958,211, filed Oct. 4, 2004, pp. 1-6, Nov. 29, 2007.

Kim, Y., Office Action issued in copending U.S. Appl. No. 10/958,211, filed Oct. 4, 2004, pp. 1-8, Oct. 29, 2010.

Kim, Y., Office Action issued in copending U.S. Appl. No. 10/958,211, filed Oct. 4, 2004, pp. 1-12, Sep. 8, 2008.

Kim, Y., Office Action issued in copending U.S. Appl. No. 10/958,211, filed Oct. 4, 2004, pp. 1-8, Jul. 16, 2010.

Kim, Y., Office Action issued in copending U.S. Appl. No. 10/958,211, filed Oct. 4, 2004, pp. 1-12, Jun. 4, 2007.

Kim, Y., Office Action issued in copending U.S. Appl. No. 10/958,211, filed Oct. 4, 2004, pp. 1-12, May 8, 2009.

Kim, Y., International Search Report and Written Opinion—Appl. No: PCT/US05/05285, pp. 1-16, May 2, 2007.

Kim, Y., Office Action issued in copending U.S. Appl. No. 10/958,211, filed Oct. 4, 2004, pp. 1-10, Apr. 13, 2011.

Office Action issued in U.S. Appl. No. 10/958,211, *USPTO Office Action*, pp. 1-11, Jul. 16, 2010.

Klohs et al., Resistance to Anthrapyrazoles and Anthracyclines in Multidrug-Resistant P388 Murine Leukemia Cells: Reversal by Calcium Blockers and Calmodulin Antagonists, *Cancer Research*, vol. 46, pp. 4352-4356, Sep. 1, 1986.

Kodera et al., "Proteins, Nucleic Acids and Enzymes"—Article cited in JP Office Action of Appl No. 2006-554250—(for statement of relevance see English translation of Office Action attached hereto), *Tanpakushitsu Kakusan Koso (PNAS)*, vol. 48 (11), pp. 1527-1533, Aug. 10, 2003.

Kodera et al., Proteins, Nucleic Acids and Enzymes (English abstract), vol. 48 (11), pp. 1527-1533, Jan. 1, 2003.

Marincola et al., Tumors as Elusive Targets of T-Cell-Based Active Immunotherapy, *Trends in Immunology*, vol. 24 (6), pp. 334-341, Jun. 1, 2003.

Mechetner et al., Efficient Inhibition of P-Glycoportein-Mediated Multidrug Resistance with a Monoclonal Antibody, *Proceedings of the National Academy of Science USA*, vol. 89, pp. 5824-5828, Jul. 1, 1992.

Miller et al., P-Glycoprotein Expression in Malignant Lymphoma and Reversal of Clinical Drug Resistance with Chemotherapy Plus High0Dose Verapamil, *Journal of Clinical Oncology*, vol. 9 (1), pp. 17-24, Jan. 1, 1991.

Muhs et al., Improved Memory Capacity of Amyloid Precursor Protein Transgenic mice Through Passive Administration of a Monoclonal Antibody Inducing a Conformational Shift of Amyloid-Beta, *The Journal of the Alzheimer's Association*, vol. 2 (3), pp. S21, Jan. 17, 2006.

Pawlak-Robin et al., Inhibition of Multidrug Resistance by Immunisation with Synthetic P-glycoprotein-derived Peptides, *European Journal of Cancer*, vol. 40, pp. 606-613, Jan. 1, 2004.

Petkova et al., A Structural Model for Alzheimer's β-Amyloid Fibrils Based on Experiemental Constraints from Solid State NMR, *Proceedings of the National Academy of Science USA*, vol. 99 (26), pp. 16742-16747, Dec. 24, 2002.

Pierre et al., In vitro and In vivo Circumvention of Multidrug Resistance by Servier 9788, a Novel Triazinominopiperidine Derivative, *Investigational New Drugs*, vol. 10, pp. 137-148, Jan. 1, 1992.

Roberts et al., Chemistry for Peptide and Protein PEGlation, *Advanced Delivery Reviews*, vol. 54, pp. 459-476, Jan. 1, 2002.

Schinkel et al., Binding Properties of Monoclonal Antibodies Recognizing External Epitopes of the Human MDR1 P-Glycoprotein, *Int. Journal of Cancer*, vol. 55, pp. 478-484, Jan. 1, 1993.

Schnolzer et al., Constructing Proteins by Dovetailing Unprotected Synthetic Peptides: Backbone-Engineered HIV Protease, *Science*, vol. 256 (5054), pp. 221-225, Apr. 10, 1992.

Solomon, B., Immunological Approach for the Treatment of Alzheimer's Disease, *Journal of Molecular Neuroscience*, vol. 20, pp. 283-286, Jan. 1, 2003.

(56) References Cited

OTHER PUBLICATIONS

Stober et al., Synthesis of Characteristic Lipopeptides of the Human N-Ras Protein and their Evaluation as Possible Inhibitors of Protein Farnesyl Transferase, *Bioorganic & Medicinal Chemistry*, vol. 5 (1), pp. 75-83, Jan. 1, 1997.
Stupp et al., Ventricular Arrhythmia and Torsade de Pointe: Dose Limiting Toxicities of the MDR-Modulator S9788 in a Phase I Trials, *Annals of Oncology*, vol. 9, pp. 1233-1242, Jan. 1, 1998.
Thiebault et al., Cellular Localization of the Multidrug-Resistance Gene Product P-Glycoprotein in Normal Human Tissues, *Proceedings of the National Academy of Science USA*, vol. 84, pp. 7735-7738, Nov. 1, 1987.
Tosi et al., Immune Response Against the Murine MDRI Protein Induced by Vaccination with Synthetic Lipopeptides in Liposomes, *Biochemical and Biophysical Research Communications*, vol. 212 (2), pp. 494-500, Jul. 17, 1995.
Tsuruo, T., Circumvention of Drug Resistance with Calcium Channel Blockers and Monoclonal Antibodies, *Drug Resistance in Cancer Therapy*, vol. 48, pp. 73-95, Jan. 1, 1989.
Van Der Bliek et al., Sequence of mdr3 cDNA Encoding a Human P-Glycoprotein, *Gene*, vol. 71, pp. 401-411, Jan. 1, 1988.
Wiame, Ilse, EPO Search Report issued in Appl. No. EP 12 15 3152, pp. 1-10, May 9, 2012.
Wolf-Klein et al., Conceptualizing Alzheimer's Disease as a Terminal Medical Illness (Abstract only), *American Journal of Hospital Palliative Care*, vol. 24 (1), pp. 77-82, Feb. 1, 2007.
Yang et al., Treatment of Multidrug Resistant (MDR1) Murine Leukemia with P-Glycoprotein Substrates Accelerates the Course of the Disease, *Biochemical and Biophysical Research Communication*, vol. 266, pp. 167-163, Jan. 1, 1999.
Zhang et al., Multiple-Peptides Conjugates for Binding βAmyloid Plaques of Alzheimer's Disease, *Bioconjugate Chemistry*, vol. 14, pp. 86-92, Dec. 7, 2002.
International Preliminary Report on Patentability for PCT/EP2011/068797 dated May 10, 2013, pp. 1-9.
International Search Report and Written Opinion dated Mar. 16, 2012 for PCT/EP2011/068797, pp. 1-11.
Allen, T. et al., "Use of the Post-Insertion Method for the Formation of Ligand-Coupled Liposomes," Cellular & Molecular Biology Letters, 2002, vol. 7, pp. 889-894.
Allison, A. et al., "Liposomes as Immunological Adjuvants," Nature Nov. 15, 1974, vol. 252, p. 252.
Alving, C. et al., "Liposomes as Carriers of Peptide Antigens: Induction of Antibodies and Cytoxic T Lymphocytes to Conjugated and Unconjugated Peptides," Immunological Reviews 1995, No. 145, pp. 1-27.

Fieser, T. et al., "Influence of Protein Flexibility and Peptide Conformation on Reactivity of Monoclonal Anti-Peptide Antibodies with a Protein α-Helix," Proc. Natl. Acad. Sci., Dec. 1987, vol. 84, pp. 8568-8572.
Frisch, B. et al., "Parameters Affecting the Immunogenicity of a Liposome-Associated Synthetic Hexapeptide Antigen," Eur. J. Immunol. 1991, vol. 21, pp. 185-193.
Guan, H. et al., "Liposomal Formulations of Synthetic MUC1 Pepdtides: Effects of Encapsulation versus Surface Display of Peptides on Immune Responses," Bioconjugate Chemistry 1998, vol. 9, No. 4, pp. 451-458.
Kersten, G. et al., "Liposomes and ISCOMS as Vaccine Formulations," Biochimica et Biophysica Acta 1241 1995, pp. 117-138.
Lu, Stephen M. et al., "A *de Novo* Designed Template for Generating Conformation-Specific Antibodies That Recognize α-Helices in Proteins," The Journal of Biological Chemistry, Jun. 28, 2002, vol. 277, No. 26, pp. 23515-23524.
Moreira, J. et al., "Use of the Post-Insertion Technique to Insert Peptide Ligands into Pre-Formed Stealth Liposomes with Retention of Binding Activity and Cytotoxicity," Pharmaceutical Research, Mar. 2002, vol. 19, No. 3, pp. 265-269.
Nicolau, C. et al., "A Liposome-Based Therapeutic Vaccine Aginst β-Amyloid Plaques on the Pancreas of Transgenic NORBA Mice," PNAS, Feb. 19, 2002, vol. 99, No. 4, pp. 2332-2337.
O'Nuallain, B. et al., "Conformational Abs Recognizing a Generic Amyloid Fibril Epitope," PNAS, Feb. 5, 2002, vol. 99. No. 3, pp. 1485-1490.
Schmechel, A. et al., "Alzheimer β-Amyloid Homodimers Facilitate Aβ Fibrillization and the Generation of Conformational Antibodies," The Journal of Biological Chemistry, Sep. 12, 2003, vol. 278, No. 37, pp. 35317-35324.
Torchilin, V., "Recent Advances with Liposomes as Pharmaceutical Carriers," Nature Reviews, Feb. 2005, vol. 4, pp. 145-160.
International Search Report and Written Opinion dated Nov. 29, 2011 in PCT International Patent Application No. PCT/EP2011/063933, pp. 1-3.
Frisch Benoît et al., "Synthetic Peptide-Based Highly Immunogenic Liposomal Constructs," Methods in Enzymology, Jan. 1, 2003, vol. 373, pp. 51-73.
Muhs, A. et al., "Liposomal Vaccines with Conformation-Specific Amyloid Peptide Antigens Define Immune Response and Efficacy in APP Transgenic Mice," Proceedings of the National Academy of Sciences of USA, Jun. 5, 2007, vol. 104, No. 23, pp. 9810-9815.
International Preliminary Examination Report on Patentability dated Feb. 12, 2013 in PCT International Patent Application No. PCT/EP2011/063933, pp. 1-7.

\* cited by examiner

SEQUENCE LISTING

```
<160> NUMBER OF SEQ ID NOS: 16

<210> SEQ ID NO 1
<211> LENGTH: 30
<212> TYPE: PRT
<213> ORGANISM: Homo sapiens
<220> FEATURE:
<221> NAME/KEY: VARIANT
<222> LOCATION: (18)..(18)
<223> OTHER INFORMATION: /replace="phosphorylated serine"
<220> FEATURE:
<221> NAME/KEY: VARIANT
<222> LOCATION: (26)..(26)
<223> OTHER INFORMATION: /replace="phosphorylated serine"

<400> SEQUENCE: 1

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 2
<211> LENGTH: 16
<212> TYPE: PRT
<213> ORGANISM: Homo sapiens
<220> FEATURE:
<221> NAME/KEY: VARIANT
<222> LOCATION: (14)..(14)
<223> OTHER INFORMATION: /replace="phosphorylated tyrosine"

<400> SEQUENCE: 2
```

```
Arg Gln Glu Phe Glu Val Met Glu Asp His Ala Gly Thr Tyr Gly Leu
1               5                   10                  15
```

<210> SEQ ID NO 3
<211> LENGTH: 16
<212> TYPE: PRT
<213> ORGANISM: Homo sapiens
<220> FEATURE:
<221> NAME/KEY: VARIANT
<222> LOCATION: (7)..(7)
<223> OTHER INFORMATION: /replace="phosphorylated threonine"
<220> FEATURE:
<221> NAME/KEY: VARIANT
<222> LOCATION: (9)..(9)
<223> OTHER INFORMATION: /replace="phosphorylated serine"

<400> SEQUENCE: 3

```
Pro Gly Ser Arg Ser Arg Thr Pro Ser Leu Pro Thr Pro Pro Thr Arg
1               5                   10                  15
```

<210> SEQ ID NO 4
<211> LENGTH: 16
<212> TYPE: PRT
<213> ORGANISM: Homo sapiens
<220> FEATURE:
<221> NAME/KEY: VARIANT
<222> LOCATION: (7)..(7)
<223> OTHER INFORMATION: /replace="phosphorylated serine"
<220> FEATURE:
<221> NAME/KEY: VARIANT
<222> LOCATION: (10)..(10)
<223> OTHER INFORMATION: /replace="phosphorylated threonine"

<400> SEQUENCE: 4

```
Gly Tyr Ser Ser Pro Gly Ser Pro Gly Thr Pro Gly Ser Arg Ser Arg
1               5                   10                  15
```

<210> SEQ ID NO 5
<211> LENGTH: 16
<212> TYPE: PRT
<213> ORGANISM: Homo sapiens
<220> FEATURE:
<221> NAME/KEY: VARIANT
<222> LOCATION: (4)..(4)
<223> OTHER INFORMATION: /replace="phosphorylated serine"
<220> FEATURE:
<221> NAME/KEY: VARIANT
<222> LOCATION: (12)..(12)
<223> OTHER INFORMATION: /replace="phosphorylated serine"

<400> SEQUENCE: 5

```
Val Tyr Lys Ser Pro Val Val Ser Gly Asp Thr Ser Pro Arg His Leu
1               5                   10                  15
```

<210> SEQ ID NO 6
<211> LENGTH: 18
<212> TYPE: PRT
<213> ORGANISM: Homo sapiens
<220> FEATURE:
<221> NAME/KEY: VARIANT
<222> LOCATION: (4)..(4)
<223> OTHER INFORMATION: /replace="phosphorylated serine"
<220> FEATURE:
<221> NAME/KEY: VARIANT
<222> LOCATION: (9)..(9)
<223> OTHER INFORMATION: /replace="phosphorylated serine"

<400> SEQUENCE: 6

```
Gly Asp Thr Ser Pro Arg His Leu Ser Asn Val Ser Ser Thr Gly Ser
1               5                   10                  15
```

Ile Asp

```
<210> SEQ ID NO 7
<211> LENGTH: 17
<212> TYPE: PRT
<213> ORGANISM: Homo sapiens
<220> FEATURE:
<221> NAME/KEY: VARIANT
<222> LOCATION: (3)..(3)
<223> OTHER INFORMATION: /replace="phosphorylated serine"
<220> FEATURE:
<221> NAME/KEY: VARIANT
<222> LOCATION: (6)..(6)
<223> OTHER INFORMATION: /replace="phosphorylated threonine"
<220> FEATURE:
<221> NAME/KEY: VARIANT
<222> LOCATION: (13)..(13)
<223> OTHER INFORMATION: /replace="phosphorylated threonine"
<220> FEATURE:
<221> NAME/KEY: VARIANT
<222> LOCATION: (15)..(15)
<223> OTHER INFORMATION: /replace="phosphorylated serine"

<400> SEQUENCE: 7

Pro Gly Ser Pro Gly Thr Pro Gly Ser Arg Ser Arg Thr Pro Ser Leu
1               5                   10                  15

Pro

<210> SEQ ID NO 8
<211> LENGTH: 12
<212> TYPE: PRT
<213> ORGANISM: Homo sapiens
<220> FEATURE:
<221> NAME/KEY: VARIANT
<222> LOCATION: (3)..(3)
<223> OTHER INFORMATION: /replace="phosphorylated serine"

<400> SEQUENCE: 8

His Leu Ser Asn Val Ser Ser Thr Gly Ser Ile Asp
1               5                   10

<210> SEQ ID NO 9
<211> LENGTH: 10
<212> TYPE: PRT
<213> ORGANISM: Homo sapiens
<220> FEATURE:
<221> NAME/KEY: VARIANT
<222> LOCATION: (6)..(6)
<223> OTHER INFORMATION: /replace="phosphorylated serine"

<400> SEQUENCE: 9

Val Ser Gly Asp Thr Ser Pro Arg His Leu
1               5                   10

<210> SEQ ID NO 10
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: antigenic peptide Alpha Beta 1-15

<400> SEQUENCE: 10

Asp Ala Glu Phe Arg His Asp Ser Gly Tyr Glu Val His His Gln
1               5                   10                  15

<210> SEQ ID NO 11
<211> LENGTH: 16
```

```
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: antigenic peptide Alpha Beta 1-16

<400> SEQUENCE: 11

Asp Ala Glu Phe Arg His Asp Ser Gly Tyr Glu Val His His Gln Lys
1               5                   10                  15

<210> SEQ ID NO 12
<211> LENGTH: 15
<212> TYPE: PRT
<213> ORGANISM: Homo sapiens
<220> FEATURE:
<221> NAME/KEY: VARIANT
<222> LOCATION: (1)..(15)
<223> OTHER INFORMATION: antigenic peptide Alpha Beta 1-16 (deletion at
      position 14)

<400> SEQUENCE: 12

Asp Ala Glu Phe Arg His Asp Ser Gly Tyr Glu Val His Gln Lys
1               5                   10                  15

<210> SEQ ID NO 13
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: antigenic peptide Alpha Beta 4-11

<400> SEQUENCE: 13

Phe Arg His Asp Ser Gly Tyr Glu
1               5

<210> SEQ ID NO 14
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: antigenic peptide Alpha Beta 22-35

<400> SEQUENCE: 14

Glu Asp Val Gly Ser Asn Lys Gly Ala Ile Ile Gly Leu
1               5                   10

<210> SEQ ID NO 15
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: antigenic peptide Afb02 29-40
<220> FEATURE:
<221> NAME/KEY: MISC_FEATURE
<222> LOCATION: (1)..(12)
<223> OTHER INFORMATION: antigenic peptide Alpha Beta 29-40

<400> SEQUENCE: 15

Gly Ala Ile Ile Gly Leu Met Val Gly Gly Val Val
1               5                   10

<210> SEQ ID NO 16
```

```
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: antigenic peptide Alpha Beta 1-5

<400> SEQUENCE: 16

Asp Ala Glu Phe Arg
1               5
```

VACCINE ENGINEERING

CROSS-REFERENCE TO RELATED APPLICATIONS

This application is a 35 U.S.C. §371 national stage application of International Patent Application No. PCT/EP2011/063933 filed on Aug. 12, 2011, which claims the benefit of priority to European Patent Application No. 10172619.8 filed on Aug. 12, 2010, the disclosures of which are hereby incorporated by reference.

The present invention discloses and claims methods of preparing immunogenic constructs for generating an improved conformation specific immune response and/or for producing improved conformation specific antibodies. The invention further relates to the immunogenic constructs, antibodies, pharmaceutical compositions and methods for treating diseases or disorders associated with the aggregation of peptides.

The role of immunogen conformation upon the specificity and efficacy of the humoral immune response has been recognized in a number of recent therapeutic and prophylactic vaccines. Conformation-specific antibodies generated by immunization with conformationally-restricted immunogens are also important tools for disease diagnosis, as biochemical probes for establishing protein structure-function relationships and in affinity purification. Development of such peptide immunogens however has thus far been hindered by the lack of general design strategies to control the conformation of a given peptide sequence. In addition, most naked peptides have low inherent immunogenicity. While design of peptide templates for the generation of antibodies which selectively recognise protein epitopes with an α-helical conformation have been reported (Fieser, T. M. et al., Proc. Natl. Acad. Sci. U.S.A. 84, 8568 (1987); Lu, S. M. & Hodges, R. S., J. Biol. Chem. 277, 23515 (2002)), general strategies to design short peptide fragments as immunogens for targeting other protein conformations are lacking.

Protein aggregation resulting from aberrant folding is characterized by the formation of proteinaceous deposits called amyloid which exhibit β-sheet structure. Misfolding is now associated with over 20 human diseases including Alzheimer's Disease (AD), Huntington's Disease and Type II diabetes mellitus. Vaccines which can elicit antibodies against only the pathological β-sheet multimers of these targets would thus be considered advantageous from an efficacy perspective, but also particularly from a safety perspective where the non-folded protein has physiological relevance.

In AD, β-amyloid peptides (Aβ) $A\beta_{1-40}$ and $A\beta_{1-42}$ have been associated with disease progression over several decades of research and the β-sheet aggregates of Aβ are one of the major pathological hallmarks of AD. While the etiology of AD has not yet been elucidated, a large variety of soluble and insoluble β-sheet $A\beta_{1-40/42}$ oligomers with different degrees of polymerization have been identified in vitro or in AD brain as synaptotoxic and likely causal agents of cognitive impairment.

The discovery that active vaccination of transgenic mice, over-expressing human amyloid precursor protein (APP) with $A\beta_{1-42}$ peptide fibers could be an effective means to modify disease progression has opened up new vistas in AD therapy. The importance of immunogen aggregation-state upon immune response specificity has been demonstrated by the generation of antibodies with binding specificities for fibrillar (O'Nuallain, B. & Wetzel, R., Proc. Natl. Acad. Sci, U.S.A. 99, 1485 (2002)) as well as a range of soluble forms of $A\beta_{1-40/42}$ (Schmechel, A. et al., "Alzheimer beta-amyloid homodimers facilitate A beta fibrillization and the generation of conformational antibodies," J. Biol. Chem. 278, 35317 (2003)). Control of peptide aggregation-state, is however, precarious due to the stability issues associated with oligomers held together by non-covalent bonds. As a result of this, peptide immunogens are frequently used as heterogeneous mixtures of different secondary and quaternary structures (WO 2007068411). On the other hand, vaccines which make use of covalently stabilized peptide multimers have hitherto been designed using de novo strategies that are not readily adaptable to target different oligomeric species.

There is therefore a need for developing methods that would allow to rationally design immunogenic constructs such that a conformation specific immune response is elicited in an animal or a human.

This objective is addressed and solved by the present invention by providing methods and immunogenic constructs comprising a peptide molecule that upon administration to an animal or a human exhibit a predefined secondary and/or quaternary structure and are thus capable of generating a conformation specific immune response.

The method and constructs according to the invention now make it possible to prepare vaccines which can specifically elicit antibodies against only the pathological conformation of a target peptide such as, for example, the β-sheet multimers of a beta-amyloid target, but do not affect the non-pathological conformation, which may have physiological relevance.

The method and constructs disclosed and claimed herein allow to control peptide conformation by modulation of the peptide lipidation pattern, lipid anchor chain length, spacer and/or liposome composition, and/or via co-administration of small molecules. Accordingly, this technology can be applied to the rational design of liposomal vaccines. Selective targeting of the pathological conformation of a target protein as described herein, can be expected to contribute to the generation of more efficacious diagnostic tools and of safer and more efficacious therapies for a range of human disease, in particular those based on misfolded proteins.

In particular, the present invention relates to a method of preparing a modulated immunogenic construct for generating an immune response in an animal or a human, wherein said immunogenic construct comprises a peptide molecule and a hydrophobic moiety covalently bound to the C- and/or N-terminal part of the peptide molecule, which peptide molecule is anchored into the lipid membrane of a liposomal carrier via said hydrophobic moiety, said method comprising a. modulating the secondary and/or quaternary structure and the extent of β-sheet structure and/or β-sheet aggregation of the liposome-bound peptide molecule, comprising
  i. modulating the amount of metal ions capable of disrupting peptide-liposome or peptide-peptide stabilizing interactions in the liposomal solution or composition, i.e., by adding or removing from the liposomal solution or composition said metal ions; and/or
  ii. changing the net surface potential of the liposome by modulating, i.e., by increasing or decreasing, the proportion of anionic or cationic lipids in the lipid bilayer of the liposome; and/or
  iii. varying the total number of hydrophobic moieties covalently bound to the N- and/or C-terminus of the peptide molecule such that there is a disparity in the number of hydrophobic moieties between the N- and the C-terminus and, optionally, also the varying the length of the hydrophobic moieties; or iv. maintaining an equal number of hydrophobic moieties covalently bound to the N- and/or C-terminus, and varying the length of hydrophobic moieties; and/or
v. adding small molecules to a liposomal solution or composition which are capable of either disaggregating β-sheet structures or promoting aggregation to form β-sheet structures; and
b. determining the extent of β-sheet structure and/or β-sheet aggregation of the liposome-bound antigenic peptide; and
c. obtaining the modulated immunogenic construct.

In one embodiment, the present invention relates to a method of preparing a modulated immunogenic construct for generating an immune response in an animal or a human, wherein said immunogenic construct comprises a peptide molecule and a hydrophobic moiety covalently bound to the C- and/or N-terminal part of the peptide molecule, which peptide molecule is anchored into the lipid membrane of a liposomal carrier via said hydrophobic moiety, said method comprising a. modulating the secondary and/or quaternary structure and the extent of β-sheet structure and/or β-sheet aggregation of the liposome-bound peptide molecule, comprising i. changing the net surface potential of the liposome by modulating, i.e., increasing or decreasing, in the lipid bilayer of the liposome the proportion of anionic or cationic lipids; and ii. varying the total number of hydrophobic moieties bound to the peptide molecule, particularly of hydrophobic moieties bound to the N- and/or C-terminus of the peptide molecule such that there is a disparity in the number of hydrophobic moieties between the N- and the C-terminus, and/or, optionally, the position of the sites on the peptide molecule, where the hydrophobic moieties become covalently bound to the peptide molecule; or iii. maintaining an equal number of hydrophobic moieties covalently bound to the N- and/or C-terminus and varying the length of hydrophobic moieties; and, optionally, iv. adding to the liposomal solution or composition small molecules which are capable of either disaggregating β-sheet structures or promoting aggregation to form β-sheet structures and/or v. modulating, i.e., adding to or removing, from the liposomal solution metal ions which are capable of disrupting peptide-liposome or peptide-peptide stabilizing interactions.

In one embodiment, the invention relates to a method of preparing a modulated immunogenic construct for generating an immune response in an animal or a human, wherein said immunogenic construct comprises a peptide molecule and a hydrophobic moiety covalently bound to the C- and/or N-terminal part of the peptide molecule, which peptide molecule is anchored into the lipid membrane of a liposomal carrier via said hydrophobic moiety, said method comprising a. modulating the secondary and/or quaternary structure and the extent of β-sheet structure and/or β-sheet aggregation of the liposome-bound peptide molecule, comprising i. changing the net surface potential of the liposome by modulating, i.e., increasing or decreasing, in the lipid bilayer of the liposome the proportion of anionic or cationic lipids; and ii. varying the total number of hydrophobic moieties bound to the peptide molecule, particularly of hydrophobic moieties bound to the N- and/or C-terminus of the peptide molecule such that there is a disparity in the number of hydrophobic moieties between the N- and the C-terminus, and/or, optionally, the position of the sites on the peptide molecule, where the hydrophobic moieties become covalently bound to the peptide molecule; or iii. maintaining an equal number of hydrophobic moieties covalently bound to the N- and/or C-terminus and varying the length of hydrophobic moieties In one embodiment, the invention provides a method of modulating the secondary and/or quaternary structure of an antigenic peptide molecule, which peptide molecule has a hydrophobic moiety covalently bound to its C- and/or N-terminus and is anchored into the lipid membrane of a liposomal carrier via said hydrophobic moiety, comprising a. modulating the amount of metal ions capable of disrupting peptide-liposome or peptide-peptide stabilizing interactions in the liposomal solution or composition; and/or b. changing the net surface potential of the liposome by modulating the proportion of anionic or cationic lipids in the lipid bilayer of the liposome; and/or c. varying the total number of hydrophobic moieties covalently bound to the N- and/or C-terminus of the peptide molecule such that there is a disparity in the number of hydrophobic moieties between the N- and the C-terminus; or d. maintaining an equal number of hydrophobic moieties covalently bound to the N- and/or C-terminus and varying the length of hydrophobic moieties; and/or e. adding small molecules to a liposomal solution or composition which are capable of either disaggregating β-sheet structures or promoting aggregation to form β-sheet structures, wherein said modulation of the secondary and/or quaternary structure leads to an increase or decrease of the extent of β-sheet structures and/or β-sheet aggregation of the liposome-bound antigenic peptides.

In one embodiment of the invention, a peptide molecule is provided anchored into the membrane of a liposome via a hydrophobic moiety covalently bound to the C- and/or N-terminal part of the peptide molecule, wherein said hydrophobic moiety is an alkyl group, a fatty acid, a triglyceride, diglyceride, steroid, sphingolipid, glycolipid or a phospholipid, particularly an alkyl group or a fatty acid, particularly with a carbon backbone of at least 3 carbon atoms, particularly of at least 4 carbon atoms, particularly of at least 6 carbon atoms, particularly of at least 8 carbon atoms, particularly of at least 12 carbon atoms, particularly of at least 16 carbon atoms.

In one embodiment of the invention, the hydrophobic moiety is palmitic acid.

In one aspect, the present invention contemplates modulating the secondary and/or quaternary structure of the peptide molecule, particularly the liposome-embedded peptide molecule, such as to increase the extent of β-sheet structure and/or β-sheet aggregation, particularly by removing and/or inactivating metal ions, which are capable of disrupting peptide-liposome or peptide-peptide stabilizing interactions. In one embodiment, this may be achieved by adding one or more metal chelating agents to the liposomal solution or a liposomal composition.

In another aspect, the present invention contemplates modulating the secondary and/or quaternary structure of the peptide molecule, particularly the liposome-embedded peptide molecule, such as to enhance the formation of β-sheet aggregates by adding one or more compounds which are capable of stabilising the formation of β-sheet aggregates. In one embodiment this may be achieved by adding one or more compounds selected from the group consisting of heparin, myo-inositol hexasulfate, glycogen and ellagic acid.

In another aspect, the present invention contemplates modulating the secondary and/or quarternary conformation of the peptide molecule, particularly the liposome-embedded peptide molecule, such as to increase the extent of β-sheet structure and/or β-sheet aggregation, particularly by 50%-100%, more particularly by 80-100%, by increasing the net negative surface potential of the liposome, particularly from >+35 mV to at least <0 mV, particularly to at least <−10 mV, particularly to at least <−40 mV, in PBS. In one embodiment this may be accomplished by exchanging a proportion of cationic lipids in the lipid bilayer of the liposome with an equal proportion of anionic lipids.

The liposome surface potential (zeta potential) of the liposome is determined as described in Examples (Part I, C2).

In another aspect, the present invention contemplates modulating the secondary and/or quarternary structure of the peptide molecule, particularly the liposome-embedded peptide molecule, such as to decrease the extent of β-sheet structure and/or β-sheet aggregation, particularly by 50%-100%, more particularly by 80-100%, by decreasing the net negative surface potential of the liposome, particularly from <−10 mV to at least >0 mV, particularly to at least >+10 mV, particularly to at least >+35 mV, in PBS. In one embodiment this may be accomplished by exchanging a proportion of anonic lipids in the lipid bilayer of the liposome with an equal proportion of cationic lipids.

The liposome surface potential (zeta potential) of the liposome is determined as described in Examples (Part I, C2).

In one embodiment, the invention contemplates using as a replacement for cationic lipids in the liposomal membrane, anionic lipids selected from the group consisting of:
 a. diacyl-phospholipids with headgroups phosphatidyl glycerol, phosphatidyl serine, phosphatidyl inositol, L-α-phosphatidylinositol-4-phosphate or phosphatidic acid;
 b. lyso-phospholipids with headgroups phosphatidyl glycerol, phosphatidyl serine or phosphatidic acid, and
 c. cardiolipin, dilyso-cardiolipin, monolyso-cardiolipin
 d. diether-phospholipids with headgroups phosphatidyl glycerol, phosphatidyl serine, phosphatidyl inositol, L-α-phosphatidylinositol-4-phosphate or phosphatidic acid;
 e. glycolipids or lipopolysaccharides In one aspect, the invention contemplates using as a replacement for anionic lipids in the liposomal membrane, cationic lipids selected from the group consisting of:
 a. diacyl-phospholipids with headgroups 3-trimethylammonium-propane, 3-dimethylammonium-propane, 3-ethylphosphocholine or 3-phosphatidylethanolamine;
 b. diether-phospholipids with headgroups 3-trimethylammonium-propane, 3-dimethylammonium-propane, 3-ethylphosphocholine or 3-phosphatidylethanolamine;
 c. lyso-phospholipids with headgroups 3-trimethylammonium-propane, 3-dimethylammonium-propane, 3-ethylphosphocholine or 3-phosphatidylethanolamine.
 d. D-erythro-sphingosine, dimethyldioctadecylammonium bromide, N-[1-(2,3-dimyristyloxy)propyl]-N,N-dimethyl-N-(2-hydroxyethyl) ammonium bromide, N,N,N-trimethyl-2-bis[(1-oxo-9-octadecenyl)oxy]-(Z, Z)-1-propanaminium methyl sulfate or 3β-[N—(N',N'-dimethylaminoethane)-carbamoyl]cholesterol hydrochloride.

In one embodiment of the invention, the lipid chains attached to the above headgroups can
 a. be saturated or unsaturated,
 b. vary in length from $(CH_2)_n$ wherein n is between 3 and 24, and
 c. be symmetrically or asymmetrically substituted.

In one aspect, the invention contemplates modulating the secondary and/or quaternary structure of the peptide molecule, particularly the liposome-embedded peptide molecule, by varying the total number and/or position of the hydrophobic moieties covalently bound to the N- and/or the C-terminus of the peptide molecule.

In a specific embodiment of the invention, the secondary and/or quaternary structure of the peptide molecule, particularly the liposome-embedded peptide molecule, is modulated by varying the total number of the hydrophobic moieties covalently bound to the N- and/or the C-terminus of the peptide molecule such that there is a disparity in the number of hydrophobic moieties between the N- and the C-terminus. In particular, the number of hydrophobic moieties covalently bound to the N-terminus of the peptide molecule exceeds the number of hydrophobic moieties covalently bound to the C-terminus of the peptide molecule by at least one, at least two, at least three, at least four moieties, or, vice versa, the number of hydrophobic moieties covalently bound to the C-terminus of the peptide molecule exceeds the number of hydrophobic moieties covalently bound to the N-terminus of the peptide molecule by at least one, at least two, at least three, at least four moieties.

In another specific embodiment of the invention, the peptide molecule, particularly the liposome-embedded peptide molecule, is modulated such that at least one, particularly at least two, particularly at least three, particularly at least four hydrophobic moieties are covalently bound to the N- and/or the C-terminus of the peptide molecule.

In another specific embodiment of the invention, the peptide molecule, particularly the liposome-embedded peptide molecule, is modulated such that one hydrophobic moiety, particularly 2 hydrophobic moieties, particularly 3 hydrophobic moieties, particularly 4 hydrophobic moieties are covalently bound to the N- and/or the C-terminus of the peptide molecule.

In one embodiment of the invention the number of hydrophobic moieties covalently bound to the N-terminus and the C-terminus of the peptide molecule and to the C-terminus and N-terminus, respectively, is 0:1; 1:1; 2:1; 2:0; particularly 2:2; particularly 3:1, particularly 3:2, particularly 4:1, particularly 4:2, but especially 4:0.

In one embodiment of the invention, at least 4 hydrophobic moieties are covalently bound to the N-terminus of the peptide molecule and no hydrophobic moiety is bound to the C-terminus of the peptide molecule.

In one embodiment of the invention, at least 4 hydrophobic moieties are covalently bound to the C-terminus of the peptide molecule and no hydrophobic moiety is bound to the N-terminus of the peptide molecule.

In another specific embodiment of the invention, the secondary and/or quaternary structure is modulated by varying the length of the hydrophobic anchor(s), which is in one embodiment an alkyl group or a fatty acid with a carbon backbone of at least 1 carbon atom, particularly of at least 2 carbon atoms, particularly of at least 3 carbon atoms, particularly of at least 4 carbon atoms, particularly of at least 6 carbon atoms, particularly of at least 8 carbon atoms, particularly of at least 12 carbon atoms, particularly of at least 16 carbon atoms.

In another specific embodiment of the invention, the secondary and/or quaternary structure is modulated by varying the length of the hydrophobic anchor(s), which is in one embodiment an alkyl group or a fatty acid with a carbon backbone of 1 carbon atom, particularly of 2 carbon atoms, particularly of 3 carbon atoms, particularly of 4 carbon atoms, particularly of 6 carbon atoms, particularly of 8 carbon atoms, particularly of 12 carbon atoms, particularly of 16 carbon atoms.

In another embodiment, the alkyl group has a carbon backbone of ≤4 carbon atoms.

A fatty acid anchor with a carbon backbone of >4 carbon atoms is believed to favour induction of a β-sheet conformation, whereas a fatty acid anchor with a carbon backbone of ≤4 carbon atoms is believed to favour induction of a random coil conformation.

In one aspect, the present invention contemplates all possible combinations of the foregoing modulation activities, in particular a combination of (a) the removing and/or inactivating of metal ions with (b) the adding of one or more compounds which are capable of stabilising the formation of β-sheet aggregates and/or (c) the increasing of the net negative surface potential of the liposome, i.e. by replacing a proportion of cationic lipids in the lipid bilayer of the liposome with an equal proportion of anionic lipids, and/or (d) the varying of the total number of the hydrophobic moieties covalently bound to the N- and/or the C-terminus of the peptide molecule such that there is a disparity in the number of hydrophobic moieties between the N- and the C-terminus; and/or (e) the varying of the length of the hydrophobic anchor(s), Also contemplated is a combination of (b) the adding of one or more compounds which are capable of stabilising the formation of β-sheet aggregates with (c) the increasing of the net negative surface potential of the liposome, and/or (d) the varying of the total number of the hydrophobic moieties covalently bound to the N- and/or the C-terminus of the peptide molecule such that there is a disparity in the number of hydrophobic moieties between the N- and the C-terminus; and/or (e) the varying of the length of the hydrophobic anchor(s), with all the variations as described herein in the specific embodiments.

Also contemplated is a combination of (c) the increasing of the net negative surface potential of the liposome with (d) the varying of the total number of the hydrophobic moieties covalently bound to the N- and/or the C-terminus of the peptide molecule such that there is a disparity in the number of hydrophobic moieties between the N- and the C-terminus; and/or (e) the varying of the length of the hydrophobic anchor(s), with all the variations as described herein in the specific embodiments.

Also contemplated is a combination of (d) the varying of the total number of the hydrophobic moieties covalently bound to the N- and/or the C-terminus of the peptide molecule such that there is a disparity in the number of hydrophobic moieties between the N- and the C-terminus with (e) the varying of the length of the hydrophobic anchor(s), with all the variations as described herein in the specific embodiments.

The peptide molecules, particularly the liposome-embedded peptide molecules, resulting from the above modulating activities, particularly from the above combinations of the modulating activities, are also part of the present invention.

In one aspect, the invention contemplates modulating the secondary and/or quaternary structure of the peptide molecule by disaggregating β-sheet aggregates.

In one embodiment of the invention, disaggregation of β-sheet aggregates is accomplished by adding to the liposomal solution or composition a small molecule capable of disaggregating β-sheet aggregates, particularly a small molecule selected from the group consisting of tannic acid, rosmarinic acid, methylene blue, scyllo-cyclohexanehexyl, scyllo-inositol, (+)-catechin, 4,5-dianilinophthalimide, dopamine, L-dopa, rifampicin, 4'-iodo-4'-deoxydoxorubicin, nordihydroguaretic acid, curcumin, 3-amino-1-propanesulfonic acid, piceid, nicotine, myricetin, morin, quercetin, kaempferol, (+)-catechin, (−)-epicatechin gallic acid, epicatechin gallate, epigallocatechin gallate, porphyrin phthalocyanine, rifampicin, tetracycline, curcumin, ferulic acid, estriol, vitamin A, beta-carotene, coenzyme O10, ibuprofen, aspirin, acetaminophen, meclofenamic acid, sulindac sulfide, ketoprofen, flurbiprofen, diclofenac, naproxen, indomethacin, selegiline, pergolide and bromocriptine.

Further molecules that can be used within the present invention for disaggregating β-sheet aggregates are disclosed in international application published as WO/2008/061795 and WO/2008/061796, respectively, the disclosure of which is incorporated herein in its entirety.

In one embodiment of the invention, disaggregation of β-sheet aggregates is accomplished by adding to the liposomal solution or composition one or more metal ions which are capable of disrupting peptide-liposome or peptide-peptide stabilizing interactions, particularly Cu(II) and/or Zn(II).

Generally, the present method for preparing an immunogenic construct for generating a conformation specific immune response in an animal or a human can be applied to any peptide molecule.

In one embodiment of the invention, the method is applied to peptides available in proteins, the misfolding of which is known to cause diseases in humans and animals.

In one embodiment, the peptide molecule is a peptide derived from an amyloid protein or amyloid-like protein such as, for example prion protein, tau protein, alpha-synuclein, huntingtin.

In particular, the peptide molecule is an Aβ peptide derived from the N-terminus of an amyloid protein or amyloid-like protein, particularly an Aβ peptide and/or truncated Aβ fragment longer than 5 amino acids; 5 and 16 amino acids; 6 and 12 amino acids; or 4 and 9 amino acids, particularly an $A\beta_{1-30}$; an $A\beta_{1-20}$; an $A\beta_{1-16}$; an $A\beta_{1-15}$; or an $A\beta_{1-9}$.

In one embodiment, the peptide molecule is a peptide derived from a tau protein, particularly a human tau protein, particularly a molecule comprising a phospho-peptide mimicking a major pathological phospho-epitope of protein tau.

In one embodiment, said tau protein has an amino acid sequence identity a. to SEQ ID NO: 2 of at least 95%, and has substantially the same immunogenic activity as said antigenic peptide of SEQ ID NO: 2, wherein the amino acid residue corresponding to amino acid residue 18 (P-$Tyr_{18}$) of SEQ ID NO: 2 is phosphorylated;

b. to SEQ ID NO: 3 of at least 95%, and has substantially the same immunogenic activity as said antigenic peptide of SEQ ID NO: 3, wherein at least one, particularly at least 2 of amino acid residues corresponding to amino acid residues 212 (P-$Thr_{212}$) and 214 (P-$Ser_{214}$) of SEQ ID NO: 3 are phosphorylated;

c. to SEQ ID NO: 4 of at least 95%, and has substantially the same immunogenic activity as said antigenic peptide of SEQ ID NO: 4, wherein at least one, particularly at least 2 of amino acid residues corresponding to amino acid residues 202 (P-Ser$_{202}$) and 205 (P-Thr$_{205}$) of SEQ ID NO: 4 are phosphorylated;

d. to SEQ ID NO: 5 of at least 95%, and has substantially the same immunogenic activity as said antigenic peptide of SEQ ID NO: 5, wherein at least one, but especially all of amino acid residues corresponding to amino acid residues 396 (P-Ser$_{396}$) and 404 (P-Ser$_{404}$) of SEQ ID NO: 5 are phosphorylated;

e. to SEQ ID NO: 6 of at least 95%, and has substantially the same immunogenic activity as said antigenic peptide of SEQ ID NO: 6, wherein at least one, but especially all of amino acid residues corresponding to amino acid residues 404 (P-Ser$_{404}$) and 409 (P-Ser$_{409}$) of SEQ ID NO: 6 are phosphorylated; or f. to SEQ ID NO: 7 of at least 95%, and has substantially the same immunogenic activity as said antigenic peptide of SEQ ID NO: 7, wherein at least one, particularly at least 2, particularly a least 3, but especially all of amino acid residues corresponding to amino acid residues 202 (P-Ser$_{202}$), 205 (P-Thr$_{205}$), 212 (P-Thr$_{212}$), and 214 (P-Ser$_{214}$) of SEQ ID NO: 7 are phosphorylated.

g. to SEQ ID NO 8: of at least 95%, and has substantially the same immunogenic activity as said antigenic peptide of SEQ ID NO: 8, wherein at least one, but especially all of amino acid residues corresponding to amino acid residue 409 (P-Ser$_{409}$) of SEQ ID NO: 8 is phosphorylated;

h. to SEQ ID NO: 9 of at least 95%, and has substantially the same immunogenic activity as said antigenic peptide of SEQ ID NO: 9, wherein at least one, but especially all of amino acid residues corresponding to amino acid residue 404 (P-Ser$_{404}$) of SEQ ID NO: 9 is phosphorylated; or In one embodiment, said peptide derived from a human tau protein has an amino acid sequence of SEQ ID NO: 2; SEQ ID NO: 3; SEQ ID NO: 4; SEQ ID NO: 5; SEQ ID NO: 6; SEQ ID NO: 7; SEQ ID NO:8 or SEQ ID NO 9.

In one embodiment of the invention, the extent of β-sheet structures within the method according to the invention and as described herein is determined by CD spectroscopy.

In one embodiment of the invention, the extent of β-sheet aggregation within the method according to the invention and as described herein is determined by ThT fluorescence.

In one embodiment of the invention, the extent of β-sheet structures and/or β-sheet aggregation of the liposome-bound antigenic peptides is compared within the method according to the invention and as described herein with that of a free antigenic peptide; and/or liposome bound liposomal peptide; and/or any known peptide and/or protein with β-sheet structure, particularly with a palmitoylated Abeta 1-15 fragment, particularly ACI-24, as disclosed in WO 2007/068411.

In one embodiment, the present invention relates to an immunogenic construct comprising a peptide molecule anchored into the membrane of a liposome via a hydrophobic moiety prepared by any of the methods of the invention, or by a combination of said methods, as disclosed herein. In particular, said immunogenic construct is modulated to have an increased extent of β-sheet structure and/or β-sheet aggregation, particularly of between 50%-100%, more particularly of between 80-100% as compared with the extent of β-sheet structure and/or β-sheet aggregation of a free antigenic peptide; and/or liposome bound liposomal peptide; and/or any known peptide and/or protein with β-sheet structure, particularly with a palmitoylated Abeta 1-15 fragment, particularly ACI-24, as disclosed in WO 2007/068411.

In one embodiment, the present invention relates to an immunogenic construct comprising a peptide molecule anchored into the membrane of a liposome via hydrophobic moieties, wherein said hydrophobic moieties are covalently bound to the N- and/or the C-terminus of the peptide molecule such that there is a disparity in the number of hydrophobic moieties between the N- and the C-terminus. In particular, the number of hydrophobic moieties covalently bound to the N-terminus of the peptide molecule exceeds the number of hydrophobic moieties covalently bound to the C-terminus of the peptide molecule by at least one, at least two, at least three, at least four moieties, or, vice versa, the number of hydrophobic moieties covalently bound to the C-terminus of the peptide molecule exceeds the number of hydrophobic moieties covalently bound to the N-terminus of the peptide molecule by at least one, at least two, at least three, at least four moieties.

In one embodiment, the present invention relates to an immunogenic construct comprising a peptide molecule anchored into the membrane of a liposome via hydrophobic moieties, wherein the ratio of the hydrophobic moieties covalently bound to the N-terminus and the C-terminus of the peptide molecule and to the C-terminus and N-terminus, respectively, is 2:1; particularly 3:1, particularly 3:2, particularly 4:2, but especially 4:1.

In one embodiment, the invention provides an immunogenic construct, wherein at least 4 hydrophobic moieties are covalently bound to the N-terminus of the peptide molecule and one hydrophobic moiety is bound to the C-terminus of the peptide molecule.

In one embodiment, the invention provides an immunogenic construct, wherein at least 4 hydrophobic moieties are covalently bound to the C-terminus of the peptide molecule and one hydrophobic moiety is bound to the N-terminus of the peptide molecule.

In one embodiment the present invention relates to a an immunogenic construct according to the invention and as described herein comprising a peptide molecule anchored into the membrane of a liposome via a hydrophobic moiety, particularly a fatty acid, a triglyceride, diglyceride, steroid, sphingolipid, glycolipid or a phospholipid, particularly a fatty acid, particularly an alkyl group or a fatty acid with a carbon backbone of at least 1 carbon atom, particularly at least 2 carbon atoms, particularly at least 3 carbon atoms, particularly at least 4 carbon atoms, particularly at least 6 carbon atoms, particularly at least 8 carbon atoms, particularly at least 12 carbon atoms, particularly a palmitic acid, covalently bound to the C- and/or N-terminal part of the peptide molecule prepared by a method according to the present invention and as disclosed herein.

In one embodiment the present invention relates to a an immunogenic construct according to the invention and as described herein comprising a peptide molecule anchored into the membrane of a liposome via a hydrophobic moiety, particularly a fatty acid, a triglyceride, diglyceride, steroid, sphingolipid, glycolipid or a phospholipid, particularly a fatty acid, particularly an alkyl group or a fatty acid with a carbon backbone of 1 carbon atom, particularly 2 carbon atoms, particularly 3 carbon atoms, particularly 4 carbon atoms, particularly 6 carbon atoms, particularly 8 carbon atoms, particularly 12 carbon atoms, particularly a palmitic acid, covalently bound to the C- and/or N-terminal part of the peptide molecule prepared by a method according to the present invention and as disclosed herein.

In particular, the present invention relates to a composition comprising an immunogenic construct according to the invention and as described herein comprising a peptide molecule anchored into the membrane of a liposome via a hydrophobic moiety, particularly an alkyl group or a fatty acid, a triglyceride, diglyceride, steroid, sphingolipid, glycolipid or a phospholipid, particularly a fatty acid, particularly a fatty acid with a carbon backbone of at least 6 carbon atoms, particularly a palmitic acid, covalently bound to the C- and/or N-terminal part of the peptide molecule prepared by a method according to the present invention and as disclosed herein.

In a specific embodiment, the immunogenic construct according to the invention as described herein or the composition comprising said peptide molecule is free or substantially free of metal ions.

In one embodiment, the present invention relates to a composition comprising an immunogenic construct comprising a peptide molecule anchored into the membrane of a liposome via a hydrophobic moiety prepared by a method according to the present invention and as disclosed herein, which composition comprises a metal chelating agent.

In one embodiment, a composition according to the invention and as described herein is provided containing one or more compounds which are capable of enhancing the formation of β-sheet aggregates, in particular one or more compounds selected from the group consisting of heparin, myo-inositol, glycogen and ellagic acid.

In one embodiment, an immunogenic construct comprising a liposome-embedded peptide, or a composition comprising said immunogenic construct according to the invention and as described herein is provided, wherein said immunogenic construct has an increased net negative surface potential due to an increased proportion of anionic lipids in the lipid bilayer of the liposome. In particular, said anionic lipids are selected from the group consisting of:
 i. diacyl-phospholipids with headgroups phosphatidyl glycerol, phosphatidyl serine, phosphatidyl inositol, L-α-phosphatidylinositol-4-phosphate or phosphatidic acid;
 ii. diether-phospholipids with headgroups phosphatidyl glycerol, phosphatidyl serine, phosphatidyl inositol, L-α-phosphatidylinositol-4-phosphate or phosphatidic acid;
 iii. lyso-phospholipids with headgroups phosphatidyl glycerol, phosphatidyl serine or phosphatidic acid, and
 iv. cardiolipin, dilyso-cardiolipin, monolyso-cardiolipin.
 v. glycolipids or lipopolysaccharides In one embodiment, an immunogenic construct comprising a liposome-embedded peptide, or a composition comprising said immunogenic construct according to the invention and as described herein is provided wherein the liposomes have a net negative surface potential of at least <0 mV, particularly of at least <−10 mV, particularly of at least <−40 mV, in PBS.

In one embodiment, the present invention relates to an immunogenic construct comprising a liposome-embedded peptide, or a composition comprising said immunogenic construct as described herein, wherein the surface potential is in a range of between 0 mV and −12 mV, particularly in a range of −2 mV to −10 mV, particularly in a range of −2 mV to −8 mV or in a range of −16 mV to −40 mV, particularly between −15 mV to −30 mV, particularly between −20 mV to −35 mV.

In one embodiment, an immunogenic construct comprising a liposome-embedded peptide, or a composition comprising said immunogenic construct according to the invention and as described herein is provided wherein the liposomes have a net negative surface potential of at least >0 mV, particularly of at least >+10 mV, particularly of at least >+35 mV, in PBS.

The liposome surface potential (zeta potential) of the liposome is determined as described in Examples (Part I, C2).

In one embodiment, the present invention relates to an immunogenic construct comprising a liposome-embedded peptide, or a composition comprising said immunogenic construct according to the invention and as described herein incorporating one or more of the above described features, In one embodiment, the present invention provides an immunogenic construct comprising a liposome-embedded peptide, or a composition comprising said immunogenic construct according to the invention and as described herein, wherein (a) said hydrophobic moieties are covalently bound to the N- and/or the C-terminus of the peptide molecule such that there is a disparity in the number of hydrophobic moieties between the N- and the C-terminus and (b) which construct or composition is free or substantially free of metal ions; i.e. due to the presence of a metal chelating agent; and/or (c) has an increased net negative surface potential, i.e., due to an increased proportion of anionic lipids in the lipid bilayer of the liposome; and/or (d) has a hydrophobic anchor comprising between at least 4 and at least 16 carbon atoms; and/or (e) contains one or more compounds which are capable of enhancing the formation of β-sheet aggregates.

In one embodiment, the present invention provides an immunogenic construct comprising a liposome-embedded peptide, or a composition comprising said immunogenic construct according to the invention and as described herein, which construct or composition is (b) free or substantially free of metal ions; i.e. due to the presence of a metal chelating agent; and/or (c) has an increased net negative surface potential, i.e., due to an increased proportion of anionic lipids in the lipid bilayer of the liposome; and/or (d) has a hydrophobic anchor comprising between at least 4 and at least 16 carbon atoms; and/or (e) contains one or more compounds which are capable of enhancing the formation of β-sheet aggregates.

In one embodiment, the present invention provides an immunogenic construct comprising a liposome-embedded peptide, or a composition comprising said immunogenic construct according to the invention and as described herein, which construct or composition (c) has an increased net negative surface potential, i.e., due to an increased proportion of anionic lipids in the lipid bilayer of the liposome; and/or (d) has a hydrophobic anchor comprising between at least 4 and at least 16 carbon atoms; and/or (e) contains one or more compounds which are capable of enhancing the formation of β-sheet aggregates.

In one embodiment, the present invention provides an immunogenic construct comprising a liposome-embedded peptide, or a composition comprising said immunogenic construct according to the invention and as described herein, which construct or composition (d) has a hydrophobic anchor comprising between at least 4 and at least 16 carbon atoms; and (e) contains one or more compounds which are capable of enhancing the formation of β-sheet aggregates.

In one embodiment, the present invention relates to an immunogenic construct comprising a peptide molecule anchored into the membrane of a liposome via a hydrophobic moiety prepared by any of the methods of the invention, or by a combination of said methods, as disclosed herein, wherein said immunogenic construct is modulated to have an decreased extent of β-sheet structure and/or β-sheet aggregation.

In one embodiment, an immunogenic construct comprising a liposome-embedded peptide, or a composition comprising said immunogenic construct according to the invention and as described herein is provided containing a small molecule capable of disaggregating β-sheet aggregates, particularly a small molecule selected from the group consisting of tannic acid, rosmarinic acid, methylene blue, scyllo-cyclohexanehexyl, scyllo-inositol, (+)-catechin, 4,5-dianilinophthalimide, dopamine, L-dopa, rifampicin, 4'-iodo-4'-deoxydoxorubicin, nordihydroguaretic acid, curcumin, 3-amino-1-propanesulfonic acid, piceid, nicotine, myricetin, morin, quercetin, kaempferol, (+)-catechin (−)-epicatechin, gallic acid, epicatechin gallate, epigallocatechin gallate, porphyrin phthalocyanine, rifampicin, tetracycline, curcumin, ferulic acid, estriol, vitamin A, beta-carotene, coenzyme Q10, ibuprofen, aspirin, acetaminophen, meclofenamic acid, sulindac sulfide, ketoprofen, flurbiprofen, diclofenac, naproxen, indomethacin, selegiline, pergolide and bromocriptine.

Further molecules that can be used within the present invention for disaggregating β-sheet aggregates are disclosed in international application published as WO/2008/061795 and WO/2008/061796, respectively, the disclosure of which is incorporated herein in its entirety.

In one embodiment, an immunogenic construct comprising a liposome-embedded peptide, or a composition comprising said immunogenic construct according to the invention and as described herein is provided containing one or more metal ions which are capable of disrupting peptide-liposome or peptide-peptide stabilizing interactions, particularly Cu(II) and/or Zn(II).

In one embodiment, an immunogenic construct comprising a liposome-embedded peptide, or a composition comprising said immunogenic construct according to the invention and as described herein is provided, wherein the peptide molecule is a peptide derived from an amyloid protein or amyloid-like protein such as, for example prion protein, tau protein, alpha-synuclein, huntingtin.

In particular, the peptide molecule is an Aβ peptide derived from the N-terminus of an amyloid protein or amyloid-like protein, particularly an Aβ peptide and/or truncated Aβ fragment longer than 5 amino acids; 5 and 16 amino acids; 6 and 12 amino acids; or 4 and 9 amino acids. particularly an $A\beta_{1-30}$; an $A\beta_{1-20}$; an $A\beta_{1-16}$; an $A\beta_{1-15}$; or an $A\beta_{1-9}$.

In one embodiment, the peptide molecule is a peptide derived from a tau protein, particularly a human tau protein, particularly a molecule comprising a phospho-peptide mimicking a major pathological phospho-epitope of protein tau.

In one embodiment, the present invention relates to a method of producing a conformation specific antibody or a conformation specific antibody fragment by administering to an animal or a human an immunogenic construct comprising a liposome-embedded peptide, or a composition comprising said immunogenic construct according to the invention and as described herein, particularly an immunogenic construct comprising an Aβ peptide derived from the N-terminus of an amyloid protein or amyloid-like protein, particularly an Aβ peptide and/or truncated Aβ fragment longer than 5 amino acids, 5 and 16 amino acids; 6 and 12 amino acids; or 4 and 9 amino acids, particularly an $A\beta_{1-30}$; an $A\beta_{1-20}$; an $A\beta_{1-16}$; an $A\beta_{1-15}$; or an $A\beta_{1-9}$. or an immunogenic construct comprising a peptide derived from a tau protein, particularly a human tau protein, particularly a molecule comprising a phospho-peptide mimicking a major pathological phospho-epitope of protein tau, such that an immune response is triggered or induced in said animal or human and an antibody produced, and obtaining said antibody. Said antibody or antibody fragment may be a polyclonal antibody or fragment thereof or a monoclonal antibody or fragment thereof.

In one embodiment, the present invention relates to a conformation specific antibody or a conformation specific antibody fragment produced by a method of the invention, particularly a polyclonal antibody or fragment thereof or a monoclonal antibody or fragment thereof.

In a specific embodiment, the antibody of the invention is a conformation specific antibody or a conformation specific antibody fragment capable of specifically recognizing pathological peptide conformations or peptide aggregates comprising peptides exhibiting such pathological conformations, particularly pathological β-sheet multimers of a target peptide and showing no or substantially no cross-reactivity with the physiologically active, "healthy" peptide conformer.

Also comprised within the present invention are antibodies which are functionally equivalent to the antibodies of the invention and may be obtained by modification of said antibodies of the invention.

The present invention further relates to a pharmaceutical composition comprising an immunogenic construct or a conformation specific antibody or a conformation specific antibody fragment according to the invention and as described herein in a therapeutically effective amount together with a pharmaceutically acceptable excipient or carrier.

In particular, the present invention relates to a pharmaceutical composition comprising a therapeutically effective amount of an immunogenic construct comprising a peptide molecule with a modulated secondary and/or quaternary structure anchored into the membrane of a liposome via a hydrophobic moiety covalently bound to the C- and/or N-terminal part of the peptide molecule, wherein said immunogenic construct is produced by a method of the present invention as described herein, or a composition comprising said immunogenic construct of the invention as described herein, together with a pharmaceutically acceptable excipient or carrier.

The pharmaceutical compositions of the present invention may thus comprise a therapeutically effective amount of an immunogenic construct comprising a peptide molecule with a modulated secondary and/or quaternary structure anchored into the membrane of a liposome made by reconstituting liposomes in the presence of purified or partially purified or modified antigenic peptides according to the invention and as described herein. Additionally, peptide fragments may be reconstituted into liposomes. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, non-ionic block polymers, aluminum hydroxide or aluminum phosphate adjuvant, and mixtures thereof.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., *Infect. Immun.* 60:2438-2444, 1992, hereby incorporated by reference. The liposome can optionally contain an adjuvant or and immunomodulator or both. A preferred immunomodulator is lipid A, particularly a detoxified lipid A such as, for example, monophosphoryl or diphosphoryl lipid A. Liposomes may be prepared by the crossflow injection technique as described, for example, in Wagner et al (2002) Journal of Liposome Research Vol 12(3), pp 259-270. During the injection of lipid solutions into an aqueous buffer system, lipids tend to form "precipitates", followed by self arrangement in vesicles. The obtained vesicle size depends on factors such as lipid concentration, stirring rate, injection rate, and the choice of lipids. The preparation system may consist of a crossflow injection module, vessels for the polar phase (e.g. a PBS buffer solution), an ethanol/lipid solution vessel and a pressure device, but particularly a nitrogen pressure device. While the aqueous or polar solution is pumped through the crossflow injection module the ethanol/lipid solution is injected into the polar phase with varying pressures applied.

In one embodiment, the modified antigenic peptide according to the invention and as described herein may thus be further modified by reconstitution into liposomes consisting of phospholipids (phosphatidylcholine and phosphatidyl glycerol) and cholesterol in varied molar ratios. Other phospholipids can be used. Lipid A is used at a concentration of approximately 40 µg/pmole of phospholipids.

The liposome may have a dual function in that it can be used as a carrier comprising the antigenic construct as described herein before and, at the same time, function as an adjuvant to increase or stimulate the immune response within the target animal or human to be treated with the therapeutic vaccine according to the invention. Optionally, the liposome may, in addition, contain a further adjuvant or and immunomodulator or both such as, for example, lipid A, alum, calcium phosphate, interleukin 1, and/or microcapsules of polysaccharides and proteins, but particularly a lipid A, more particularly a detoxified lipid A, such as monophosphoryl or diphosphoryl lipid A, or alum.

In a specific embodiment of the invention liposomes with lipid A are used as adjuvant to prepare the pharmaceutical composition of the invention. Dimyristoylphosphatidyl-choline, -glycerol and -cholesterol are mixed, particularly in a molar ratio of 9:1:7. A strong immunmodulator such as, for example, monophosphoryl lipid A is then added at a suitable concentration, particularly at a concentration of between 5 mg and 50 mg per mmol, particularly between 20 mg and 50 mg per mmol, more particularly at a concentration of between 30 mg and 40 mg per mmol of phospholipids. The modified antigenic peptide is then added at a molar ratio peptide to phospholipids of between 1:30 and 1:200, particularly at a molar ratio of between 1:50 and 1:120, more particularly of 1:100. Solvents are removed, for example through evaporation, and the resulting film hydrated with sterile buffer solution such as, for example PBS.

In particular, the present invention relates to a pharmaceutical composition comprising a therapeutically effective amount of a conformation specific antibody or a conformation specific antibody fragment prepared by a method according to the invention involving the use of a peptide molecule with a modulated secondary and/or quaternary structure anchored into the membrane of a liposome via a hydrophobic moiety covalently bound to the C- and/or N-terminal part of the peptide molecule, wherein said immunogenic construct is produced by a method of the present invention and as described herein, together with a pharmaceutically acceptable excipient or carrier.

In one embodiment, the invention relates to a pharmaceutical composition comprising a therapeutically effective amount of a conformation specific antibody or a conformation specific antibody fragment prepared by a method according to the invention, wherein said antibody or antibody fragment is capable of specifically recognizing pathological peptide aggregates or mulitmers, particularly pathological β-sheet aggregates or multimers of a target peptide and showing no or substantially no cross-reactivity with the physiologically active, healthy peptide conformer.

In one embodiment, the present invention relates to the pharmaceutical composition as described herein for treating or preventing in an animal or a human patient in need of such a treatment a disease or disorder associated with the aggregation of peptides, particularly peptides associated to cell membranes, particularly proteopathies, diseases involving protein misfolding and/or diseases involving protein accumulation.

In a specific aspect, the present invention relates to the pharmaceutical composition as described herein for treating or preventing in a subject, particularly in an animal or a human patient in need of such a treatment a disease or disorder selected from the group consisting of AA amyloidosis, Age-related macular degeneration (AMD), AH (heavy chain) amyloidosis, AL (light chain) amyloidosis, Alexander disease, Alzheimer's disease, Amyotrophic lateral sclerosis, Aortic medial amyloidosis, apoA1 amyloidosis, apoA2 amyloidosis, apoA4 amyloidosis, Argyrophilic grain dementia, CADASIL, Cardiac atrial amyloidosis, Cataract, Cerebral amyloid angiopathy, Corneal lactoferrin amyloidosis, Corticobasal degeneration, Creutzfeldt-Jacob disease, Critical illness myopathy, Cutaneous lichen amyloidosis, Cystic fibrosis, Dementia pugilistica, Dialysis amyloidosis, Diffuse neurofibrillarly tangles with calcification, Down's Syndrome, Endocrine tumors, Familial amyloidotic neuropathy, Familial British dementia, Familial Danish dementia, Familial visceral amyloidosis, Fibrinogen amyloidosis, Finnish hereditary amyloidosis, frontotemporal lobar dementia, Gerstmann-Sträussler-Scheinker disease, Glaucoma, Guam Parkinson-Dementia complex, Hallevorden-Spatz disease, Hereditary cerebral hemorrhage with amyloidosis—Dutch type, Hereditary cerebral hemorrhage with amyloidosis—Icelandic type, HIV-related dementia, Huntington's disease and other triplet disorders, Hereditary lattice corneal dystrophy, Inclusion body myositis/myopathy, Lattice dystrophy, Lewy body dementia (LBD), Lysozyme amyloidosis, Mallory bodies, Medullary thyroid carcinoma, Mild cognitive impairment (MCI), Multiple system atrophy, Myotonic dystrophy, Niemann-Pick disease type C, Non-Guamanian motor neuron disease with neurofibrillary tangles, Ocular amyloidosis, Odontogenic (Pindborg) tumor amyloid, Optic nerve drusen, Optic neuropathy, Parkinson's disease, Pallido-ponto-nigral degeneration, Pick's disease, Pituitary prolactinoma, Postencephalitic Parkinsonism, Primary systemic amyloidosis, Primary cutaneous amyloidosis, Primary retinal degeneration, prion disease, Prion protein cerebral amyloid angiopathy, Progressive subcortical gliosis, Progressive supranuclear palsy, Pulmonary alveolar proteinosis, Seminal vesicle amyloid, seipinopathy, Senile systemic amyloidosis, Serpinopathy, Sickle cell disease, Subacute sclerosing panencephalitis, Synucleinopathies, Tangle only dementia, Tauopathies, Traumatic brain injury and Type 2 diabetes.

In one embodiment, the present invention relates to a method for treating or preventing a disease or disorder associated with the aggregation of peptides, particularly peptides associated to cell membranes, particularly proteopathies, diseases involving protein misfolding and/or diseases involving protein accumulation comprising administering to a subject, particularly an animal or human patient in need of such a treatment an immunogenic construct; an antibody or a pharmaceutical composition according to the invention and as described herein in a therapeutically effective amount.

In a specific aspect of the invention, the treatment or prevention of a disease or disorder selected from the group consisting of AA amyloidosis, Age-related macular degeneration (AMD), AH (heavy chain) amyloidosis, AL (light chain) amyloidosis, Alexander disease, Alzheimer's disease, Amyotrophic lateral sclerosis, Aortic medial amyloidosis, apoA1 amyloidosis, apoA2 amyloidosis, apoA4 amyloidosis, Argyrophilic grain dementia, CADASIL, Cardiac atrial amyloidosis, Cataract, Cerebral amyloid angiopathy, Corneal lactoferrin amyloidosis, Corticobasal degeneration, Creutzfeldt-Jacob disease, Critical illness myopathy, Cutaneous lichen amyloidosis, Cystic fibrosis, Dementia pugilistica, Dialysis amyloidosis, Diffuse neurofibrillarly tangles with calcification, Down's Syndrome, Endocrine tumors, Familial amyloidotic neuropathy, Familial British dementia, Familial Danish dementia, Familial visceral amyloidosis, Fibrinogen amyloidosis, Finnish hereditary amyloidosis, frontotemporal lobar dementia, Gerstmann-Sträussler-Scheinker disease, Glaucoma, Guam Parkinson-Dementia complex, Halievorden-Spatz disease, Hereditary cerebral hemorrhage with amyloidosis—Dutch type, Hereditary cerebral hemorrhage with amyloidosis—Icelandic type, HIV-related dementia, Huntington's disease and other triplet disorders, Hereditary lattice corneal dystrophy, Inclusion body myositis/myopathy, Lattice dystrophy, Lewy body dementia (LBD), Lysozyme amyloidosis, Mallory bodies, Medullary thyroid carcinoma, Mild cognitive impairment (MCI), Multiple system atrophy, Myotonic dystrophy, Niemann-Pick disease type C, Non-Guamanian motor neuron disease with neurofibrillary tangles, Ocular amyloidosis, Odontogenic (Pindborg) tumor amyloid, Optic nerve drusen, Optic neuropathy, Parkinson's disease, Pallido-ponto-nigral degeneration, Pick's disease, Pituitary prolactinoma, Postencephalitic Parkinsonism, Primary systemic amyloidosis, Primary cutaneous amyloidosis, Primary retinal degeneration, prion disease, Prion protein cerebral amyloid angiopathy, Progressive subcortical gliosis, Progressive supranuclear palsy, Pulmonary alveolar proteinosis, Seminal vesicle amyloid, seipinopathy, Senile systemic amyloidosis, Serpinopathy, Sickle cell disease, Subacute sclerosing panencephalitis, Synucleinopathies, Tangle only dementia, Tauopathies, Traumatic brain injury and Type 2 diabetes is contemplated comprising administering to a subject, particularly an animal or a human patient in need of such a treatment a an immunogenic construct; an antibody or a pharmaceutical composition according to the invention and as described herein.

In one embodiment, the invention relates to a method of obtaining compounds capable of interfering with the secondary and/or quaternary structure of peptides, particularly peptides associated to cell membranes, comprising a. contacting the compound to be tested with an immunogenic construct comprising a peptide molecule anchored into the membrane of a liposome via a hydrophobic moiety covalently bound to the C- and/or N-terminal part of the peptide molecule according to the invention and as described herein;

b. determining the extent of β-sheet structure and/or β-sheet aggregation of the membrane anchored peptide molecules before and after contact with the test compound;

c. calculating the β-sheet disaggregation or aggregation enhancing activity of the test compound; and d. obtaining the test compound with the desired activity.

In one aspect of the invention, it is contemplated to determine the extent of β-sheet structure and/or β-sheet aggregation of the membrane anchored peptide molecule by CD spectroscopy and by measuring fluorescence of Thioflavin T (ThT), respectively, upon addition of the liposome anchored peptide molecule.

In one embodiment, the present invention relates to a compound obtained by such a method, particularly a compound which is capable of increasing or decreasing the aggregation of peptides, particularly peptides associated to cell membranes.

In still another embodiment, the invention relates to a method for treating or preventing a disease or disorder associated with the aggregation of peptides, particularly peptides associated to cell membranes, particularly proteopathies, diseases involving protein misfolding and/or diseases involving protein accumulation comprising administering to a subject, particularly an animal or a human patient in need of such a treatment a compound obtained by a method according to the invention as described herein in a therapeutically effective amount.

In a specific aspect of the invention, the treatment or prevention of a disease or disorder selected from the group consisting of AA amyloidosis, Age-related macular degeneration (AMD), AH (heavy chain) amyloidosis, AL (light chain) amyloidosis, Alexander disease, Alzheimer's disease, Amyotrophic lateral sclerosis, Aortic medial amyloidosis, apoA1 amyloidosis, apoA2 amyloidosis, apoA4 amyloidosis, Argyrophilic grain dementia, CADASIL, Cardiac atrial amyloidosis, Cataract, Cerebral amyloid angiopathy, Corneal lactoferrin amyloidosis, Corticobasal degeneration, Creutzfeldt-Jacob disease, Critical illness myopathy, Cutaneous lichen amyloidosis, Cystic fibrosis, Dementia pugilistica, Dialysis amyloidosis, Diffuse neurofibrillarly tangles with calcification, Down's Syndrome, Endocrine tumors, Familial amyloidotic neuropathy, Familial British dementia, Familial Danish dementia, Familial visceral amyloidosis, Fibrinogen amyloidosis, Finnish hereditary amyloidosis, frontotemporal lobar dementia, Gerstmann-Sträussler-Scheinker disease, Glaucoma, Guam Parkinson-Dementia complex, Hallevorden-Spatz disease, Hereditary cerebral hemorrhage with amyloidosis—Dutch type, Hereditary cerebral hemorrhage with amyloidosis—Icelandic type, HIV-related dementia, Huntington's disease and other triplet disorders, Hereditary lattice corneal dystrophy, Inclusion body myositis/myopathy, Lattice dystrophy, Lewy body dementia (LBD), Lysozyme amyloidosis, Mallory bodies, Medullary thyroid carcinoma, Mild cognitive impairment (MCI), Multiple system atrophy, Myotonic dystrophy, Niemann-Pick disease type C, Non-Guamanian motor neuron disease with neurofibrillary tangles, Ocular amyloidosis, Odontogenic (Pindborg) tumor amyloid, Optic nerve drusen, Optic neuropathy, Parkinson's disease, Pallido-ponto-nigral degeneration, Pick's disease, Pituitary prolactinoma, Postencephalitic Parkinsonism, Primary systemic amyloidosis, Primary cutaneous amyloidosis, Primary retinal degeneration, prion disease, Prion protein cerebral amyloid angiopathy, Progressive subcortical gliosis, Progressive supranuclear palsy, Pulmonary alveolar proteinosis, Seminal vesicle amyloid, seipinopathy, Senile systemic amyloidosis, Serpinopathy, Sickle cell disease, Subacute sclerosing panencephalitis, Synucleinopathies, Tangle only dementia, Tauopathies, Traumatic brain injury and Type 2 diabetes, is contemplated.

Formulation of the pharmaceutical composition according to the invention can be accomplished according to standard methodology known to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine,
isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and 7-secretase inhibitors, tau proteins, neurotransmitter, □-sheet breakers, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, cholin, *Ginkgo biloba*, acyetyl-L-carnitine, idebenone, propentofylline, or a xanthine derivative, together with an antibody according to the present invention and, optionally, a pharmaceutically acceptable carrier and/or a diluent and/or an excipient and instructions for the treatment of diseases.

The pharmaceutically active ingredient may be present in amounts between 1 µg and 10 mg per dose. Generally, the regime of administration should be in the range of between 0.1 µg and 10 mg of active ingredient, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parenterally, e.g. intravenously. Preparations for parenteral administration include sterile aqueous or non-aqueous solutions, suspensions and emulsions. Non-aqueous solvents include, without being limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the antibody or active fragment thereof or the compounds capable of interfering with the secondary and/or quaternary structure of peptides obtained by a method as described herein, to traverse the blood-brain barrier. Certain neurodegenerative diseases are associated with an increase in permeability of the blood-brain barrier, such that the antibody or active fragment thereof, or the compounds according to the invention, can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or active fragment thereof, or the compounds according to the invention, across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9; 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268, 164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or active fragment thereof, or the compounds according to the invention, across the blood-brain barrier include, but are not limited to, encapsulating the antibody or active fragment thereof, or the compounds according to the invention, in liposomes that are coupled to active fragments thereof that bind to receptors on the vascular endothelium of the blood-brain barrier (see, e.g., U.S. Patent Application Publication No. 20020025313), and coating the antibody or active fragment thereof, or the compounds according to the invention, in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or active fragment thereof, or the compounds according to the invention, across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/007713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

In still another aspect of the invention a method for diagnosing a disease or disorder involving protein misfolding and/or diseases involving protein accumulation in a subject is contemplated comprising detecting the immunospecific binding of an antibody according to the invention and as described herein or functional parts thereof, to an epitope of said disease-causing peptide or protein in a sample of a subject, particularly a mammal, particularly a human, or in situ which includes the steps of
   a. bringing the sample or a specific body part or body area suspected to contain the disease-causing peptide or protein into contact with the antibody which antibody binds an epitope of the disease-causing peptide or protein;
   b. allowing the antibody to bind to the disease-causing peptide or protein to form an immunological complex;
   c. detecting the formation of the immunological complex, particularly such that presence or absence of the immunological complex correlates with presence or absence of the disease-causing peptide or protein; and
   d. correlating the presence or absence of the immunological complex with the presence or absence of the disease-causing peptide or protein in the sample.

The invention further contemplates a method for diagnosing a predisposition to a disease or disorder involving protein misfolding and/or diseases involving protein accumulation in a subject comprising detecting the immunospecific binding of an antibody according to the invention and as described herein or functional parts thereof, to an epitope of said disease-causing peptide or protein in a sample of a subject, particularly a mammal, particularly a human, or in situ which includes the steps of
   a. bringing the sample or a specific body part or body area suspected to contain the disease-causing peptide or protein into contact with the antibody which antibody binds an epitope of the disease-causing peptide or protein;
   b. allowing the antibody to bind to the disease-causing peptide or protein to form an immunological complex;
   c. detecting the formation of the immunological complex,
   d. correlating the presence or absence of the immunological complex with the presence or absence of the disease-causing peptide or protein in the sample; and
   e. comparing the amount of said immunological complex to a normal control value,
wherein an increase in the amount of said complex compared to a normal control value indicates that the subject is suffering from or is at risk of developing a disease or disorder involving protein misfolding and/or diseases involving protein accumulation In another embodiment of the invention, a method for monitoring minimal residual disease or disorder involving protein misfolding and/or diseases involving protein accumulation following treatment of a subject, particularly a mammal, particularly a human, with the pharmaceutical according to the invention and as described herein is provided, wherein said method comprises:
   a. bringing the sample or a specific body part or body area suspected to contain the disease-causing peptide or protein into contact with the antibody according to the invention and as described herein or functional parts thereof, which antibody or functional part binds an epitope of the disease-causing peptide or protein;
   b. allowing the antibody to bind to the disease-causing peptide or protein to form an immunological complex;
   c. detecting the formation of the immunological complex,
   d. correlating the presence or absence of the immunological complex with the presence or absence of the disease-causing peptide or protein in the sample; and
   e. comparing the amount of said immunological complex to a normal control value,
wherein an increase in the amount of said complex compared to a normal control value indicates that the subject still suffers from a minimal residual disease or disorder involving protein misfolding and/or diseases involving protein accumulation.

In still another embodiment, the invention provides a method for predicting responsiveness of a subject, particularly a mammal, particularly a human, being treated with the pharmaceutical composition according to the invention and as described herein, wherein said method comprises:
   a. bringing the sample or a specific body part or body area suspected to contain the disease-causing peptide or protein into contact with the antibody according to the invention and as described herein or functional parts thereof, which antibody or functional part binds an epitope of the disease-causing peptide or protein;
   b. allowing the antibody to bind to the disease-causing peptide or protein to form an immunological complex;
   c. detecting the formation of the immunological complex,
   d. correlating the presence or absence of the immunological complex with the presence or absence of the disease-causing peptide or protein in the sample; and
   e. comparing the amount of said immunological complex to a normal control value,
wherein a decrease in the amount of said immunological complex indicates that the subject has a high potential of being responsive to the treatment.

The present invention discloses and claims methods of preparing immunogenic constructs comprising a peptide molecule and a hydrophobic moiety covalently bound to the C- and/or N-terminal part of the peptide molecule, which peptide molecule is anchored into the lipid membrane of a liposomal carrier via said hydrophobic moiety for generating an improved conformation specific immune response and/or for producing improved conformation specific antibodies. Peptide N- or C-terminal lipidation is a widely used approach to embed peptides into liposome bilayers. It has previously been reported that incorporating a range of peptides conjugated at both the N- and C-termini with two palmitoyl chains, into liposomes composed of phospholipids (DMPC and DMPG), cholesterol and MPLA rapidly induced high IgG titers in mice.

It is attempted to extend these observations to determine the rules which govern the conformational transitions of lipopeptides embedded within lipid bilayers and to translate these rules into a protocol for designing a peptide molecule exhibiting a predefined secondary and/or quaternary conformation, capable of generating a more targeted and improved structure or conformation specific immune response.

The forces which drive the self-assembly of the liposomal lipopeptides can be accredited to a combination of hydrophobic interactions between hydrophobic anchors and interactions between peptide backbone and liposome surface. Development of strategies disclosed and claimed in the present application to modulate these interactions thus extends the repertoire of available methods to alter the aggregation of lipopeptide immunogens within liposome bilayers.

Within the present invention the properties and mechanism of formation of the β-sheet aggregates formed by liposomal peptides are disclosed.

In one aspect, it is shown how preformed peptide aggregates can undergo disassembly within the lipid bilayers of the liposome.

In particular, it is demonstrated that metal ions such as, for example, Cu(II); Zn(II) or Fe(III) can rapidly disaggregate liposomal peptide aggregates.

Re-aggregation of the liposomal peptide can be achieved upon addition of a metal chelating agent. It thus appears that peptide aggregation occurs within the lipid membrane and that the peptide aggregates are formed as a single thermodynamically stable structure.

Structure-conformation studies with a range of peptides of unrelated primary sequence demonstrated that the amino-acid composition has only a minor influence on the aggregation potential of said peptides. The tested peptides were shown to also form β-sheet aggregates upon integration into liposomes of identical composition independent of their amino acid composition. Therefore β-sheet aggregation can be induced by lipidation of unstructured peptides and incorporation into liposomes even under physiological conditions. Induction of peptide misfolding into β-sheets still occurs for a 9-mer peptide Palm1-9, which highlights the additional negative free folding energy brought by peptide lipidation.

The role of peptide charge in determining the ability to form β-sheet aggregates upon liposomes was examined both by generating a series of mutated peptides, as well as by directly monitoring the binding interactions of the non-lipidated 'native'peptides with liposomes. Both approaches revealed that the amino-acid side-chains have little effect upon aggregation despite the fact that the peptide sequences were chosen in order to have very different isoelectric points. This suggests that it is peptide backbone-liposome interactions that play an important role in determining the peptide secondary and quaternary structure. This model is supported by the results obtained after modulation of peptide aggregation by modification of the liposome surface potential with anionic or cationic lipids. Absence of DMPG or presence of DMTAP in the liposomal membrane leads to a decrease in peptide aggregation. This implies that it is the net surface potential that is responsible for aggregation. While the origin of this effect is not yet fully understood, it may be assumed that anion-H-bond dipole interactions may be responsible.

The number and position of peptide lipidation sites has a dramatic influence upon sheet aggregation. The total number of palmitoyl chains at one end of the peptide molecule correlates well with the extent of β-sheet aggregation, while the total number of lipidation sites poorly correlates. It is therefore concluded that peptide self-assembly is driven by hydrophobic interactions between palmitoyl chains. In particular, lipidation at the C-terminal end with 4 hydrophobic moieties showed the highest tendency to form β-sheet aggregates.

It was further shown within the present invention that also the length of the individual hydrophobic anchor molecule has an influence on the peptide's secondary and/or quaternary structure, Replacing of the N- and C-terminal di-palmitoyl anchors by shorter lipid chains leads to a decrease of the extent of β-sheet aggregation. Thus peptide's secondary and/or quaternary structure can thus also be modulated by varying the length of hydrophobic anchor used.

An alternative strategy to control peptide conformation post-liposome assembly is via the addition of distinct small molecules. It was shown herein that known β-sheet breaker small molecules can disaggregate the β-sheets of liposomal peptides independent of peptide sequence. Accordingly, β-sheet disaggregation can occur not only in solution phase but also within the 2-dimensional plane at the solid-liquid interface. This observation is pertinent following the identification of $A\beta_{1-40/42}$ dimers within lipid rafts of neuronal membranes which were correlated with memory impairment. In this context, liposome-bound peptide systems such as described here may also prove useful as models to screen for and obtain therapeutic compounds capable of interfering with the aggregation of peptides associated to cell membranes.

The present invention thus provides methods and means for increasing the extent of β-sheet structure and/or β-sheet aggregation of an immunogenic construct comprising a peptide molecule and a hydrophobic moiety covalently bound to the C- and/or N-terminal part of the peptide molecule, which peptide molecule is anchored into the lipid membrane of a liposomal carrier via said hydrophobic moiety, by combining one or more of the following measures:

a. increasing the net negative surface potential of the liposome; particularly such that a surface potential of at least <0 mV, particularly to at least <−10 mV, particularly to at least <−40 mV, in PBS, is achieved;
 b. increasing the length of the individual hydrophobic anchor molecule; particularly to a length of at least 6 carbon atoms, particularly at least 12 carbon atoms, particularly at least 14 carbon atoms, particularly at least 18 carbon atoms;
 c. increasing the number of hydrophobic anchor molecules at one end of the peptide molecule; particularly to a total of 1 anchor molecule, particularly to a total of 2 anchor molecules, particularly to a total of 3 anchor molecules, particularly to a total of 4 anchor molecules;
 d. adding of a metal chelating agent.

The liposome surface potential (zeta potential) of the liposome is determined as described in Examples (Part I, C2).

In one embodiment, the present invention relates to an immunogenic construct comprising a peptide molecule and a hydrophobic moiety covalently bound to the C- and/or N-terminal part of the peptide molecule anchored into the lipid membrane of a liposomal carrier via said hydrophobic moiety, which immunogenic construct shows an enhanced extent of β-sheet structure and/or β-sheet aggregation and comprises at east two, particularly at least 3, particularly all of the following features:

a. a net negative surface potential of the liposome of at least <0 mV, particularly of at least <−10 mV, particularly of at least <−40 mV, in PBS;
 b. a length of the individual hydrophobic anchor molecule of at least 6 carbon atoms, particularly at least 12 carbon atoms, particularly at least 14 carbon atoms, particularly at least 18 carbon atoms;
 c. a number of hydrophobic anchor molecules at one end of the peptide molecule totalling 1 anchor molecule, particularly 2 anchor molecules, particularly 3 anchor molecules, particularly 4 anchor molecules;

d. one or more compounds which are capable of stabilising the formation of β-sheet aggregates;
e. no metal ions, particularly due to the presence of a metal chelating agent.

In one embodiment, the present invention relates to an immunogenic construct as described herein, wherein the surface potential is in a range of between 0 mV and −12 mV, particularly in a range of −2 mV to −10 mV, particularly in a range of −2 mV to −8 mV or in a range of −16 mV to −40 mV, particularly between −15 mV to −30 mV, particularly between −20 mV to −35 mV.

The present invention further provides methods and means for decreasing the extent of β-sheet structure and/or β-sheet aggregation of an immunogenic construct comprising a peptide molecule and a hydrophobic moiety covalently bound to the C- and/or N-terminal part of the peptide molecule, which peptide molecule is anchored into the lipid membrane of a liposomal carrier via said hydrophobic moiety, by combining one or more of the following measures:
  a. decreasing the net negative surface potential of the liposome; particularly such that a surface potential of at least at least >0 mV, particularly to at >+10 mV, particularly to at least >+35 mV, in PBS, is achieved;
  b. decreasing the length of the individual hydrophobic anchor molecule; particularly to a length of less than 5 carbon atoms, particularly less than 4 carbon atoms, particularly less than 3 carbon atoms, particularly less than 2 carbon atoms;
  c. decreasing the number of hydrophobic anchor molecules at one end of the peptide molecule; particularly to a total of 1 anchor molecule;
  d. disaggregating β-sheet aggregates, particularly by adding of metal ions, particularly of Cu(II) and/or Zn(II) and/or by adding of small molecules capable of disaggregating β-sheet aggregates.

The present invention further relates to an immunogenic construct comprising a peptide molecule and a hydrophobic moiety covalently bound to the C- and/or N-terminal part of the peptide molecule, which peptide molecule is anchored into the lipid membrane of a liposomal carrier via said hydrophobic moiety, which immunogenic construct shows an reduced extent of β-sheet structure and/or β-sheet aggregation and comprises:
  a. a net negative surface potential of the liposome of at least at least >0 mV, particularly of at least >+10 mV, particularly of at least >+35 mV, in PBS;
  b. a length of the individual hydrophobic anchor molecule of less than 5 carbon atoms, particularly less than 4 carbon atoms, particularly less than 3 carbon atoms, particularly less than 2 carbon atoms;
  c. a number of hydrophobic anchor molecules at one end of the peptide molecule totalling 1 anchor molecule;
  d. metal ions, particularly Cu(II) and/or Zn(II) and/or small molecules capable of disaggregating β-sheet aggregates.

The liposome surface potential (zeta potential) of the liposome is determined as described in Examples (Part I, C2).

In certain embodiments, the present invention relates to test kits for detection and diagnosis of a proteinopathy comprising an immunogenic construct according to invention and as described herein.

In certain embodiments, the present invention relates to the use of an immunogenic construct according to invention and as described herein for screening of a conformation specific antibodies or a conformation-specific antibody fragment.

In certain embodiments, the present invention relates to the use of an immunogenic construct according to invention and as described herein for screening of small molecules which are capable of decreasing the extent of β-sheet aggregation of peptides, particularly peptides associated to cell membranes.

In certain embodiments, the present invention relates to the use of an immunogenic construct according to invention and as described herein for screening of small molecules for use in the treatment or prevention of a disease or disorder associated with the aggregation of peptides as defined herein.

In certain embodiments, the present invention relates to the use of an immunogenic construct according to invention and as described herein for detection and diagnosis of a proteinopathy, or for screening of conformation-specific antibodies or small molecules by monitoring the binding interactions using techniques such as Surface Plasmon Resonance (eg Biacore), ELISA, Fluorescence Resonance Energy Transfer, Time-resolved Fluorescence Resonance Energy Transfer or Immunoprecipitation.

DEFINITIONS

The terms "polypeptide", "peptide", and "protein", as used herein, are interchangeable and are defined to mean a biomolecule composed of amino acids linked by a peptide bond.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel, by HPLC, or any other method commonly used in the art.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95% homogeneity are preferred, and 80% to 95% or greater homogeneity are most preferred for use as therapeutic agents.

One of skill in the art recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", "an" and "the" as used herein are defined to mean "one or more" and include the plural unless the context is inappropriate.

The expressions "secondary conformation" and "secondary structure" are used herein interchangeably and refer to the general three-dimensional ordered arrangement or conformation of amino acids in localized regions of a polypeptide or protein molecule, such as, for example, beta amyloid.

The two main secondary structures are the alpha helix, the parallel or anti-parallel beta-pleated sheet, which are the most stable conformations. A single polypeptide or protein may contain multiple secondary structures in localized regions of the molecule.

A further secondary structure is the random coil conformation. In this conformation, the monomeric peptide subunits are oriented randomly while still being bonded to adjacent units.

An α-helix is a right-handed or clockwise spiral in which each peptide bond is in the trans conformation and is planar. The amine group of each peptide bond runs generally upward and parallel to the axis of the helix; the carbonyl group points generally downward. The helix is stabilized by hydrogen bonding between amine and carbonyl groups of the same polypeptide chain.

The β-pleated sheet consists of extended polypeptide chains with neighbouring chains extending parallel and anti-parallel to each other. As with the α-helix, each peptide bond is trans and planar. The amine and carbonyl groups of peptide bonds point toward each other and in the same plane, so hydrogen bonding can occur between adjacent polypeptide chains. The pleated sheet is stabilized by hydrogen bonds between the amine groups of one chain and the carbonyl groups of an adjacent chain. (http://chemistry.about.com/od/biochemistry/a/proteinstructur.htm)

In the random coil conformation, specific, stabilizing interactions are missing so that a polypeptide backbone may be present in all possible conformations randomly.

The expressions "quaternary structure" and "quaternary conformation" are used herein interchangeably and refer to the conformation of proteins or polypeptides, which are composed of aggregates of multiple subunits or monomeric peptides of defined structure. The arrangement of the multiple subunits or monomeric peptides of defined structure in the three-dimensional protein or peptide aggregate is the quaternary structure.

Stabilizing forces that include interactions between side chains of the subunits, are hydrophobic interactions among nonpolar side chains at the contact regions of the subunits, electrostatic interactions between ionic groups of opposite charge, hydrogen bonds between polar groups; and disulfide bonds.

In a specific embodiment of the invention the term "quaternary conformation" refers to the arrangement of the multiple subunits or monomeric peptides of defined structure in the three-dimensional polypeptide aggregate, wherein said subunits or monomers are composed of a peptide molecule and a hydrophobic moiety covalently bound to the C- and/or N-terminal part of the peptide molecule, which peptide molecule is anchored into the lipid membrane of a liposomal carrier via said hydrophobic moiety.

Through stabilizing interactions between: (i) the subunits or monomeric peptides of defined structure on the surface of the liposomal carrier, (ii) the lipid anchors and (iii) peptide and lipid head group interactions, aggregates are formed which mimic the quaternary structure of the native protein aggregates.

In a specific embodiment of the invention, the subunits or monomeric peptides of defined structure are Abeta or tau peptides, as defined herein.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies as well as active fragments thereof. Examples of active fragments of molecules that bind to known antigens include Fab and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (http://www.rctech.com/bioventures/therapeutic.php).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

"Functionally equivalent antibody" is understood within the scope of the present invention to refer to an antibody which substantially shares at least one major functional property with the reference antibody.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which an antigenic peptide or an antigenic construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention. In particular, the term carrier relates to liposomes.

Carrier proteins that can be used in the antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-Amino acids.

In the antigenic construct according to the present invention, the liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. It is also to be understood that the supramolecular antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Further, the term "immunogenic effective amount" refers to the amount of antigenic/immunogenic composition which, when administered to a human or animal, elicits an immune response. The effective amount is readily determined by one of skill in the art following routine procedures.

Further, the term "therapeutically effective amount" refers to the amount of antibody, peptide, compound or pharmaceutical composition which, when administered to a human or animal, leads to a therapeutic effect. The effective amount is readily determined by one of skill in the art following routine procedures.

The term "substantially the same immunogenic activity" refers to the ability of a compound, particularly a peptide, to induce an immune response in a human or an animal, the degree of which is comparable to that induced by a reference compound. In particular, the immune response is considered to be "substantially the same" if it is within the Standard Deviation (STD) range.

The term "substantially free of" refers to a situation where a compound or substance is either present in a concentration which is below the limit of detection or in a concentration which is sufficiently low so that the effect usually caused by said compound or substance is not detectable.

The term "substantially no cross-reactivity" refers to the reaction between an antigen and an antibody which was generated against a different but similar antigen, which reactivity is less than 3× the background level.

BRIEF DESCRIPTION OF DRAWINGS AND SEQUENCES

Figures

FIG. 1: Conformational analyses and metal binding properties of liposomal Palm1-15 peptide. (a) Fluorescence emission of liposomal formulation of Palm1-15 peptide (ACI-24), and upon addition of ThT to ACI-24, liposomes lacking peptide 'empty', and Acetyl1-15 peptide. Samples were analyzed in PBS at a peptide concentration of 15 µM with excitation at 440 nm. (b) ThT binding isotherm for liposomal peptide Palm1-15 (ACI-24). (c) CD spectra of lipidated peptide Palm1-15 embedded in liposomes and of acetylated 'native' peptide Acetyl1-15 in PBS. Spectra were recorded after 7-fold dilution for liposomal Palm1-15 in PBS with subtraction of a spectrum of the corresponding empty liposomes lacking peptide. (d) Fluorescence emission of ThT in the presence of liposomal vaccine ACI-24 upon addition of different metal ions. ThT was added to ACI-24 alone or to ACI-24 (final conc. 15 µM) pre-incubated with different metals (final conc. 20 µM) prior to addition of metal chelator DPTA (final conc. 200 µM). As a control, DPTA was added to liposomal Palm1-15 in the absence of Cu(II) resulting in no change to the ThT emission. Data are expressed as average±S.D. (n=3).

Figure 2:
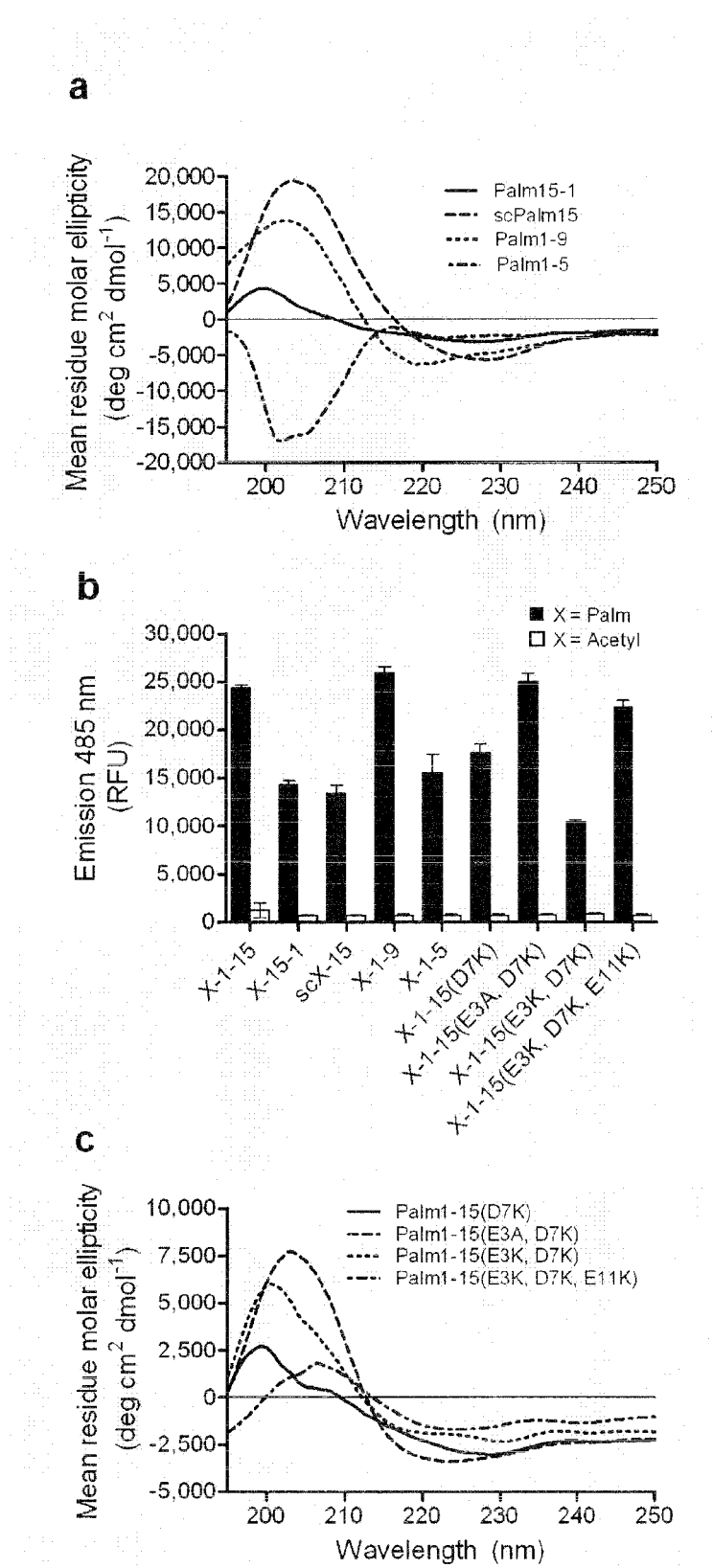

FIG. 2: Conformational analyses of various N- and C-terminal di-palmitoylated peptides of different primary sequence. (a) CD spectra of liposomal peptides Palm15-1, scPalm15, Palm1-9 and Palm1-5. (b) ThT fluorescence emission upon addition to liposomes embedded with different sequences of N- and C-di-palmitoylated peptides (filled bars), and corresponding 'native' acetylated peptides (open bars) in the absence of liposomes. Results are given as average±S.D. (n=3). (c) CD spectra of liposomal peptides Palm1-15(D7K), Palm1-15(E3A, D7K), Palm1-15(E3K, D7K) and Palm1-15(E3K, D7K, E11K).

Figure 3:
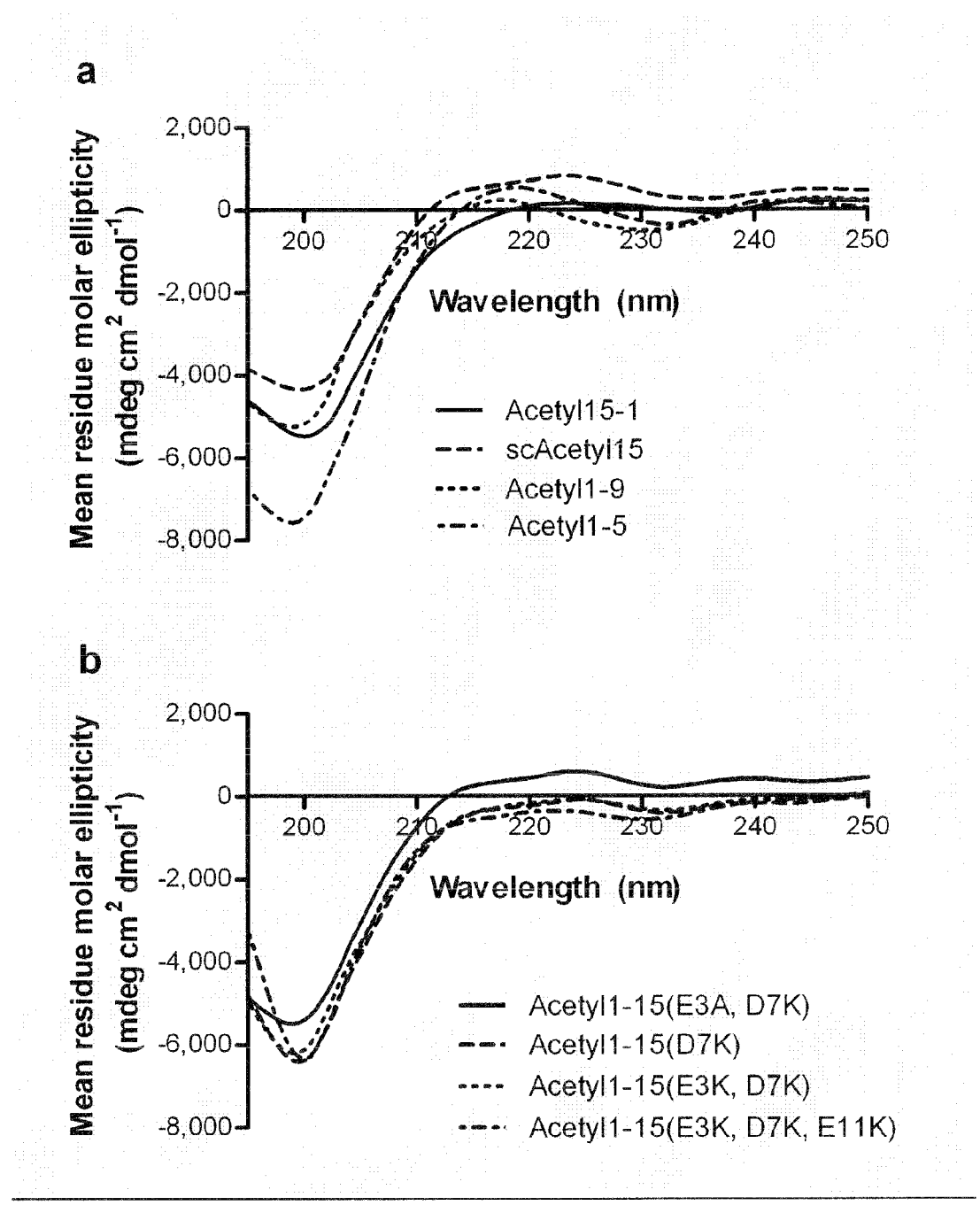

FIG. 3: CD spectra of tetra-acetylated 'native' peptides in PBS at pH 7.4. (a) Peptides Acetyl15-1, scAcetyl15, Acetyl1-9 and Acetyl1-5. (b) peptides Acetyl1-15(E3A, D7K), Acetyl1-15(D7K), Acetyl(E3K, D7K) and Acetyl1-15 (E3K, D7K, E11K). All peptides show CD spectra with minima at ~200 nm consistent with unstructured random coil conformations.

Figure 4:
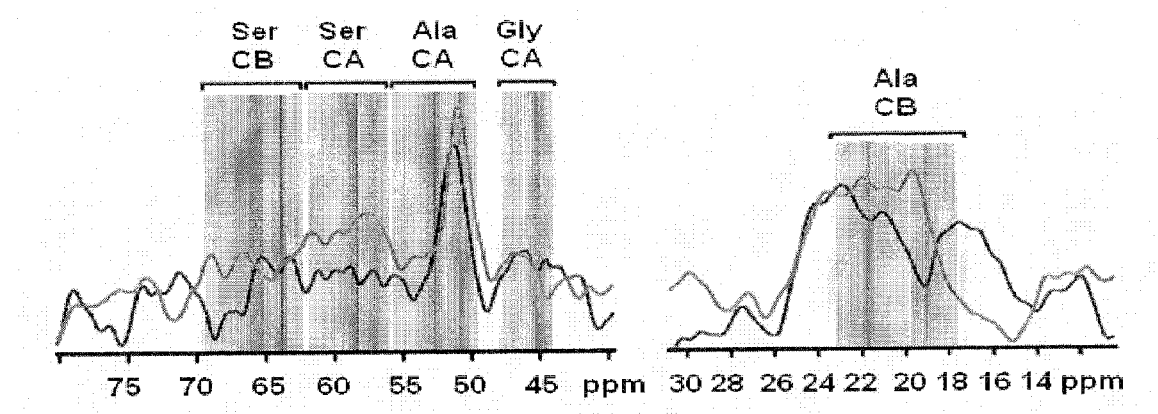

FIG. 4: Effect of liposome surface charge upon conformation of N- and C-terminal di-palmitoylated peptides integrated into liposomal bilayers. $^{13}C$-$^{13}C$ DQ MAS-NMR spectra of Palm1-15(ASG) peptide uniformly ($^{13}C/^{15}N$) labeled at position Ala-2, Ser-8 and Gly-9 and incorporated into anionic liposomes (DMPC/DMPG/Cholesterol/MPLA (molar ratio 9:1:7:0.06)) (light (blue) line), or cationic liposomes (DMTAP/Cholesterol/MPLA (molar ratio 10:7:0.06)) (dark (red) line). Conformation-dependent chemical shift ranges compatible with α-helix (blue), random coil (red) and β-sheet (green) backbone structure are annotated.

Figure 5:
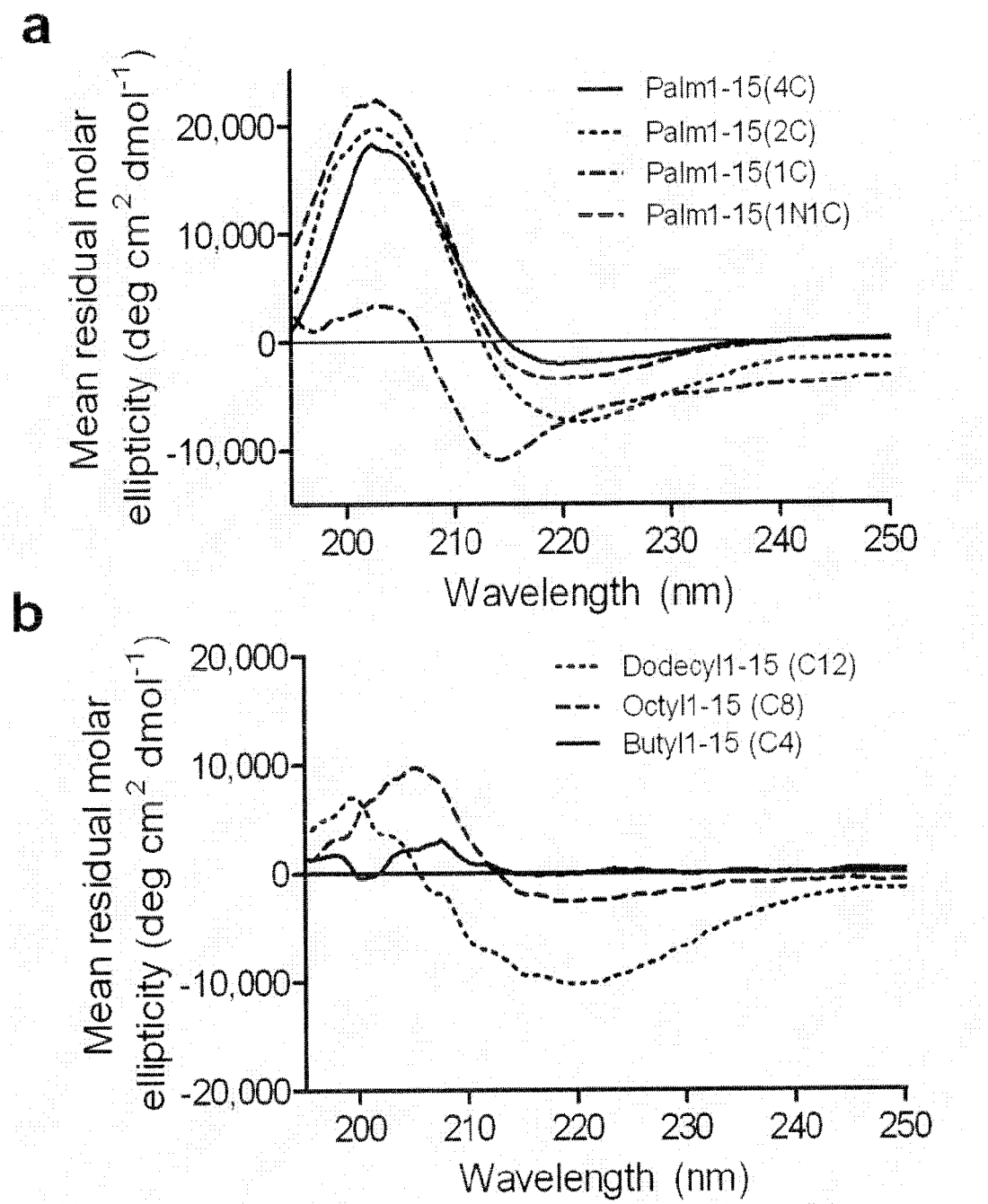

FIG. 5: Secondary and quaternary structural analysis of liposomal lipopeptides. (A) CD spectra of liposomal peptide constructs Palm1-15(4C), Palm1-15(2C), Palm1-15(1N1C) and Palm1-15(1C). (B) CD spectra of liposomal peptide constructs Dodecyl1-15, Octyl1-15 and Butyl1-15.

Figure 6:
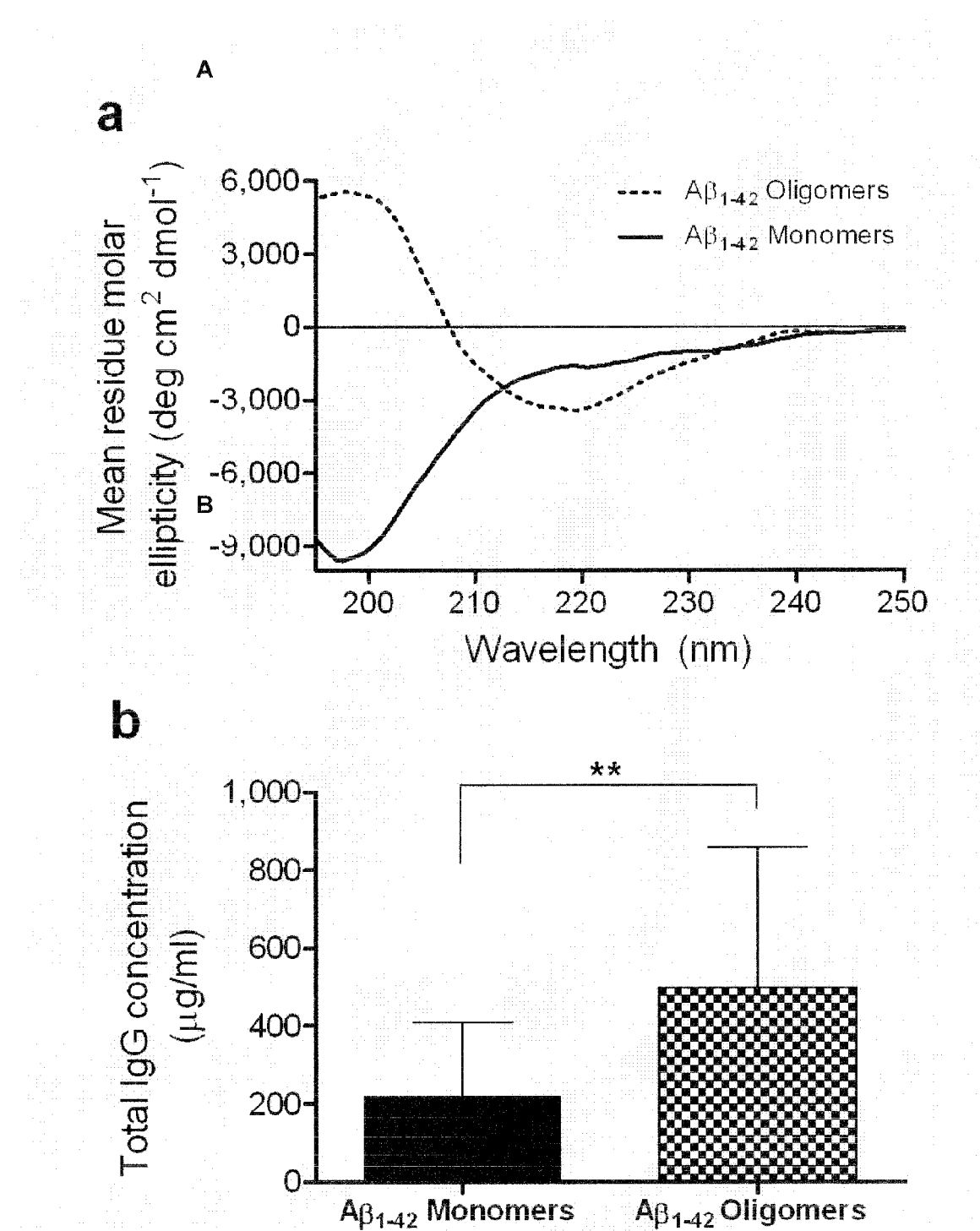

FIG. 6: Conformation-specific binding of anti-ACI-24 polyclonal antibodies to $A\beta_{1-42}$. (a) CD spectra of SEC purified oligomer and monomer fractions of $A\beta_{1-42}$. (b) Recognition of distinct $A\beta_{1-42}$ conformations by polyclonal plasma taken from wt mice after immunization with liposomal vaccine ACI-24. Monomeric (random coil) and oligomeric (β-sheet) $A\beta_{1-42}$ species were coated onto an ELISA plate and binding of plasma quantified relative to control IgG antibody 6E10. Data are expressed in mean±S.D. (n=10). **, P=0.002 using Wilcoxon Matched-Pairs Ranks.

Figure 7:
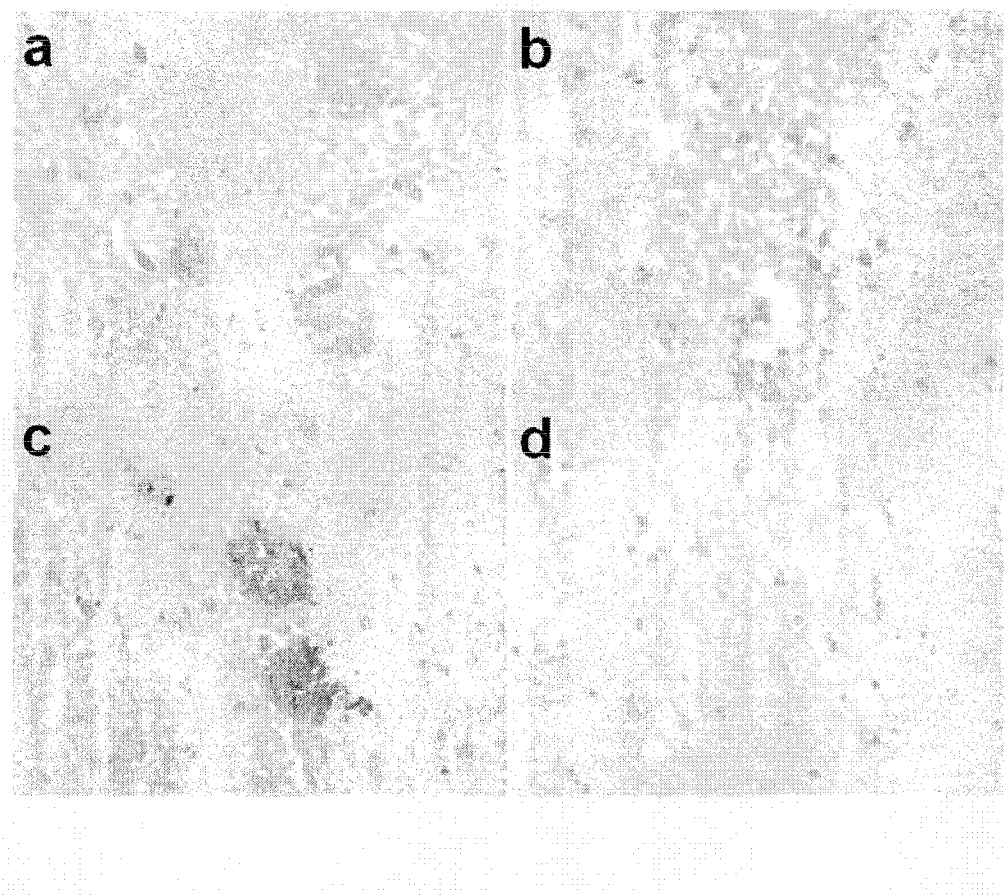

FIG. 7: Staining of pathological misfolded β-sheet plaques in human AD brain. (a) Staining of human AD brain, and (b) healthy human brain, with sera (diluted 1/2000) taken from a monkey immunized with ACI-24. Staining of human AD brain with (c) positive control monoclonal antibody (Dako mouse mAb), or (d) with sera from monkey immunized with PBS. Brain slices are magnified 40-fold.

Figure 8:
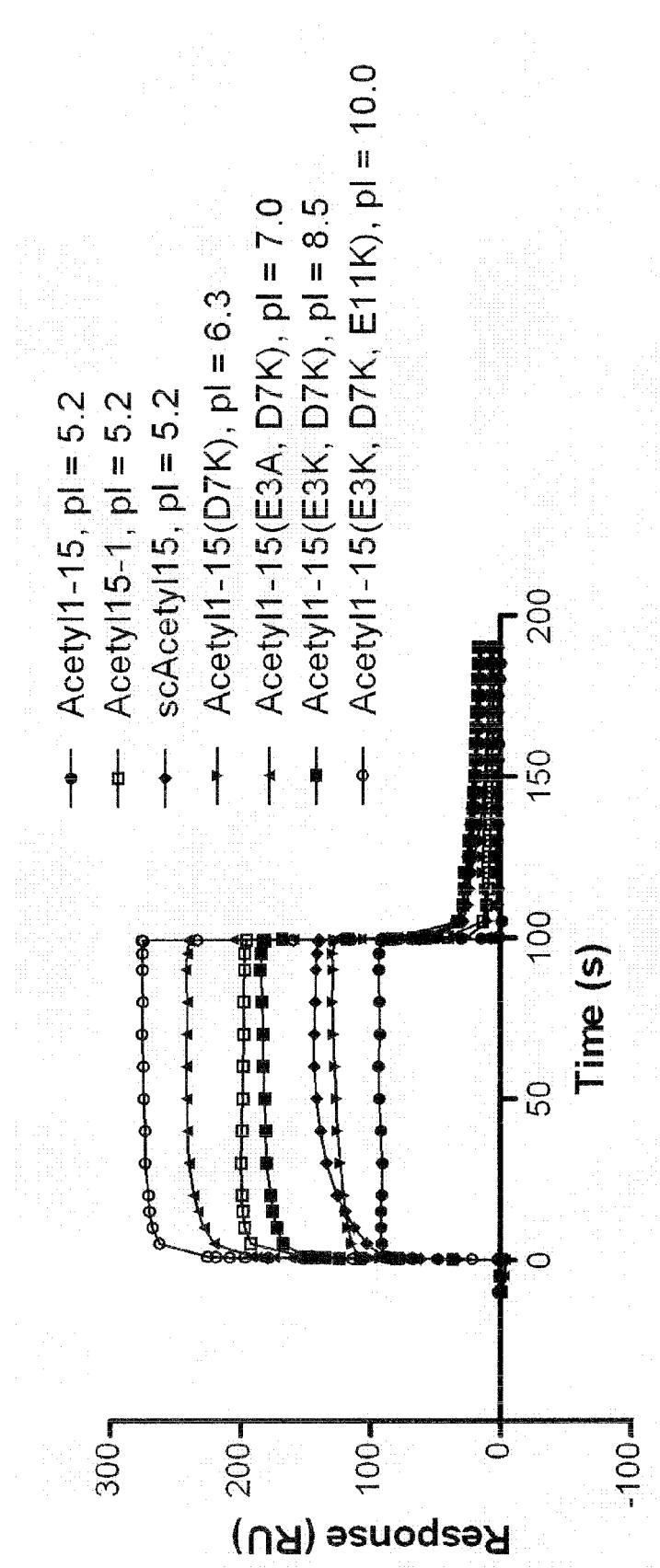

FIG. 8: SPR binding isotherms for the interaction of 19-mer tetra-acetylated peptides with liposomes. Peptides were injected all at 250 µM at 250 in PBS over 'empty' liposomes composed of DMPC, DMPG, Cholesterol and MPLA (molar ratio 9:1:7:0.06) immobilized onto a hydrophobic L1 sensor chip. Binding interactions were weak for all peptides as evidenced by fast on- and off-rates such that dissociation constants $K_d$ could not be obtained by kinetic analysis. No correlation is observed between the theoretical peptide isoelectric point (pI) and the binding response indicating that electrostatic interactions between amino acid side-chains and the lipid bilayer are weak.

Figure 9:
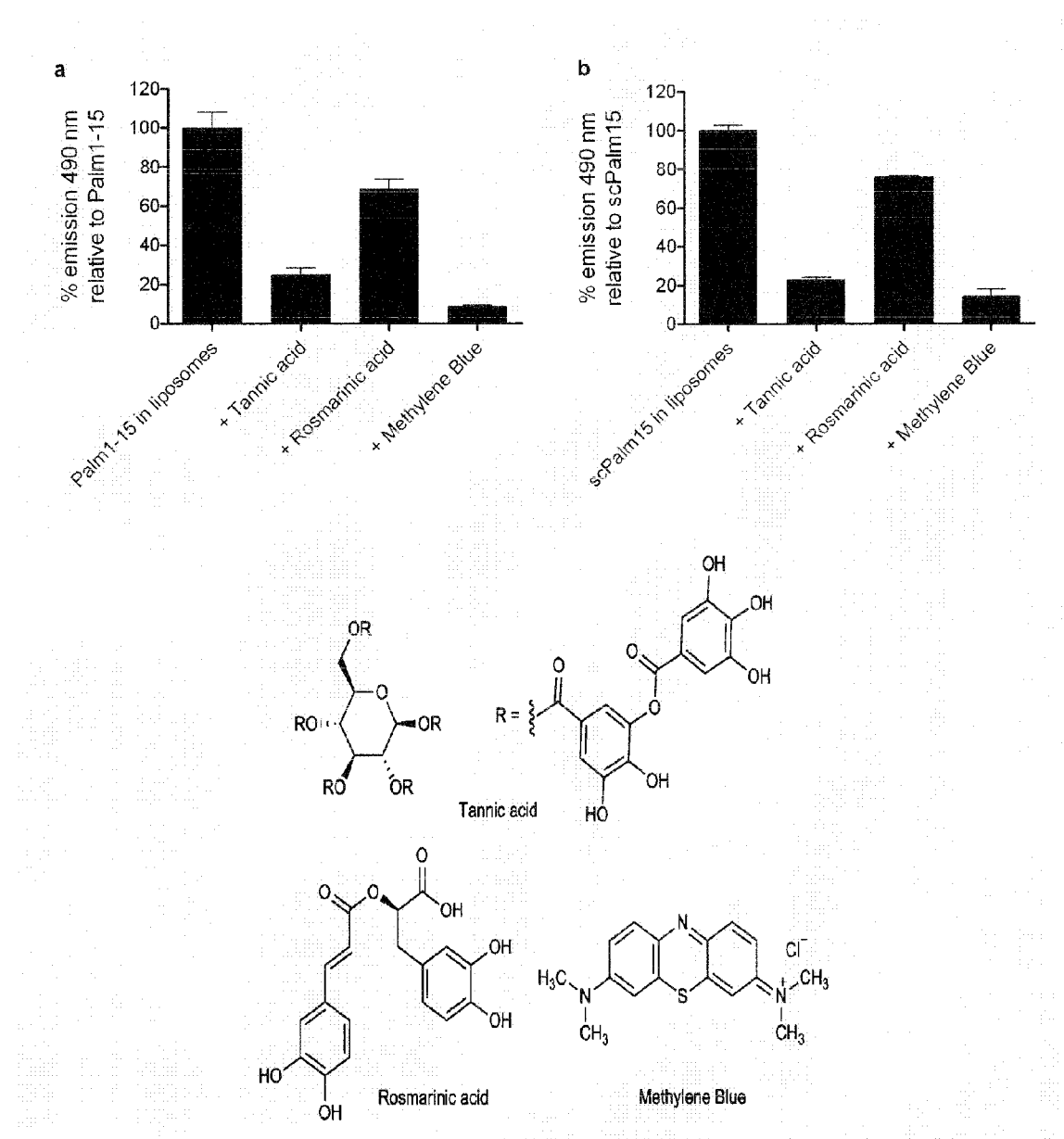

FIG. 9: Disaggregation of liposomal peptide β-sheets using small molecules. Liposomes containing (a) peptide Palm1-15, or (b) peptide scPalm15 of unrelated peptide sequence, were analyzed by ThT fluorescence after 2 h incubation with β-sheet breaker small molecules Tannic acid, Rosmarinic acid and Methylene Blue (structures shown below). Results are given as average±S.D. (N=3).

SEQUENCE LISTING

SEQ ID NO: 1 Control Sequence T5: Tau 379-408 [pS396, pS404]
SEQ ID NO: 2 Sequence 1 (T1): Tau 5-20 [pY18]
SEQ ID NO: 3 Sequence 8 (T8): Tau 206-221 [pT212, pS214]
SEQ ID NO: 4 Sequence 9 (T9): Tau 196-211 [pS202, pT205]
SEQ ID NO: 5 Sequence 3 (T3): Tau 393-408 [pS396, pS404]
SEQ ID NO: 6 Sequence 4 (T4): Tau 401-418 [pS404, pS409]
SEQ ID NO: 7 Sequence 2 (T2): Tau 200-216 [pS202+pT205 & pT212+pS214]
SEQ ID NO: 8 Sequence 10 (T10): Tau 407-418 [pS409]
SEQ ID NO: 9 Sequence 11 (T11): Tau 399-408 [pS404]
SEQ ID NO: 10 antigenic peptide Aβ 1-15
SEQ ID NO: 11 antigenic peptide Aβ 1-16
SEQ ID NO: 12 antigenic peptide Aβ 1-16(Δ14)
SEQ ID NO: 13 antigenic peptide Aβ 4-11
SEQ ID NO: 14 antigenic peptide Aβ 22-35
SEQ ID NO: 15 antigenic peptide Aβ 29-40
SEQ ID NO: 16 antigenic peptide Aβ 1-5

EXAMPLES

PART I

A General Methodology:
A1 CD Spectroscopy.
  CD spectra were acquired on a Jasco-815 spectropolarimeter (Japan) with a 0.1 cm path length quartz cuvette at 23° C. Measurements were made with a 1.0 nm bandwidth and 0.5 nm resolution. A scan speed of 50 nm/min was employed with response time of 1 s. Solvent control spectra (4 scans) were averaged and subtracted from the average of 8 scans of each sample spectra. All spectra ($[\theta]_{obs}$, degrees) were smoothed after being converted to mean residue molar ellipticity ($[\theta]$, degrees cm$^2$ dmol$^{-1}$) with the equation $[\theta]=[\theta]_{obs}\times(MRW/10lc)$, where MRW is the mean residue molecular weight (MW/number of residues), l is the optical path length (cm) and c is the concentration (g/cm$^3$). For analysis liposomal suspensions were diluted 6-fold in PBS to give final peptide concentrations between 10 to 40 μM. Spectra of the corresponding empty liposomes lacking peptide were subtracted.

A2 ThT Fluorescence.
  Fluorescence emission spectra were measured at 25° C. on a Tecan M200 spectrofluorimeter with an excitation of 440 nm. Liposomes were diluted 8-fold in PBS to give a final peptide concentration of 15 μM and then ThT added at different concentrations. Data were fitted using non-linear regression analysis (SigmaPlot v10.0) assuming single-site binding saturation in order to calculate apparent $K_d$ and maximal binding $B_{max}$.

A3 Disaggregation Assay Using ThT Fluorescence.
  $ZnCl_2$, $FeCl_3$ or $CuCl_2$ (2 μL, 1 mM in $H_2O$) were incubated with liposomes diluted 4-fold in PBS (48 μL) for 2 h at 22° C. PBS (48 μL) with or without DPTA (0.4 mM) was added accordingly after 5 min. ThT (2 μL, 2.4 mM in $H_2O$) was then added and fluorescence measured after a further 5 min. For disaggregation with small molecules, Rosmarinic acid, Tannic acid or Methylene Blue (2 μL, 2.7 mM in PBS) were added to 86 μL of liposomes diluted 8-fold with PBS. After 2 h incubation at RT, ThT (2 μL, 2.4 mM in $H_2O$) was added and after 10 min. fluorescence was measured at 490 nm (Ex. 440 nm).

A4 MAS-NMR Spectroscopy.
  Experiments were conducted using a 3.2 mm triple-resonance ($^1$H, $^{13}$C, $^{15}$N) MAS probe (Bruker Biospin, Germany) at a static magnetic field of 16.4 T corresponding to 700 MHz proton resonance frequency. For analysis, the amino acids A(2), S(9) and G(10) of Palm1-15 were uniformly labeled with $^{13}$C and $^{15}$N. This peptide Palm1-15(ASG) was then incorporated into liposomes composed of phospholipids (DMPC, DMPG or DMTAP), cholesterol and MPLA, giving a final peptide concentration of 121 μM.
  To isolate signals of the $^{13}$C-labeled peptide variants in the presence of the unlabeled background, $^{13}$C Double Quantum (DQ) spectroscopy was applied. Experiments were recorded using 10 kHz MAS and at effective sample temperature of about 4° C. After a cross polarization (CP) step employing a contact time of 600 μs, the SPC5 pulse sequence was used for generation of DQ coherence, with a $^{13}$C radio frequency (r.f.) field strength of 50 kHz and DQ excitation and reconversion time totaling 2.28 ms. Acquisition involved in each case 110K repetitions. An $^1$H field strength of 83.3 kHz was used during excitation and SPINAL64 proton decoupling.

A5 SPR Analysis of Peptide-Liposome Interactions.
  Experiments were performed at 25° C. using 0.2 μm filtered and degassed PBS as running buffer. An L1 sensor chip (GE Healthcare, Sweden) was docked into a BIAcore 1000 instrument and the chip surface conditioned by injection of 50 μL of Zwittergent at 30 μL/min. Liposomes lacking peptide ('empty' liposomes) were then immobilized onto the sensor chip following 2 successive injections of 50 μL at 2 μL/min. Finally 50 μL of 50 mM NaOH was injected over the surface at 30 μL/min in order to render the surface more unilamellar. After this wash step typically around 8000 RUs of liposomes remained immobilized. 50 μL of acetylated peptides solubilized in PBS were then injected over the surface over a range of concentrations at a flow rate of 30 μL/min, followed by dissociation with PBS for 300 s. After analysis of the interaction of different peptides, a fresh lipid bilayer was immobilized.

A6 Dynamic Light Scattering.
  Liposome samples were diluted 100-fold with PBS. Analysis was performed using a Zetasizer Nano (Malvern, USA) at 25° C. Data was analyzed with DTS 5.0 (Malvern) software by signal intensity in order to calculate the average liposome diameter and polydispersity index (PDI).

A7 Cryo-EM.
  Liposome sample was diluted 6-fold with PBS and then 3 μL was applied on glow discharged R 2/4 holey carbon grids (Quantifoil®), blotted off, and plunged frozen into liquid ethane under temperature and humidity controlled conditions using the Vitribot™ (FEI, The Netherlands). The grids were transferred and stored under liquid nitrogen prior to EM imaging. Low dose EM imaging was performed under cryo conditions on a JEM-2100F field emission gun transmission electron microscope (Jed), with an accelerating voltage of 200 kV. EM images were acquired at 10 k, 30 k, 80 k and 150 k magnification using a TemCam-F415 4 k×4 k CCD camera (Tietz Video and image Processing Systems).

B Peptide Synthesis
B1 General Methods.
  TBTU was obtained from SENN Chemicals (Switzerland). Technical grade DCM, HiPerSolv CHROMANORM iPrOH and HiPerSolv CHROMANORM $CH_3CN$ were purchased from VWR BDH Prolabo. HPLC-grade TFA was obtained from Fisher Scientific. $PalmA\beta_{1-15}$ was prepared by Bachem (Switzerland). $AcetylA\beta_{1-15}$ was synthesized and purified by Polypeptides Laboratories (France). All other chemicals and solvents were purchased from Sigma-Aldrich.

B2 Synthesis of Protected Peptidyl-Resins.

Protected peptidyl resins were obtained from Polypeptides Laboratories (France). Peptide sequences were assembled stepwise by solid phase synthesis on a pre-loaded Fmoc-Lys(Mtt)-Wang resin, using standard Fmoc/tBu chemistry (0.25 mmol/scale). Trityl was applied for the protection of the side chains of His and Gln and Pbf for the protection of Arg. The N-terminal and/or C-terminal lysines were orthogonally protected with the Mtt group. Coupling of all amino acids was performed in DMF in the presence of a fivefold excess of PyBOP, HOBt and DIEA. Before each coupling the Fmoc N-terminal group was removed by treatment with 25% piperidine/DMF followed by a wash step with DMF.

B3 Synthesis of Acetylated Peptides and Lipopeptides.

The orthogonal protecting Mtt groups of the terminal lysine residues were selectively cleaved by treatment of the resin with TIPS/TFA/DCM (1:1:98) during several cycles of 10 min. In general for palmitoylated peptides, palmitic acid (20 eq) was then coupled to the free amino groups using TBTU (20 eq) and DIEA (40 eq) in DCM/DMF (1:1) during 8 h. For acetylated peptides, the free amino groups were acetylated with acetic anhydride (50 eq) and DIEA (100 eq) in DMF during 2-3 h. Then, the N-terminal Fmoc group was removed with 20% piperidine in DMF (3×10 min). Washing steps with DCM/DMF were performed between every different step. Finally simultaneous resin cleavage and side-chain deprotections were carried out using a mixture of TFA/TIPS/$H_2O$ (95:2.5:2.5) during 2-3 h. Trituration from cold diethyl ether and lyophilization from $tBuOH/H_2O$ (1:3) gave yield to the crude product as a white solid. Peptide identity and purity were assessed by MALDI-TOF mass spectrometry and HPLC analysis.

B4 HPLC Analysis of Peptides.

Reverse-phase high performance liquid chromatography was performed with monitoring wavelengths were 214 and 280 nm and a flow of 1.0 mL/min was used during injection. In general palmitoylated peptides were dissolved in neat HFIP (1 mg/mL) and analyzed with a ZORBAX Stable Bond analytical column 300SB-C3 (Agilent) (4.6×250 mm, 5-Micron, 300 Å pore). A linear gradient of 40% B to 60% B in 25 min at 75° C. was used throughout, where A=0.1% TFA, 10% $CH_3CN$, 89.9% $H_2O$ and B=0.1% TFA, 5% $H_2O$, 94.5% Isopropanol. For peptides Palm1-15(1N1C), Palm1-15(2C) and Palm1-15(1C), a linear gradient of 0% B to 60% B in 25 min at 75° C. was used. For acetylated peptides, Zorbax Eclipse analytical column XDB-C18 (Agilent) was used (4.6×250 mm, 5-Micron). Peptides were dissolved in $H_2O$ or in 0.1% TFA, 20% $CH_3CN$, 79.9% $H_2O$. In general, a linear gradient of 0% B to 30% B in 15 min (after an initial step of 0% B during 5 min) at 25° C. was used throughout, where A=0.1% TFA, 10% $CH_3CN$, 89.9% $H_2O$ and B=0.1% TFA, 99.9% $CH_3CN$. For peptides Acetyl1-5(D7K) and Acetyl1-5(E3A, D7K) a flow of 0.7 mL and 30° C. was applied. For peptides Acetyl15-1, scAcetyl15 and Acetyl1-9, a linear gradient of 0% B to 30% B in 10 min (after an initial step of 0% B during 10 min) at 22° C. was used instead. Peptide Butyl1-15 and Octyl1-15 were eluted with a linear gradient of 10% B to 50% B in 30 min at 30° C. and 40° C. respectively. Peptide Dodecyl1-15 was eluted with a linear gradient of 10% B to 100% B in 30 min at 40° C.

B5 MS Analysis of Peptides.

Matrix-assisted laser desorption ionization-time of flight-mass spectrometry (MALDI-TOF-MS) data were acquired on an AXIMA CPR™ Plus (Shimadzu Biotech/Kratos Analytical, Japan) instrument in linear mode positive (DHB as matrix) or reflectron mode positive (ACHA as matrix). Generally for lipopeptides, 10 µL of sample in (1:1) TFA/$CH_3CN$ was mixed with 10 µL of matrix, vortexes and sonicated and finally spotted on the MALDI plate. For acetylated peptides, sample was solubilized in 0.1% TFA, 20% $CH_3CN$ and 79.9% $H_2O$.

C Liposomes

C1 Liposome Preparation.

Palmitoylated peptide was solubilized at a concentration of 4 mg/mL in hexafluoroisopropanol (total 1 mL). Unless stated otherwise, this was then added to a stirred solution of DMPC, DMPG, cholesterol and adjuvant MPLA (Avanti Polar Lipids, USA) solubilized in chloroform (molar ratio 9:1:7:0.06, total volume 9 mL). The resulting solution was filtered through a 0.2 µm hydrophobic PTFE filter to ensure the removal of any insoluble particles. This solution was then evaporated under reduced pressure at 40° C. and then under high vacuum ($10^{-3}$ mbar) for 3 h. The resulting thin-film was then rehydrated with PBS with agitation overnight to give a final peptide concentration of 121 µM and a phospholipid concentration of 12.1 mM. For in vivo studies, liposomes were prepared by solubilizing DMPC, DMPG, cholesterol and MPLA (all Avanti Polar Lipids, USA) (molar ratio as above) respectively in EtOH at 40-60° C. This lipid/ethanol solution was then mixed with a solution of Palm1-15 in 1-2% octyl-β-D-glucopyranoside (β-OG)/PBS pH 7.5-8.0 either by manual injection (for mice immunization) or using the cross-flow ethanol injection technique (for monkey immunization). The generated liposomes were concentrated by ultra-filtration and then residual solvents removed by diafiltration using a 100 k Da cut-off polyethylsulfone membrane. Liposomes prepared by manual injection were extruded sequentially through polycarbonate filters of decreasing pore sizes (1, 0.4, 0.2, 0.1 then 0.08 µm) using an EmulsiFlex-C5 extruder (Avestin, Canada). The resulting liposomes were finally stored at 5° C. prior to use.

C2 Liposome Surface Potential.

Liposome samples were diluted 100-fold with PBS. Analysis was performed using a Zetasizer Nano (Malvern, USA) at 25° C. Measurement duration and voltage selection were performed in automatic mode, with a typical applied voltage of 50 mV. Data was transformed using the Smoluchowski equation automatically using DTS 5.0 (Malvern) software to calculate the zeta potential.

D Vaccine

D1 Vaccine Preparation for Immunization.

Antigen constructs are prepared using the lipids DMPC, DMPG, cholesterol and MPLA (all Avanti Polar Lipids, USA) at molar ratios 9:1:7:0.05 respectively. Palm1-15 is added to give a peptide/phospholipid ratio of 1:100 and at a final concentration of 121 µM (see General Methodology, C1, for details). Vaccine is characterized by HPLC for peptide, MPLA and lipid content.

D2 HPLC Analysis of Vaccine for Content of Peptide, Cholesterol and DMPC.

Standards of Palm1-15, DMPC and Cholesterol are used for calibration using aliquots containing all three components at five different concentrations in a mixture of isopropanol, trifluoroacetic acid (TFA) and water (ratio 7:1:2). For analysis of the antigen constructs, samples are prepared by adding water (20 µL) to the antigen construct (20 µL) in a glass HPLC vial, followed by isopropanol (140 µL) and TFA (20 µL). The sample is briefly vortexed prior to injection (20 µL). Analysis is performed using a C3-reverse-phase Zorbax 300SB-B3 column (250×4.6 mm, 5 µm, 300 Å, Agilent) thermostated to 75° C., with detection at 207 and 214 nm. Eluent solvents are as follows: solvent A, 95% Acetonitrile, 5% Water, 0.1% TFA; solvent B, 10% Acetonitrile, 90% Water, 0.1% TFA. Flow rate is maintained at 1 mL/min.

D3 HPLC Analysis of Vaccine for Content of MPLA.

MPLA content is quantified by HPLC with UV detection following derivatization of MPLA within the antigen construct with dinitrobenzyloxyamine (DNBA).

D4 Animal Care and Treatment.

All treatments are carried out in accordance to local regulations. C57BL/6 adult mice (10 females/group) received subcutaneous injections of antigen construct on three occasions with a two-week interval between each immunization (at day 0, 14 and 28). Blood samples are collected and plasma prepared at day 35. Cynomolgus monkeys are immunized 4 times at 3 week intervals. 8.5 months after the last immunization, monkeys are re-immunized subcutaneously (sc.) the leg area with 2 doses of antigen construct at day 2 and day 24.

D5 SEC $A\beta_{1-42}$ Monomer and Oligomer Preparations.

$A\beta_{1-42}$ used for SEC-HPLC fractionation is synthesized and purified by Dr. James I. Elliott at Yale University (New Haven, Conn., USA). $A\beta_{1-42}$ powder (1 ma) is equilibrated to RT for 6 min, dissolved in 50 µL DMSO, followed by 800 µL of doubly distilled (dd) $H_2O$ and 10 µL of 2 M Tris-HCl pH 7.4 and mixed by vortex. Aβ preparation is incubated for 3-4 min at RT and centrifuged for 10 min at 6,000×g at 4° C. After centrifugation, the supernatant is immediately injected onto the HPLC and run over two columns: TSK-GEL G4000PWXL (Tosoh Bioscience, Belgium) and Superose 6 10/300 GL (GE Healthcare, Switzerland) with a flow of 0.3 mL/min. Thirty fractions of 1 mL are collected and stored at 4° C. until use immediately after the fractionation is completed. The concentration of Aβ monomers and oligomers enriched SEC-HPLC fractions are measured by absorbance at 280 nm in a glass cuvette.

D6 Conformational Specificity of IgG Antibodies.

ELISA plates are coated for 2 h at 4° C. with SEC Monomer and Oligomer $A\beta_{1-42}$ preparations diluted in PBS to obtain 10 µg/mL concentrations. After coating, washing with PBS-0.05% Tween 20 is performed followed by blocking with 1% BSA for 1 h at 37° C. Serial dilutions of sera are added to the plates and incubated at 37° C. for 2 h. After washing, plates are incubated with alkaline phosphatase (AP) conjugated anti-mouse IgG antibody (Jackson Immunoresearch, USA) for 2 h at 37° C. After final washing, plates are incubated with AP substrate para-nitrophenylphosphate (pNPP) for 2.5 h at RT and read at 405 nm using an ELISA plate reader. Results are expressed by reference to serial dilutions of monoclonal antibody 6E10 (Covance, USA).

D7 Human Post-Mortem Tissues.

Prepared cryo-sections of human Alzheimer's brain (cortex) tissue are used as a positive control tissue, while normal human brain (cortex) tissue is used as a negative control. The panel of human tissues is obtained from Tissue Solutions, UK and analyses performed by Covance Laboratories Ltd, Harrogate, UK.

D8 Serum and Antibodies.

Mouse monoclonal antibody against β Amyloid (anti-Human Beta-Amyloid, M0872, Dako) is used as a positive control antibody. Cynomolus monkeys (*Macaca fascicularis*) are immunized 4 times at 3 week intervals with antigen construct. 8.5 months after the last immunization, monkeys are re-immunized subcutaneously (s.c.) in the leg area with 2 doses of antigen construct at 3 week intervals. Serum is used at 1/2000 dilution. Serum of one animal immunized with PBS is used as a negative control. A goat anti-monkey IgG (1/100 dilution) and a biotinylated rabbit anti-goat IgG are used to detect primary non-primate antibody.

D9 Immunohistochemistry.

Cryostat sections of ~5 µm thick are prepared and fixed in acetone followed by 10% Neutral Buffered Formalin (NBF). After washing, sections are incubated with Dako REAL, Serum Blocking Solution, Avidin Solution and Biotin solutions. Cryo-sections are incubated overnight with diluted sera and incubated with goat anti-monkey IgG followed by biotinylated rabbit anti-goat. VECTASTAIN ABC/HRP and DAB (3,3' diaminobenzidine tetrahydrochloride) are used to detect antibody complexes. After staining, sections are washed and incubated with 0.5% copper sulphate solution, counterstained in Haematoxylin and mounted. All reagents are diluted in antibody diluents, and all incubation steps are preceded by washing in PBS and are performed at room temperature.

E Statistical Evaluation.

The data were analyzed using the non-parametric Wilcoxon Matched-Pairs Ranks. A value of P<0.05 was considered to be statistically significant.

PART II

A Experimental Results

In order to investigate the structure-conformation relationship of liposomal tetra-palmitoylated peptides, a range of peptides were synthesized (Table 1), and their biophysical properties analyzed by various techniques either alone as 'native' tetra-acetylated peptides or as tetra-palmitoylated peptides embedded into liposome bilayers.

A1 Disaggregation of Palm1-15 β-Sheet Aggregates

It was reported previously that Palm1-15 (Table 1) adopts a β-sheet conformation within the lipid bilayer of ACI-24 (Muhs, A. et al., Proc. Natl. Acad. Sci. U.S.A. 104, 9810 (2007)). To explore the conditions under which this conformation induces aggregation, fluorescence of Thioflavin T (ThT) was measured upon addition to ACI-24. ThT is a small benzothiazole dye which exhibits a strong red-shift in its emission spectrum upon binding to aggregated β-sheet peptides. As such, it has been widely used to detect and characterize the aggregation of β-amyloid peptides into both oligomers and fibers. Addition of ThT to ACI-24 gave rise to a strong fluorescence emission at 485 nm, characteristic of the emission spectra for β-sheet aggregated amyloid (FIG. 1a). No emission above background was observed over the same range in the presence of liposomes lacking peptide ('empty' liposomes) confirming that the liposome matrix did not cause interference. Since Palm1-15 peptide is highly insoluble in PBS, an acetylated and PBS soluble version 'Acetyl1-15' peptide was synthesized and analyzed however this showed no emission at 485 nm in the presence of ThT (FIG. 1a). For Palm1-15 in liposomes, the fluorescence response value at saturation $B_{max}$ and the apparent $K_d$ value of 2.4 µM were determined from fitting the fluorescence emission at 485 nm upon addition of ThT at different concentrations to Palm1-15 (ACI-24) (FIG. 1b). This apparent $K_d$ value is similar to that reported for the interaction of ThT with $A\beta_{1-40}$ (11 µM). ThT data were in agreement with the circular dichroism (CD) spectra which show that the liposomal Palm1-15 adopts a β-sheet secondary structure whereas 'native' Acetyl1-15 peptide alone is unstructured in PBS solution (FIG. 1c). Thus, within the liposomal formulation of ACI-24, Palm1-15 forms β-sheet aggregates that are tinctorially similar to β-amyloid. In order to further examine the similarities between Palm1-15 and $A\beta_{1-42}$ aggregates and to better understand the mechanism of β-sheet assembly upon incorporation into lipid bilayers, it was investigated whether preformed β-sheet aggregates of liposomal Palm1-15 could be disaggregated by Cu(II) as reported for $A\beta_{1-42}$ fibers. To this end ACI-24 was incubated with $CuCl_2$ for 2 h and then analysed by ThT. Likewise, the effect of adding $ZnCl_2$ and $FeCl_3$ was investigated. FIG. 1d shows that at near stoichiometric concentration of metal:peptide, the ThT fluorescence is decreased by ~75% upon addition of Cu(II), whereas only ~12% reduction was observed with Zn(II) and none with Fe(III). A shorter incubation time of just 5 min revealed a similar reduction upon addition of Cu(II), while an $EC_{50}$ value for Cu(II) disaggregation of ~3 µM was determined. When the metal chelator diethylenetriamine pentaacetic acid (DPTA) was added to the metal-liposome solution instead of PBS alone, analysis by ThT fluorescence revealed an increase in fluorescence, similar to that found prior to addition of Cu(II).

These data reveal that Palm1-15 is disaggregated by Cu(II) and can re-assemble within the lipid bilayer post-liposome formation to form aggregates comparable to those formed prior to Cu(II)-induced dis-assembly. The ability of Cu(II) to disaggregate Palm1-15 β-sheets thus further highlight the similarities between Palm1-15 aggregates and $A\beta_{1-42}$ aggregates.

A2 N- and C-Terminal Di-Palmitoylated Peptides not Related to Aβ Form β-Sheet Aggregates in Liposomes Bilayers In order to determine whether the formation of β-sheet aggregates of liposomal Palm1-15 was related to the peptide sequence in $A\beta_{1-15}$, the unrelated reverse sequence Palm15-1 and scrambled sequence scPalm15 were synthesized (Table 1). These peptides were then incorporated into liposomes as for ACI-24 and analyzed by CD spectroscopy. As can be seen in FIG. 2a both liposomal peptides Palm15-1 and scPalm15 show minimal mean residue molar ellipticities at ~220 nm. These spectra are similar to that found for liposomal Palm1-15 and characteristic of a β-sheet conformation. In contrast, the tetra-acetylated peptides Acetyl15-1 and scAcetyl15 corresponding to the sequences from Palm15-1 and scPalm15 were synthesized and upon analysis by CD were found to adopt random coil conformations (FIG. 3). When analyzed by ThT fluorescence, positive ThT emission signals were observed, whereas the corresponding acetylated peptides Acetyl15-1 and scAcetyl15 alone (native peptides) showed no fluorescence (FIG. 2b). Thus, the aggregation observed for Palm1-15 is not unique to the $A\beta_{1-15}$ amino-acid sequence but also occurs for other unrelated sequences upon peptide palmitoylation and incorporation into liposomes. Slight differences in fluorescence intensity were nevertheless observed between liposomal peptides Palm1-15, Palm15-1 and scPalm15 (FIG. 2b) despite similar binding affinities for ThT (Table 2), suggesting that the peptide sequence has only a minor influence on the extent of β-sheet aggregation.

A3 Short N- and C-Terminal Di-Palmitoylated Peptides Form β-Sheet Aggregates in Liposomes Since the binding epitope within $A\beta_{1-42}$ of sera taken from mice immunized with ACI-24 was found to be in the region $A\beta_{1-9}$ (Muhs, A. et al., Proc. Natl. Acad. Sci. U.S.A. 104, 9810 (2007)), the effect of peptide length on conformation was investigated. To this end the truncated peptides Palm1-9 and Palm1-5 were synthesized (Table 1). Upon incorporation into liposomes, peptide Palm1-9 was found to form β-sheet aggregates by CD (FIG. 2a) similar to liposomal peptide Palm1-1 (FIG. 1a). On the contrary, lipopeptide Palm1-5 was found to give a CD spectrum consistent with a mixed proportion of extended β-sheet and random coil conformations. This was supported by ThT binding data showing lower ThT fluorescence intensity (FIG. 2b), and a lower $B_{max}$ value for liposomal peptide Palm1-5 compared to Palm1-15 or Palm1-9 (Table 2). In summary, even short tetra-palmitoylated peptides generate β-sheet aggregates within the liposome bilayers.

A4 N- and C-Terminal Di-Palmitoylated Peptides Form β-Sheet Aggregates in Liposomes Bilayers Independent of Peptide Charge To examine whether the preference for β-sheet formation would still arise for peptides with different net charges at physiological pH, a range of $A\beta_{1-15}$ mutants (Palm1-15 (D7K), Palm1-15(E3A, D7K), Palm1-15(E3K, D7K) and Palm1-15(E3K, D7K, E11K)) were synthesized, wherein different numbers of acidic amino acids within $A\beta_{1-15}$ were replaced by either basic Lys (K) or neutral Ala (A) residues (Table 1). In this way it was possible to create a series of peptides with very different isoelectric points ranging from 5.2 to 10.0 (Table 2), such that they carry net negative, neutral and positive charges at physiological pH. These different peptides were then incorporated into liposomes carrying a negative surface charge as for ACI-24. CD spectroscopic analyses of these liposomal peptides revealed characteristic minima at ~220 nm (FIG. 2c) indicative of β-sheet secondary structure. These findings were supported by ThT analyses which showed that all liposomal tetra-palmitoylated peptides gave rise to positive ThT signals, while the corresponding acetylated 'native' peptides did not (open bars, FIG. 2b). All liposomal peptides Palm1-15(D7K), Palm1-15(E3A, D7K), Palm1-15(E3K, D7K) and Palm1-15(E3K, D7K, E11K) were found to have similar binding affinities for ThT as well as similar $B_{max}$ values, except for mutant Palm1-15(E3K, D7K) having a slightly lower $B_{max}$ value. Together, this data demonstrates that the β-sheet aggregation of N- and C-di-palmitoylated peptides embedded into anionic liposomes occurs for a range of peptide sequences independent of their electrostatic charge. In order to evaluate the role of peptide-liposome interactions upon the variations to the ThT signals observed, binding analyses between the corresponding acetylated peptides of identical length with anionic liposomes were carried out using Surface Plasmon Resonance (SPR) (FIG. 8). No correlation was observed between peptide affinity for liposomes and aggregation of the corresponding palmitoylated peptide. Combined, these results suggest that specific interactions between peptide side-chains and the liposome surface do not play a significant role in modulating the aggregation of N- and C-terminal di-palmitoylated liposomal peptides.

A5 Liposome Surface Charge Modulates Peptide Aggregation

Next a series of liposomes were prepared using different molar ratios of the phospholipids 1,2-dimyristoyl-sn-glycero-3-phosphocholine (DMPC) and 1,2-dimyristoyl-sn-glycero-3-[phosphor-rac-(1-glycerol)] (DMPG), as well as the cationic phospholipid 1,2-dimyristoyl-3-trimethylammonium-propane (DMTAP) (Table 3, formulations A-L), in order to explore whether the liposome surface charge could influence the conformation of anionic Palm1-15 (pI 5.2) or cationic mutant Palm1-15(E3K, D7K, E11K) (pI 10.0). Cholesterol content was maintained at a cholesterol/phospholipid molar ratio of 7:10. Liposomes lacking peptide (formulations M, N and O) were prepared as negative controls. Analysis by ThT fluorescence revealed much lower fluorescence ($B_{max}$) for liposomes containing either Palm1-15 or mutant Palm1-15(E3K, D7K, E11K) when the liposomes displayed greater positive zeta potential. For liposomes lacking peptide only minimal fluorescence was observed. Apparent binding constants ($K_d$'s) were determined in order to determine whether the lower ThT fluorescence in the presence of cationic liposomes was due to lower affinity resulting from electrostatic repulsion between ThT and positively charged liposomes (Table 3). The resulting binding curves revealed similar apparent $K_d$ values for different liposome formulations composed of the same peptide (Table 3 formulations A-F, and G-L) indicating that charge does not weaken the ThT binding affinity. The lower affinity of ThT for liposomes containing cationic peptide Palm1-15(E3K, D7K, E11K) compared with liposomal Palm1-15 may explain the slightly lower ThT fluorescence observed for the liposome formulations containing Palm1-15(E3K, D7K, E11K). In order to confirm these observations, magic-angle spinning (MAS)-NMR spectroscopy was performed using Palm1-15 uniformly labelled with $^{13}C/^{15}N$ at Ala-2, Ser-9 and Gly-10 (Palm1-15 (ASG)). When Palm1-15(ASG) was incorporated into anionic liposomes, $^{13}C$ double quantum (DQ) experiments revealed a significant population of β-sheet aggregates as shown by distinctive chemical shifts of the Cα position of Ser-9 and O13 position of Ala-2 (FIG. 4). On the other hand when Palm1-15(ASG) was incorporated into cationic liposomes, a significant decrease in signal intensity was observed for the Cα of Ser-9 indicative of an increase in mobility. In addition, an upfield shift in the signal of Ala-2 Cβ was observed along with a significant reduction in signal intensity consistent with a decrease in the proportion of peptide engaged in β-sheets. This result further confirms that the intensity of the ThT signal is due to differences in extent of aggregation and not due to differences in binding affinities for liposomes. Together, these results show that β-sheet aggregation of N- and C-terminal di-palmitoylated peptides occurs to a greater extent upon incorporation into anionic rather than cationic liposomes, independent of the peptide charge.

A6 Peptide Lipidation Pattern Modulates Peptide Aggregation

Next we decided to investigate the role of the palmitoyl chains upon the conformation of Palm1-15 peptide embedded within liposomal bilayers. A series of palmitoylated peptides were synthesized (Table 4) in which both the number and position of lipid anchors was varied. These peptides were incorporated into liposomes, and their conformations analyzed using both ThT fluorescence and CD spectroscopy. Liposomal peptide Palm1-15(4C) containing 4 palmitic chains on the peptide C-terminus showed a much higher ThT fluorescence emission ($B_{max}$) than peptide Palm1-15 (ACI-24) or peptide Palm1-15(2C) (Table 5), indicating that the C-terminal tetra-palmitoylated peptide has a greater tendency to form β-sheet aggregates. Importantly the apparent $K_d$ values for ThT binding to Palm1-15 or to Palm1-15(4C) were similar (Table 5). This shows that the increase in $B_{max}$ for Palm1-15(4C) compared with Palm1-15 (2N2C) cannot be explained simply by a difference in binding affinity of ThT. Palm1-15(2C) peptide gave rise to a similar fluorescence signal as Palm1-15 (2N2C), whereas the peptide Palm1-15(1N1C) containing 1 palmitic chain on both the N- and C-termini was only very weakly fluorescent upon addition of ThT. The latter showed significantly lower binding affinity to ThT consistent with a non-aggregated conformation (Table 5). Similarly, C-terminally mono-palmitoylated liposomal peptide Palm1-15(1C) showed only a very low signal compared to liposomal peptide Palm1-15 (ACI-24).

CD spectroscopic analyses of these liposomes were performed to measure the peptide secondary structure. Liposomal peptides Palm1-15(4C) and Palm1-15(2C) showed classical β-sheet CD spectra with minimum absorption at ~220 nm, and crossing the x-axis at ~214 nm similar to ACI-24 (FIG. 5a). Interestingly, the spectrum of di-palmitoylated Aβ$_{1-15}$ peptide Palm1-15 (1N1C) showed an extended β-strand conformation by CD, but did not show any fluorescence in the presence of ThT. This highlights the need to measure both peptide secondary structure (by CD) as well as peptide quaternary structure (by ThT fluorescence). It therefore appears that peptide Palm1-15(1N1C) adopts an extended β-strand conformation but is insufficiently aggregated to enable Thioflavin T to bind. In contrast, mono-palmitoylated peptide Palm1-15(1C) shows a distinct CD spectrum with a minimum at ~215 nm, and crossing the x-axis at ~207 nm consistent with a mixture of random coil and β-sheet conformations.

Next, the effect of replacing the palmitoyl anchors with shorter homologs was investigated. To this end a series of liposomes were prepared containing either dodecanoyl, octanoyl or butanoyl lipid chains replacing those of palmitoyl in Pal1-15 peptide (Table 4). ThT fluorescence measurements showed a substantial decrease in fluorescence upon reducing the peptide lipid anchor chain length from dodecanoyl (C12), to octanoyl (C8) and to butanoyl (C4) whereupon no fluorescence could be observed (Table 5). Analysis of peptide secondary structure by CD spectroscopy likewise revealed that the liposomal vaccine containing octanoyl lipid anchor chains had reduced ellipticity at 220 nm compared with the longer dodecanoyl analog. Likewise the peptide containing butanoyl chains did not show any negative ellipticity at 220 nm consistent with a lack of secondary structure (FIG. 5b).

In summary, these results show that both the conformation and extent of β-sheet aggregation of palmitoylated peptides is strongly dependent upon the number and length of lipid chains at the peptide termini, suggesting that hydrophobic association of lipid chains is a key driver of peptide aggregation.

A7 Distinct Small Molecules Modify Peptide Aggregation Post-Liposome Assembly

Since we observed disaggregation of the β-sheet aggregates of liposomal Palm1-15 with Cu(II) we decided also to explore whether the addition of small molecules which have been reported to dis-assemble Aβ aggregates could also modify the aggregation-state of Palm1-15 embedded within the liposomal bilayer. For this, Tannic acid, Rosmarinic acid and Methylene Blue were incubated with ACI-24 and the ThT fluorescence emission monitored. A decrease of fluorescence was observed upon addition of all compounds, with most efficient disaggregation observed upon addition of Methylene Blue (FIG. 9). When added to the β-sheet aggregates of the unrelated peptide sequence scPalm15 a similar fluorescence decrease was observed (FIG. 9) showing that β-sheet disaggregation occurs independent of peptide sequence.

A8 Peptide Aggregation Determines Immune Response Specificity

In order to study the relationship between the aggregation-state of liposomal peptide immunogens and the binding specificity of the corresponding polyclonal antibodies generated in vivo, the liposomal vaccine ACI-24 containing Palm1-15 peptide was prepared, characterized (see General Methodology, section C and D, for details), injected into mice and the IgG titers determined by ELISA. To analyze the conformational specificity of the polyclonal antibody response, $A\beta_{1-42}$ was allowed to partially aggregate and subsequently fractionated by size-exclusion chromatography (SEC) to give conformationally pure monomeric random coil and oligomeric β-sheet fractions (FIG. 6a). The plasma taken from individual mice immunized with ACI-24 were analyzed for polyclonal binding to the different fractions of Aβ. As can be seen in FIG. 6b, ACI-24 elicits a significantly higher (P=0.002, Wilcoxon Matched-Pairs Ranks) IgG response against the $A\beta_{1-42}$ oligomeric β-sheet, compared to the unstructured $A\beta_{1-42}$ monomer fraction.

To assess whether antibodies against ACI-24 would show conformation-specific binding to the pathological β-sheet Aβ plaques, over the non-folded native healthy APP protein, ACI-24 was injected into monkeys which share 100% APP sequence homology with human APP. The binding properties of the antibodies raised against ACI-24 were then assessed using histologically prepared cryostat sections taken from human healthy and AD brain. FIG. 7 shows clearly that serum taken from ACI-24 immunized monkey stain AD human brain whereas no cross-reactivity is observed to healthy non-AD brain. Thus Palm1-15 peptide aggregation within the liposomal vaccine is critical for determining the conformational specificity of the immune response.

Tables

TABLE 1

Different peptide sequences synthesized bearing N- and C-terminal palmitoyl or acetyl chains.

| Name | Peptide | Linker |
| --- | --- | --- |
| Palm1-15<br>Acetyl1-15 | H-K(X)-K(X)-DAEFRHDSGYEVHHQ-K(X)-<br>K(X)-OH | X = Palmitoyl<br>X = Acetyl |
| Palm15-1<br>Acetyl15-1 | H-K(X)-K(X)-QHHVEYGSDHRFEAD-K(X)-<br>K(X)-OH | X = Palmitoyl<br>X = Acetyl |
| scPalm15<br>scAcetyl15 | H-K(X)-K(X)-GHEAYHSVERFDDQH-K(X)-<br>K(X)-OH | X = Palmitoyl<br>X = Acetyl |
| Palm1-9<br>Acetyl1-9 | H-K(X)-K(X)-DAEFRHDSG-K(X)-K(X)-OH | X = Palmitoyl<br>X = Acetyl |
| Palm1-5<br>Acetyl1-5 | H-K(X)-K(X)-DAEFR-K(X)-K(X)-OH | X = Palmitoyl<br>X = Acetyl |
| Palm1-15(D7K)<br>Acetyl1-15(D7K) | H-K(X)-K(X)-DAEFRH<u>K</u>SGYEVHHQ-K(X)-<br>K(X)-OH | X = Palmitoyl<br>X = Acetyl |
| Palm1-15(E3A, D7K)<br>Acetyl1-15(E3A, D7K) | H-K(X)-K(X)-DA<u>A</u>FRH<u>K</u>SGYEVHHQ-K(X)-<br>K(X)-OH | X = Palmitoyl<br>X = Acetyl |
| Palm1-15(E3K, D7K)<br>Acetyl1-15(E3K, D7K) | H-K(X)-K(X)-DA<u>K</u>FRH<u>K</u>SGYEVHHQ-K(X)-<br>K(X)-OH | X = Palmitoyl<br>X = Acetyl |
| Palm1-15(E3K, D7K, E11K)<br>Acetyl1-15(E3K, D7K, E11K) | H-K(X)-K(X)-DA<u>K</u>FRH<u>K</u>SGY<u>K</u>VHHQ-K(X)-<br>K(X)-OH | X = Palmitoyl<br>X = Acetyl |

TABLE 2

ThT binding properties of liposomal peptide constructs of different sequence. Peptides were incorporated into liposomes composed Of DMPC, DMPG, cholesterol and MPLA (molar ratio 9:1:7:0.06). Final concentration of peptides was 121 μM. For ThT binding experiments, liposomes were diluted 8-fold prior to adding ThT at different concentrations. Apparent $K_d$ and $B_{max}$ values were determined by assuming single site binding with curve fitting performed using non-linear regression analysis (Sigma Plot v. 10.0).

| Liposomal Peptide | Theoretical pI[1] | App. $K_d$ (μM) | $B_{max}$ | $B_{max}$ (% rel. ACI-24) |
|---|---|---|---|---|
| Palm1-15 | 5.2 | 2.4 | 36318 | 100 |
| Palm15-1 | 5.2 | 7.8 | 11023 | 30 |
| scPalm15 | 5.2 | 7.9 | 13844 | 38 |
| Palm1-9 | 4.5 | 1.8 | 29436 | 81 |
| Palm1-5 | 4.4 | 0.7 | 12653 | 35 |
| Palm1-15(D7K) | 6.3 | 8.8 | 21197 | 58 |
| Palm1-15(E3A, D7K) | 7.0 | 14.7 | 24854 | 68 |
| Palm1-15(E3K, D7K) | 8.5 | 12.1 | 12567 | 35 |
| Palm1-15(E3K, D7K, E11K) | 10.0 | 10.1 | 24981 | 69 |

[1]Peptide isoelectric points (pI) were calculated according to 'Protein Identification and Analysis Tools on the ExPASy Server, Gasteiger E., Hoogland C., Gattiker A.; Duvaud S., Wilkins M. R., Appel R. D., Bairoch A.; (In) John M. Walker (ed): The Proteomics Protocols Handbook, Humana Press (2005), pp. 571-607.[6]

TABLE 3

Composition of different liposome formulations analysed for zeta potential and ThT fluorescence.

| Liposome construct | Peptide Palm1-15 | Peptide Palm1-15 (E3K, D7K, E11K) | DMPC | DMPG | DMTAP | Cholesterol | MPLA | Zeta potential (mV) | App $K_d$ (μM) | $B_{max}$ |
|---|---|---|---|---|---|---|---|---|---|---|
| A | 0.1 | 0 | 0 | 10 | 0 | 7 | 0.06 | −46.6 | 1.2 | 56024 |
| B | 0.1 | 0 | 5 | 5 | 0 | 7 | 0.06 | −22.0 | 0.7 | 28958 |
| C | 0.1 | 0 | 9 | 1 | 0 | 7 | 0.06 | −16.3 | 2.4 | 36318 |
| D | 0.1 | 0 | 9 | 0 | 1 | 7 | 0.06 | 8.4 | 1.0 | 19121 |
| E | 0.1 | 0 | 5 | 0 | 5 | 7 | 0.06 | 29.3 | 6.3 | 22055 |
| F | 0.1 | 0 | 0 | 0 | 10 | 7 | 0.06 | 40.5 | 8.7 | 10775 |
| G | 0 | 0.1 | 0 | 10 | 0 | 7 | 0.06 | −47.2 | 23.0 | 36099 |
| H | 0 | 0.1 | 5 | 5 | 0 | 7 | 0.06 | −42.8 | 34.9 | 22192 |
| I | 0 | 0.1 | 9 | 1 | 0 | 7 | 0.06 | −15.4 | 10.1 | 24981 |
| J | 0 | 0.1 | 9 | 0 | 1 | 7 | 0.06 | 4.7 | 21.8 | 6280 |
| K | 0 | 0.1 | 5 | 0 | 5 | 7 | 0.06 | 26.6 | 43.6 | 5466 |
| L | 0 | 0.1 | 0 | 0 | 10 | 7 | 0.06 | 40.4 | 47.3 | 2379 |
| M | 0 | 0 | 0 | 10 | 0 | 7 | 0.06 | −43.9 | 21.2 | 4767 |
| N | 0 | 0 | 9 | 1 | 0 | 7 | 0.06 | −15.3 | 74.6 | 1481 |
| O | 0 | 0 | 0 | 0 | 0 | 7 | 0.06 | 51.0 | 121.0 | 1306 |

Molar ratios of Palm1-15 or cationic mutant Palm1-15(E3K, D7K, E11K) formulated with different lipid compositions to form liposome constructs A-L and corresponding empty liposomes M-O lacking peptide. Peptide was added to give a final concentration of 121 μM. For ThT binding experiments, liposomes were diluted 8-fold in PBS prior to adding ThT at different concentrations. $B_{max}$ and apparent $K_d$ values were determined by assuming single site binding with curve fitting performed using non-linear regression analysis (Sigma Plot v. 10.0). Zeta potential values are expressed as the average of 3 readings.

TABLE 4

Synthesized lipopeptides with different lipidation patterns.

| Name | Peptide |
|---|---|
| Palm1-15(4C) | H-DAEFRHDSGYEVHHQ-K(Palm)-K(Palm)-K(Palm)-K(Palm)-OH |
| Palm1-15(2C) | H-DAEFRHDSGYEVHHQ-K(Palm)-K(Palm)-OH |
| Palm1-15(1N1C) | H-K(Palm)-DAEFRHDSGYEVHHQ-K(Palm)-OH |
| Palm1-15(1C) | H-DAEFRHDSGYEVHHQ-K(Palm)-OH |
| Dodecyl1-15 | H-K(Dodecanoyl)-K(Dodecanoyl)-DAEFRHDSGYEVHHQ-K(Dodecanoyl)-K(Dodecanoyl)-OH |
| Octyl1-15 | H-K(Octanoyl)-K(Octanoyl)-DAEFRHDSGYEVHHQ-K(Octanoyl)-K(Octanoyl)-OH |
| Butyl1-15 | H-K(Butanoyl)-K(Butanoyl)-DAEFRHDSGYEVHHQ-K(Butanoyl)-K(Butanoyl)-OH |

TABLE 5

ThT binding properties of liposomal peptide constructs with different lipidation patterns. ThT binding properties of liposomal peptide constructs Palm1-15, Palm1-15(4C), Palm1-15(1N1C), Palm1-15(2C), Palm1-15(1C), Dodecyl 1-15, Octyl 1-15 and Butyl 1-15 in which the position and number or length of lipid chains differ. For ThT binding experiments, liposomes were diluted 8-fold prior to adding ThT at different concentrations. Apparent $K_d$ and $B_{max}$ values were determined by assuming single site binding with curve fitting performed using non-linear regression analysis (Sigma Plot v. 10.0).

| Liposomal Peptide | App. $K_d$ (µM) | $B_{max}$ (8-fold dilution) | $B_{max}$ (50-fold dilution) |
|---|---|---|---|
| Palm1-15 | 2.4 | 36318 | 8140 |
| Palm1-15(4C) | 1.5 | — | 31756 |
| Palm1-15(1N1C) | 35.1 | 2488 | — |
| Palm1-15(2C) | 4.3 | 31898 | — |
| Palm1-15(1C) | 5.6 | 7093 | — |
| Dodecyl 1-15 | 1.2 | 26415 | — |
| Octyl 1-15 | 5.8 | 9184 | — |
| Butyl 1-15 | 7.3 | 476 | — |

REFERENCE LIST

Alving et al., Infect. Immun. 60:2438-2444, 1992

Fieser, T. M. et al., "Influence of protein flexibility and peptide conformation on reactivity of monoclonal anti-peptide antibodies with a protein alpha-helix," Proc. Natl. Acad. Sci. U.S.A. 84, 8568 (1987).

Gasteiger E., Hoogland C., Gattiker A., Duvaud S., Wilkins M. R., Appel R. D., Bairoch A 'Protein Identification and Analysis Tools on the ExPASy Server'; (In) John M. Walker (ed): The Proteomics Protocols Handbook, Humana Press (2005), pp. 571-607.

Gill et al., Nature Med. 9: 589-595 (2003)

Hodgson et al., Bio/Technology, 9:421 (1991)

Khaw, B. A. et al. J. Nucl. Med. 23:1011-1019 (1982)

Lu, S. M. & Hodges, R. S., "A de novo designed template for generating conformation-specific antibodies that recognize alpha-helices in proteins," J. Biol. Chem. 277, 23515 (2002).

Muhs, A. et al., "Liposomal vaccines with conformation-specific amyloid peptide antigens define immune response and efficacy in APP transgenic mice," Proc. Natl. Acad. Sci. U.S.A. 104, 9810 (2007).

O'Nuallain, B. & Wetzel, R., "Conformational Abs recognizing a generic amyloid fibril epitope," Proc. Natl. Acad. Sci. U.S.A. 99, 1485 (2002).

Papanastassiou et al., Gene Therapy 9: 398-406 (2002)

Queen et al., Proc. Natl Acad Sci USA, 8, 6:10029-10032 (1989)

Rousseaux et al. Methods Enzymology, 121:663-69, Academic Press, 1986

Schmechel, A. et al., "Alzheimer beta-amyloid homodimers facilitate A beta fibrillization and the generation of conformational antibodies," J. Biol. Chem. 278, 35317 (2003).

Wagner et al (2002) Journal of Liposome Research Vol 12(3), pp 259-270

Patent Literature

WO/2008/061795
WO/2008/061796
WO 2007068411
U.S. Patent Publication No. 2002/0038086
U.S. Patent Publication No. 2003/0083299
U.S. Patent Application Publication No. 20020025313
U.S. Patent Application Publication No. 20040204354
U.S. Patent Application Publication No. 20040131692
U.S. Patent Application Publication No. 2002/0065259
U.S. Patent Application Publication No 2003/0162695
U.S. Patent Application Publication No 2005/0124533
U.S. Patent Application Publication No. 2005/0089473
U.S. Patent Application Publication No. 2003/0073713
U.S. Patent Application Publication No. 2003/0129186
U.S. Pat. No. 5,004,697
U.S. Pat. No. 5,112,596
U.S. Pat. No. 5,268,164
U.S. Pat. No. 5,506,206
U.S. Pat. No. 5,686,416

EMBODIMENTS

A first embodiment of the invention relates to a method of preparing an immunogenic construct for generating an immune response in an animal or a human, wherein said immunogenic construct comprises a peptide molecule and a hydrophobic moiety covalently bound to the C- and/or N-terminal part of the peptide molecule, which peptide molecule is anchored into the lipid membrane of a liposomal carrier via said hydrophobic moiety, said method comprising modulating the secondary and/or quaternary conformation of said liposome bound peptide molecule, comprising a. adding or removing from a liposomal solution or composition metal ions which are capable of disrupting peptide-liposome or peptide-peptide stabilizing interactions; and/or b. changing the net surface potential of the Liposome by increasing or decreasing in the lipid bilayer of the liposome the proportion of anionic or cationic lipids; and/or c. varying the total number of hydrophobic moieties bound to the peptide molecule and/or the number and/or position of the sites on the peptide molecule, where the hydrophobic moieties become covalently bound to the peptide molecule; and/or d. adding small molecules to a liposomal solution or composition which are capable of either disaggregating β-sheet structures or promoting aggregation to form β-sheet structures and/or.

e. varying the length of hydrophobic moieties bound to the peptide

Embodiment 2 of the invention relates to the method of embodiment 1, wherein said immune response is a conformation-specific immune response.

Embodiment 3 of the invention relates to the method of embodiments 1 or 2, wherein the quaternary structure of the peptide molecule is modulated such as to increase the extent of β-sheet aggregation by removing or inactivating metal ions, which are capable of disrupting peptide-liposome or peptide-peptide stabilizing interactions.

Embodiment 4 of the invention relates to the method of embodiment 3, wherein a metal chelating agent is added to a liposomal solution or composition.

Embodiment 5 of the invention relates to the method of any of the preceding embodiments, wherein the quaternary structure of the peptide molecule is modulated such as to enhance the formation of β-sheet aggregates by adding compounds which are capable of stabilising the formation of β-sheet aggregates.

Embodiment 6 of the invention relates to the method of embodiment 5, wherein said compound is selected from heparin, myo-inositol, glycogen or ellagic acid.

Embodiment 7 of the invention relates to the method of any of the preceding embodiments, wherein secondary structure of the peptide molecule is modulated to increase the extent of β-sheet aggregation by increasing the net negative surface potential of the liposome.

Embodiment 8 of the invention relates to the method of embodiment 7, wherein the net negative surface potential of the liposome is increased from >+35 mV to at least <0 mV, particularly to at least <−10 mV, particularly to at least <−40 mV, in PBS.

Embodiment 9 of the invention relates to the method of embodiments 7 or 8, wherein the increase in net negative surface potential is accomplished by exchanging a proportion of cationic lipids in the lipid bilayer of the liposome with an equal proportion of anionic lipids.

Embodiment 10 of the invention relates to the method of any of embodiments 7-9, wherein the extent of β-sheet aggregation is increased by 50%-100%, particularly by 80-100%.

Embodiment 11 of the invention relates to the method of any of embodiments 1-6, wherein secondary structure of the peptide molecule is modulated to decrease the extent of β-sheet aggregation by decreasing the net negative surface potential of the liposome.

Embodiment 12 of the invention relates to the method of embodiment 11, wherein the net negative surface potential of the liposome is decreased from <−10 mV to at least >0 mV, particularly to at >+10 mV, particularly to at least >+35 mV, in PBS.

Embodiment 13 of the invention relates to the method of embodiments 11 or 12, wherein the decrease in net negative surface potential is accomplished by exchanging a proportion of anionic lipids in the lipid bilayer of the liposome with an equal proportion of cationic lipids.

Embodiment 14 of the invention relates to the method of embodiment 9, wherein said anionic lipids are selected from the group consisting of:
  i. diacyl-phospholipids with headgroups phosphatidyl glycerol, phosphatidyl serine, phosphatidyl inositol, L-α-phosphatidylinositol-4-phosphate or phosphatidic acid;
  ii. lyso-phospholipids with headgroups phosphatidyl glycerol, phosphatidyl serine or phosphatidic acid, and
  iii. cardiolipin, dilyso-cardiolipin, monolyso-cardiolipin.

Embodiment 15 of the invention relates to the method of embodiment 13, wherein said cationic lipids are selected from the group consisting of:
  i. diacyl-phospholipids with headgroups 3-trimethylammonium-propane, 3-dimethylammonium-propane, 3-ethylphosphocholine or 3-phosphatidylethanolamine.
  ii. D-erythro-sphingosine, dimethyldioctadecylammonium bromide, N-[1-(2,3-dimyristyloxy)propyl]-N,N-dimethyl-N-(2-hydroxyethyl) ammonium bromide, N,N,N-trimethyl-2-bis[(1-oxo-9-octadecenyl)oxy]-(Z,Z)-1-propanaminium metzhyl sulfate or 3β-[N—(N',N'-dimethylaminoethane)-carbamoyl]cholesterol hydrochloride Embodiment 16 of the invention relates to the method of embodiments 14 or 15, wherein the lipid chains attached to the headgroup can
  be saturated or unsaturated,
  vary in length from (CH2)n wherein n is between 3 and 24, and
  be symmetrically or asymmetrically substituted
  and are incorporated into the liposomal bilayer.

Embodiment 17 of the invention relates to the method of any one of the preceding embodiments, wherein the secondary structure of the peptide molecule is modulated by the total number and/or position of the hydrophobic moieties covalently bound to the N- and/or the C-terminus of the peptide molecule.

Embodiment 18 of the invention relates to the method of embodiment 17, wherein the secondary structure of the peptide molecule is modulated by increasing the total number of the hydrophobic moieties covalently bound to the N- and/or the C-terminus of the peptide molecule.

Embodiment 19 of the invention relates to the method of embodiments 17 or 18, wherein at least two, at least three, at least four hydrophobic moieties are covalently bound to the N- and/or the C-terminus of the peptide molecule.

Embodiment 20 of the invention relates to the method of embodiment 19, wherein at least 4 hydrophobic moieties are covalently bound to the N- and/or the C-terminus of the peptide molecule.

Embodiment 21 of the invention relates to the method of embodiments 1 or 2, wherein the quaternary structure of the peptide molecule is modulated by disaggregating the β-sheet aggregates.

Embodiment 22 of the invention relates to the method of embodiment 21, wherein disaggregation is accomplished by adding a small molecule capable of disaggregating β-sheet aggregates.

Embodiment 23 of the invention relates to the method of embodiment 21, wherein disaggregation is accomplished by adding metal ions which are capable of disrupting peptide-liposome or peptide-peptide stabilizing interactions.

Embodiment 24 of the invention relates to the method of embodiment 23, wherein said metal ion is Cu(II) or Zn(II).

Embodiment 25 of the invention relates to the method according to any of the preceding embodiments, wherein said hydrophobic moiety is a fatty acid, a triglyceride, diglyceride, steroid, sphingolipid, glycolipid or a phospholipid.

Embodiment 26 of the invention relates to the method of embodiment 25, wherein the hydrophobic moiety is a fatty acid, particularly a fatty acid with a carbon backbone of at least 3 carbon atoms or of at least 4 carbon atoms.

Embodiment 27 of the invention relates to the method of embodiment 25, wherein the hydrophobic moiety is a fatty acid, particularly a fatty acid with a carbon backbone of at least 6 carbon atoms.

Embodiment 28 of the invention relates to the method of embodiment 26, wherein the hydrophobic moiety is palmitic acid.

Embodiment 29 of the invention relates to the method according to any of the preceding embodiments, wherein the peptide molecule is a peptide derived from an amyloid protein or amyloid-like protein such as, for example prion protein, tau protein, alpha-synuclein, huntingtin.

Embodiment 30 of the invention relates to the method according to any of the preceding embodiments, wherein the Aβ peptide is derived from the N-terminus of an amyloid protein or amyloid-like protein.

Embodiment 31 of the invention relates to the method according to any of the preceding embodiments, wherein said Aβ peptide is an $A\beta_{1-30}$; an $A\beta_{1-20}$; an $A\beta_{1-16}$; an $A\beta_{1-15}$; an $A\beta_{1-9}$ Embodiment 32 of the invention relates to the method according to any of the preceding embodiments, wherein the peptide molecule is represented by a phospho-peptide mimicking a major pathological phospho-epitope of protein tau.

Embodiment 33 of the invention relates to the method according to any of the preceding embodiments, wherein said tau protein is a human protein.

Embodiment 34 of the invention relates to the method according to the preceding embodiment, wherein said tau protein has an amino acid sequence identity

- to SEQ ID NO: 2 of at least 95%, and has substantially the same immunogenic activity as said antigenic peptide of SEQ ID NO: 2, wherein the amino acid residue corresponding to amino acid residue 18 (P-Tyr$_{18}$) of SEQ ID NO: 2 is phosphorylated (T1);
- to SEQ ID NO: 3 of at least 95%, and has substantially the same immunogenic activity as said antigenic peptide of SEQ ID NO: 3, wherein at least one, particularly at least 2 of amino acid residues corresponding to amino acid residues 212 (P-Thr$_{212}$) and 214 (P-Ser$_{214}$) of SEQ ID NO: 3 are phosphorylated;
- to SEQ ID NO: 4 of at least 95%, and has substantially the same immunogenic activity as said antigenic peptide of SEQ ID NO: 4, wherein at least one, particularly at least 2 of amino acid residues corresponding to amino acid residues 202 (P-Ser$_{202}$) and 205 (P-Thr$_{205}$) of SEQ ID NO: 4 are phosphorylated;
- to SEQ ID NO: 5 of at least 95%, and has substantially the same immunogenic activity as said antigenic peptide of SEQ ID NO: 5, wherein at least one, but especially all of amino acid residues corresponding to amino acid residues 396 (P-Ser$_{396}$) and 404 (P-Ser$_{404}$) of SEQ ID NO: 5 are phosphorylated;
- to SEQ ID NO: 6 of at least 95%, and has substantially the same immunogenic activity as said antigenic peptide of SEQ ID NO: 6, wherein at least one, but especially all of amino acid residues corresponding to amino acid residues 404 (P-Ser$_{404}$) and 409 (P-Ser$_{409}$) of SEQ ID NO: 6 are phosphorylated; or
- to SEQ ID NO: 7 of at least 95%, and has substantially the same immunogenic activity as said antigenic peptide of SEQ ID NO: 7, wherein at least one, particularly at least 2, particularly a least 3, but especially all of amino acid residues corresponding to amino acid residues 202 (P-Ser$_{202}$), 205 (P-Thr$_{205}$), 212 (P-Thr$_{212}$), and 214 (P-Ser$_{214}$) of SEQ ID NO: 7 are phosphorylated.

Embodiment 35 of the invention relates to the method according to the preceding embodiment, wherein said tau protein has an amino acid sequence of SEQ ID NO: 2; SEQ ID NO: 3; SEQ ID NO: 4; SEQ ID NO: 5; SEQ ID NO: 6 or SEQ ID NO: 7.

Embodiment 36 of the invention relates to an immunogenic construct comprising a peptide molecule anchored into the membrane of a liposome via a hydrophobic moiety prepared by a method according to any of the preceding embodiments or a composition comprising said immunogenic construct.

Embodiment 37 of the invention relates to the immunogenic construct or composition of embodiment 36, wherein the number of hydrophobic anchor molecules at one end of the peptide molecule is totaling 1 anchor molecule, particularly 2 anchor molecules, particularly 3 anchor molecules, particularly 4 anchor molecules.

Embodiment 38 of the invention relates to the immunogenic construct or composition of embodiments 36 or 37, wherein said hydrophobic moiety is a moiety selected from the group consisting of a fatty acid, a triglyceride, diglyceride, steroid, sphingolipid, glycolipid or a phospholipid.

Embodiment 39 of the invention relates to the immunogenic construct or composition of embodiment 37, wherein said hydrophobic moiety is a fatty acid, particularly a fatty acid of at least 6 carbon atoms, particularly at least 12 carbon atoms, particularly at least 14 carbon atoms, particularly at least 18 carbon atoms.

Embodiment 40 of the invention relates to the immunogenic construct or composition of any of embodiments 36-39, wherein the number of hydrophobic anchor molecules at one end of the peptide molecule is totaling 2 anchor molecules, particularly 3 anchor molecules, particularly 4 anchor molecules.

Embodiment 41 of the invention relates to the immunogenic construct or composition of any of the preceding embodiments, which is free or substantially free of metal ions.

Embodiment 42 of the invention relates to the immunogenic construct or composition of any of the preceding embodiments comprising one or more compounds which are capable of stabilising the formation of β-sheet aggregates.

Embodiment 43 of the invention relates to the immunogenic construct or composition of embodiment 42, wherein said compound is a compound selected from the group consisting of heparin, myo-inositol, glycogen and ellagic acid.

Embodiment 44 of the invention relates to the peptide molecule or composition of any of the preceding embodiments wherein the liposomes have a net negative surface potential of at least <–0 mV, particularly of at least <–10 mV, particularly of at least <–40 mV, in PBS.

Embodiment 45 of the invention relates to tn immunogenic construct comprising a peptide molecule and a hydrophobic moiety covalently bound to the C- and/or N-terminal part of the peptide molecule anchored into the lipid membrane of a liposomal carrier via said hydrophobic moiety, which immunogenic construct shows an enhanced extent of β-sheet aggregation and comprises at least two of the following features:

- a net negative surface potential of the liposome of at least <0 mV, particularly of at least <–10 mV, particularly of at least <–40 mV, in PBS; a length of the individual hydrophobic anchor molecule of at least 6 carbon atoms, particularly at least 12 carbon atoms, particularly at least 14 carbon atoms, particularly at least 18 carbon atoms;
- a number of hydrophobic anchor molecules at one end of the peptide molecule totaling 2 anchor molecules, particularly 3 anchor molecules, particularly 4 anchor molecules;
- one or more compounds which are capable of stabilising the formation of β-sheet aggregates;
- no metal ions, particularly due to the presence of a metal chelating agent.

Embodiment 46 of the invention relates to the immunogenic construct or composition of any of embodiments 37 or 38, wherein said hydrophobic moiety is a fatty acid, of less than 4 carbon atoms, particularly less than 3 carbon atoms, particularly less than 2 carbon atoms.

Embodiment 47 of the invention relates to the immunogenic construct or composition any of embodiments 37 or 38 and embodiment 46, wherein the liposomes have a net negative surface potential of at least >0 mV, particularly of at least >+10 mV, particularly of at least >+35 mV, in PBS.

Embodiment 48 of the invention relates to the immunogenic construct or composition of any of embodiments 37 or 38 and 46-47, which comprises metal inns, particularly Cu(II) and/or Zn(II) and/or a small molecule capable of disaggregating β-sheet aggregates.

Embodiment 49 of the invention relates to tn immunogenic construct comprising a peptide molecule and a hydrophobic moiety covalently bound to the C- and/or N-terminal part of the peptide molecule, which peptide molecule is anchored into the lipid membrane of a liposomal carrier via said hydrophobic moiety, which immunogenic construct shows an reduced extent of β-sheet aggregation and comprises at least two of the following features:

a net negative surface potential of the liposome of at least at least >0 mV, particularly of at least >+10 mV, particularly of at least >+35 mV, in PBS;

a length of the individual hydrophobic anchor molecule of less than 4 carbon atoms, particularly less than 3 carbon atoms, particularly less than 2 carbon atoms;

a number of hydrophobic anchor molecules at one end of the peptide molecule totaling 1 anchor molecule;

metal ions, particularly Cu(II) and/or Zn(II) and/or small molecules capable of disaggregating β-sheet aggregates.

Embodiment 50 of the invention relates to the immunogenic construct or composition of any of the preceding embodiments, wherein the peptide molecule is a peptide derived from an amyloid protein or amyloid-like protein such as, for example prion protein, tau protein, alpha-synuclein, huntingtin.

Embodiment 51 of the invention relates to the immunogenic construct or composition of embodiment 52, wherein the peptide molecule is a peptide derived from a tau protein, particularly a human tau protein, particularly a molecule comprising a phosphopeptide mimicking a major pathological phospho-epitope of protein tau.

Embodiment 52 of the invention relates to the immunogenic construct or composition of any of the preceding embodiments for use in the preparation of a pharmaceutical composition comprising the liposome-embedded peptide molecule according to any of the preceding embodiments together with a pharmaceutically acceptable excipient or carrier.

Embodiment 53 of the invention relates to the immunogenic construct or composition of any of the preceding embodiments for use in the preparation of conformation specific antibody or a conformation-specific antibody fragment.

Embodiment 54 of the invention relates to a method of producing a conformation specific antibody or a conformation-specific antibody fragment by administering to an animal or a human a peptide molecule or a composition according to any of the preceding embodiments such that an immune response is triggered in said animal or human and an antibody produced and obtaining said antibody.

Embodiment 55 of the invention relates to a conformation specific antibody or a conformation-specific antibody fragment produced by the method of embodiment 54.

Embodiment 56 of the invention relates to the conformation specific antibody or a conformation-specific antibody fragment of embodiment 55, wherein said antibody is a polyclonal antibody.

Embodiment 57 of the invention relates to a conformation specific antibody or a conformation-specific antibody fragment of embodiment 55, wherein said antibody is a monoclonal antibody.

Embodiment 58 of the invention relates to a conformation-specific antibody or a conformation specific antibody fragment of any of the preceding embodiments, wherein said antibody or antibody fragment is capable of specifically recognizing pathological β-sheet multimers of a target peptide and showing no or substantially no cross-reactivity with the physiologically active peptide conformer.

Embodiment 59 of the invention relates to a pharmaceutical composition comprising a liposome-embedded peptide molecule or composition according to any of the preceding embodiments, or a conformation-specific antibody or a conformation specific antibody fragment according to any of the preceding embodiments, together with a pharmaceutically acceptable excipient or carrier.

Embodiment 60 of the invention relates to a pharmaceutical composition comprising a liposome-embedded peptide molecule or composition according to any of the preceding embodiments, or a conformation-specific antibody or a conformation specific antibody fragment according to any of the preceding embodiments, together with a pharmaceutically acceptable excipient or carrier for use as a medicament in the treatment of a disease or disorder.

Embodiment 61 of the invention relates to the pharmaceutical composition of embodiments 59 or 60 for use in the treatment or prevention of a disease or disorder associated with the aggregation of peptides, particularly peptides associated to cell membranes in an animal or a human patient in need of such a treatment.

Embodiment 62 of the invention relates to the pharmaceutical composition of embodiment 61, wherein said disease or disorder is a proteopathy, a disease involving protein misfolding and/or a disease involving protein accumulation or aggregation.

Embodiment 63 of the invention relates to the pharmaceutical composition of any of the preceding embodiments for use in the treatment or prevention of a disease or disorder selected from the group consisting of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, Familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis, Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, seminal vesicle amyloid, seipinopathy, senile systemic amyloidosis, serpinopathy, sickle cell disease, synucleinopathy, tauopathy, and type 2 diabetes, in an animal or human patient in need of such a treatment.

Embodiment 64 of the invention relates to a test kits for detection and diagnosis of a proteinopathy comprising antibodies according to any of embodiments 55-58.

Embodiment 65 of the invention relates to a method of obtaining compounds capable of interfering with the aggregation of peptides, particularly peptides associated to cell membranes, comprising contacting the compound to be tested with a peptide molecule provided anchored into the membrane of a liposome via a hydrophobic moiety covalently bound to the C- and/or N-terminal part of the peptide molecule;

determining the β-sheet aggregation status of the membrane embedded peptide molecules before and after contact with the test compound;

calculating the β-sheet disaggregation activity of the test compound; and obtaining the test compound with the desired activity.

Embodiment 66 of the invention relates to a method according to embodiment 65, wherein the β-sheet aggregation status of the membrane anchored peptide molecule is determined by measuring fluorescence of Thioflavin T (ThT) upon addition of the liposome anchored peptide molecule.

Embodiment 67 of the invention relates to a compound obtained by a method of embodiments 65 or 66, which compound is capable of interfering with the aggregation of peptides, particularly peptides associated to cell membranes.

Embodiment 68 of the invention relates to the compound of embodiment 67 for use in the treatment or prevention of a disease or disorder associated with the aggregation of peptides, particularly peptides associated to cell membranes in an animal or a human patient in need of such a treatment.

Embodiment 69 of the invention relates to the compound of embodiment 68, wherein said disease or disorder is a proteopathy, a disease involving protein misfolding and/or a disease involving protein accumulation or aggregation.

Embodiment 70 of the invention relates to the compound of any of the preceding embodiments for use in the treatment or prevention of a disease or disorder selected from the group consisting of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis, Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, seminal vesicle amyloid, seipinopathy, senile systemic amyloidosis, serpinopathy, sickle cell disease, synucleinopathy, tauopathy, and type 2 diabetes, in an animal or human patient in need of such a treatment.

Embodiment 71 of the invention relates to a method for treating or preventing a disease or disorder associated with the aggregation of peptides, particularly peptides associated to cell membranes, particularly proteopathies, diseases involving protein misfolding and/or diseases involving protein accumulation comprising administering to an animal or human patient in need of such a treatment a peptide molecule; an antibody, a compound or a pharmaceutical composition according to any of the preceding embodiments.

Embodiment 72 of the invention relates to a method of embodiment 71, wherein the disease or disorder is selected from the group consisting of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, Familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis; Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, seminal vesicle amyloid, seipinopathy, senile systemic amyloidosis, serpinopathy, sickle cell disease, synucleinopathy, tauopathy, and type 2 diabetes.

Embodiment 73 of the invention relates to a method of using a peptide molecule; an antibody, a compound or a pharmaceutical composition according to any of the preceding embodiments for the preparation of a medicament for treating or preventing a disease or disorder associated with the aggregation of peptides.

Embodiment 74 of the invention relates to the method of embodiment 73, wherein said disorder is associated with the aggregation of peptides associated to cell membranes.

Embodiment 75 of the invention relates to the method according to embodiments 73 or 74 for the preparation of a pharmaceutical composition for use in treatment or prevention of AA amyloidosis, AH (heavy chain) amyloidosis, AL (light chain) amyloidosis, Alexander disease, Alzheimer's disease, amyotrophic lateral sclerosis, aortic medial amyloidosis, apoA1 amyloidosis, apoA2 amyloidosis, apoA4 amyloidosis, CADASIL, cardiac atrial amyloidosis, cataract, cerebral amyloid angiopathy, corneal lactoferrin amyloidosis, critical illness myopathy, cutaneous lichen amyloidosis, cystic fibrosis, dialysis amyloidosis, Familial amyloidotic neuropathy, familial British dementia, familial Danish dementia, familial visceral amyloidosis, fibrinogen amyloidosis, Finnish hereditary amyloidosis, frontotemporal lobar dementia, Glaucoma, hereditary cerebral hemorrhage with amyloidosis—Dutch type, hereditary cerebral hemorrhage with amyloidosis—Icelandic type, Huntington's disease and other triplet disorders, hereditary lattice corneal dystrophy, inclusion body myositis/myopathy, lysozyme amyloidosis, Mallory bodies, medullary thyroid carcinoma, Odontogenic (Pindborg) tumor amyloid, Parkinson's disease, pituitary prolactinoma, primary systemic amyloidosis, primary cutaneous amyloidosis, prion disease, pulmonary alveolar proteinosis, seminal vesicle amyloid, seipinopathy, senile systemic amyloidosis, serpinopathy, sickle cell disease, synucleinopathy, tauopathy, and type 2 diabetes.

Embodiment 76 of the invention relates to a method for diagnosing a disease or disorder involving protein misfolding and/or diseases involving protein accumulation in a subject comprising detecting the immunospecific binding of an antibody according to any of embodiments 55-58 or functional parts thereof, to an epitope of said disease-causing peptide or protein in a sample of a subject or in situ which includes the steps of bringing the sample or a specific body part or body area suspected to contain the disease-causing peptide or protein into contact with the antibody which antibody binds an epitope of the disease-causing peptide or protein;

allowing the antibody to bind to the disease-causing peptide or protein to form an immunological complex;

detecting the formation of the immunological complex, particularly such that presence or absence of the immunological complex correlates with presence or absence of the disease-causing peptide or protein; and correlating the presence or absence of the immunological complex with the presence or absence of the disease-causing peptide or protein in the sample.

Embodiment 77 of the invention relates to a method for diagnosing a predisposition to a disease or disorder involving protein misfolding and/or diseases involving protein accumulation in a subject comprising detecting the immunospecific binding of an antibody according to any of embodiments 55-58 or functional parts thereof, to an epitope of said disease-causing peptide or protein in a sample of a subject or in situ which includes the steps of
bringing the sample or a specific body part or body area suspected to contain the disease-causing peptide or protein into contact with the antibody which antibody binds an epitope of the disease-causing peptide or protein;
allowing the antibody to bind to the disease-causing peptide or protein to form an immunological complex;
detecting the formation of the immunological complex,
correlating the presence or absence of the immunological complex with the presence or absence of the disease-causing peptide or protein in the sample; and
comparing the amount of said immunological complex to a normal control value,
wherein an increase in the amount of said complex compared to a normal control value indicates that the subject is suffering from or is at risk of developing a disease or disorder involving protein misfolding and/or diseases involving protein accumulation Embodiment 78 of the invention relates to a method for monitoring minimal residual disease or disorder involving protein misfolding and/or diseases involving protein accumulation following treatment with the pharmaceutical composition of any of embodiments 59-63, wherein said method comprises:
bringing the sample or a specific body part or body area suspected to contain the disease-causing peptide or protein into contact with the antibody which antibody binds an epitope of the disease-causing peptide or protein;
allowing the antibody to bind to the disease-causing peptide or protein to form an immunological complex;
detecting the formation of the immunological complex,
correlating the presence or absence of the immunological complex with the presence or absence of the disease-causing peptide or protein in the sample; and
comparing the amount of said immunological complex to a normal control value,
wherein an increase in the amount of said complex compared to a normal control value indicates that the subject still suffers from a minimal residual disease or disorder involving protein misfolding and/or diseases involving protein accumulation.

Embodiment 79 of the invention relates to a method for predicting responsiveness of a subject being treated with the pharmaceutical composition of any of embodiments 59-63 wherein said method comprises:
bringing the sample or a specific body part or body area suspected to contain the disease-causing peptide or protein into contact with the antibody which antibody binds an epitope of the disease-causing peptide or protein;
allowing the antibody to bind to the disease-causing peptide or protein to form an immunological complex;
detecting the formation of the immunological complex,
correlating the presence or absence of the immunological complex with the presence or absence of the disease-causing peptide or protein in the sample; and
comparing the amount of said immunological complex to a normal control value,
wherein a decrease in the amount of said immunological complex indicates that the subject has a high potential of being responsive to the treatment.

Embodiment 80 of the invention relates to the method of any of embodiments 76-79, wherein the subject is a mammal.

Embodiment 81 of the invention relates to the method of embodiment 80, wherein the mammal is a human.

The invention claimed is:

1. A method of preparing a modulated immunogenic construct for generating an immune response in an animal or a human, wherein said immunogenic construct comprises a peptide molecule and a hydrophobic moiety covalently bound to the C- and/or N-terminal part of the peptide molecule, which peptide molecule is anchored into the lipid membrane of a liposomal carrier via said hydrophobic moiety, said method comprising:
   a. modulating the secondary and/or quaternary structure and the extent of β-sheet structure and/or β-sheet aggregation of the liposome-bound peptide molecule, comprising one or more of;
      i. modulating the amount of metal ions capable of disrupting peptide-liposome or peptide-peptide stabilizing interactions in the liposomal solution or composition,
      ii. changing the net surface potential of the liposome by modulating the proportion of anionic or cationic lipids in the lipid bilayer of the liposome,
      iii. varying the total number of hydrophobic moieties covalently bound to the N- and/or C-terminus of the peptide molecule such that there is a disparity in the number of hydrophobic moieties between the N- and the C-terminus, and
      iv. adding small molecules to a liposomal solution or composition which are capable of either disaggregating β-sheet structures or promoting aggregation to form β-sheet structures, and
   b. determining the extent of β-sheet structure and/or β-sheet aggregation of the liposome-bound antigenic peptide; and
   c. obtaining the modulated immunogenic construct,
   wherein the peptide molecule is a peptide derived from an amyloid protein, a tau protein, a prion protein, an alpha-synuclein protein, or a huntington protein.

2. A method of modulating the secondary and/or quaternary structure of an antigenic peptide molecule, which antigenic peptide molecule has a hydrophobic moiety covalently bound to its C- and/or N-terminus and is anchored into the lipid membrane of a liposomal carrier via said hydrophobic moiety, comprising
   a. modulating the amount of metal ions capable of disrupting peptide-liposome or peptide-peptide stabilizing interactions in the liposomal solution or composition; and/or
   b. changing the net surface potential of the liposome by modulating the proportion of anionic or cationic lipids in the lipid bilayer of the liposome; and/or
   c. varying the total number of hydrophobic moieties covalently bound to the N- and/or C-terminus of the peptide molecule such that there is a disparity in the number of hydrophobic moieties between the N- and the C-terminus; and/or
   d. adding small molecules to a liposomal solution or composition which are capable of either disaggregating β-sheet structures or promoting aggregation to form β-sheet structures,
   wherein said modulation of the secondary and/or quaternary structure leads to an increase or decrease of the extent of β-sheet structures and/or β-sheet aggregation of the liposome-bound antigenic peptide molecule, and
   wherein the antigenic peptide molecule is a peptide derived from an amyloid protein, a tau protein, a prion protein, an alpha-synuclein protein, or a huntington protein.

3. The method of claim 1, wherein said stabilizing compound is selected from:
   a. heparin, myo-inositol, glycogen or ellagic acid; and/or
   b. the net negative surface potential of the liposome is increased from >+35 mV to at least <0mV, to at least <−10 mV, or to at least <−40 mV, in PBS; or
   c. the net negative surface potential of the liposome is decreased from <−10 mV to at least >0mV, to at least >+10 mV, or to at least >+35 mV, in PBS.

4. The method of claim 3, wherein the decrease in net negative surface potential is accomplished by exchanging a proportion of anionic lipids in the lipid bilayer of the liposome with an equal proportion of cationic lipids,
   wherein said anionic lipids are selected from the group consisting of:
   i. diacyl-phospholipids with headgroups phosphatidyl glycerol, phosphatidyl serine, phosphatidyl inositol, L-α-phosphatidylinositol-4-phosphate or phosphatidic acid;
   ii. diether-phospholipids with headgroups phosphatidyl glycerol, phosphatidyl serine, phosphatidyl inositol, L-α-phosphatidylinositol-4-phosphate or phosphatidic acid;
   iii. lyso-phospholipids with headgroups phosphatidyl glycerol, phosphatidyl serine or phosphatidic acid;
   iv. cardiolipin, dilyso-cardiolipin, monolyso-cardiolipin;
   v. glycolipids, and lipopolysaccharides;
   wherein said cationic lipids are selected from the group consisting of:
   i). diacyl-phospholipids with headgroups 3-trimethylammonium-propane, 3-dimethylammonium-propane, 3-ethylphosphocholine or 3-phosphatidylethanolamine;
   ii) diether-phospholipids with headgroups 3-trimethylammonium-propane, 3-dimethylammonium-propane, 3-ethylphosphocholine or 3-phosphatidylethanolamine;
   iii) lyso-phospholipids with headgroups 3-trimethylammonium-propane, 3-dimethylammonium-propane, 3-ethylphosphocholine or 3-phosphatidylethanolamine;

iv. D-erythro-sphingosine, dimethyldioctadecylammonium bromide, N-[1-(2,3-dimyristyloxy)propyl]-N,N-dimethyl-N-(2-hydroxyethyl) ammonium bromide, N,N,N-trimethyl-2-bis[(1-oxo-9-octadecenyl)oxy]-(Z,Z)-1-propanaminium methyl sulfate and 3β-[N-(N',N'-dimethylaminoethane)-carbamoyl]cholesterol hydrochloride.

5. The method of claim 1, wherein
   a. the number of hydrophobic moieties covalently bound to the N-terminus of the peptide molecule exceeds the number of hydrophobic moieties covalently bound to the C-terminus of the peptide molecule by at least one, at least two, at least three, at least four moieties; or
   b. the number of hydrophobic moieties covalently bound to the C-terminus of the peptide molecule exceeds the number of hydrophobic moieties covalently bound to the N-terminus of the peptide molecule by at least one, at least two, at least three, at least four moieties.

6. The method of claim 1, wherein the secondary and/or quaternary conformation of the peptide molecule is modulated by disaggregating the β-sheet aggregates, which is accomplished by adding metal ions which are capable of disrupting peptide-liposome or peptide-peptide stabilizing interactions, wherein the metal ions are Cu(II) or Zn(II).

7. An immunogenic construct comprising a peptide molecule anchored into the membrane of a liposome via hydrophobic moieties covalently bound to the N-terminus, C-terminus, or both of the peptide molecule such that there is a disparity between the number of hydrophobic moieties between the N-terminus and C-terminus, or a composition comprising said immunogenic construct,
   wherein said immunogenic construct is modulated to have an increased extent of β-sheet structure and/or β-sheet aggregation of between 50%-100%, as compared prior to modulation,
   wherein the number of hydrophobic moieties covalently bound to the N-terminus of the peptide molecule exceeds the number of hydrophobic moieties covalently bound to the C-terminus of the peptide molecule by at least three, or by at least four moieties, or the number of hydrophobic moieties covalently bound to the C-terminus of the peptide molecule exceeds the number of hydrophobic moieties covalently bound to the N-terminus of the peptide molecule by at least three, or by at least four moieties, and
   wherein the peptide molecule is a peptide derived from an amyloid protein, a tau protein, a prion protein, an alpha synuclein protein, or a huntingtin protein.

8. The immunogenic construct or composition of claim 7, wherein the hydrophobic moiety is covalently bound to the C-terminal, N-terminal, or both the C-terminal and N-terminal part of the peptide molecule, wherein said immunogenic construct has been modulated to show an enhanced extent of β-sheet structure, β-sheet aggregation, or both, and comprises at least two features selected from the group consisting of:
   i. a net negative surface potential of the liposome of at least <0mV, of at least <−10 mV, or of at least <−40 mV, in PBS;
   ii. a length of the individual hydrophobic anchor molecule of at least 6 carbon atoms, at least 12 carbon atoms, at least 14 carbon atoms, or at least 18 carbon atoms;
   iii. a number of hydrophobic moieties covalently bound to the N-terminus and the C-terminus of the peptide molecule and to the C-terminus and N-terminus, respectively, of 3:0; 4:0; 4:1;
   iv. presence of one or more compounds which are capable of stabilising the formation of β-sheet aggregates; and
   v. absence of metal ions due to the presence of a metal chelating agent.

9. An immunogenic construct comprising a peptide molecule anchored into the membrane of a liposome via a hydrophobic moiety or a composition comprising said immunogenic construct, wherein the hydrophobic moiety is covalently bound to the C-terminal, N-terminal, or both the C-terminal and N-terminal part of the peptide molecule, and wherein the immunogenic construct is modulated to show an reduced extent of β-sheet aggregation and comprises at least two features selected from the group consisting of:
   i. a net negative surface potential of the liposome of at least >0mV, of at least >+10 mV, or of at least >+35 mV, in PBS;
   ii. a length of the individual hydrophobic anchor molecule of less than 4 carbon atoms, particularly less than 3 carbon atoms, particularly less than 2 carbon atoms;
   iii. a number of hydrophobic anchor molecules at one end of the peptide molecule totalling 1 anchor molecule; and
   iv. presence of Cu(II) and/or Zn(II) metal ions and/or small molecules capable of disaggregating β-sheet aggregates,
   wherein the peptide molecule is a peptide derived from an amyloid protein, a tau protein, a prion protein, an alpha-synuclein protein, or huntingtin protein.

10. The immunogenic construct or composition of claim 9, wherein said
   a. said amyloid protein is an $A\beta_{1-30}$; an $A\beta_{1-20}$; an $A\beta_{1-16}$; an $A\beta_{1-15}$; an $A\beta_{1-9}$; or any other Aβ fragment and/or truncated Aβ fragment longer than 5 amino acids; and
   b. said tau protein has an amino acid sequence identity to
      i. SEQ ID NO: 2 of at least 95%, and has substantially the same immunogenic activity as said antigenic peptide of SEQ ID NO: 2, wherein the amino acid residue corresponding to amino acid residue 18 ($P\text{-}Tyr_{18}$) of SEQ ID NO: 2 is phosphorylated;
      ii. SEQ ID NO: 3 of at least 95%, and has substantially the same immunogenic activity as said antigenic peptide of SEQ ID NO: 3, wherein at least one, or at least 2 of amino acid residues corresponding to amino acid residues 212 ($P\text{-}Thr_{212}$) and 214 ($P\text{-}Ser_{214}$) of SEQ ID NO: 3 are phosphorylated;
      iii. SEQ ID NO: 4 of at least 95%, and has substantially the same immunogenic activity as said antigenic peptide of SEQ ID NO: 4, wherein at least one, or at least 2 of amino acid residues corresponding to amino acid residues 202 ($P\text{-}Ser_{202}$) and 205 ($P\text{-}Thr_{205}$) of SEQ ID NO: 4 are phosphorylated;
      iv. SEQ ID NO: 5 of at least 95%, and has substantially the same immunogenic activity as said antigenic peptide of SEQ ID NO: 5, wherein at least one, or all of amino acid residues corresponding to amino acid residues 396 ($P\text{-}Ser_{396}$) and 404 ($P\text{-}Ser_{404}$) of SEQ ID NO: 5 are phosphorylated;
      v. SEQ ID NO: 6 of at least 95%, and has substantially the same immunogenic activity as said antigenic peptide of SEQ ID NO: 6, wherein at least one, or all of amino acid residues corresponding to amino acid residues 404 ($P\text{-}Ser_{404}$) and 409 ($P\text{-}Ser_{409}$) of SEQ ID NO: 6 are phosphorylated; or
      vi. SEQ ID NO: 7 of at least 95%, and has substantially the same immunogenic activity as said antigenic peptide of SEQ ID NO: 7, wherein at least one, particularly at least 2, particularly a least 3, or all of amino acid residues corresponding to amino acid residues 202 ($P\text{-}Ser_{202}$), 205 ($P\text{-}Thr_{205}$), 212 ($P\text{-}Thr_{212}$), and 214 ($P\text{-}Ser_{214}$) of SEQ ID NO: 7 are phosphorylated.

11. A pharmaceutical composition comprising the immunogenic construct or composition of claim 7, together with a pharmaceutically acceptable excipient or carrier.

12. A pharmaceutical composition comprising a conformation-specific antibody or a conformation-specific antibody fragment to the peptide molecule derived from the amyloid protein or tau protein of claim 10 in a therapeutically effective amount, together with a pharmaceutically acceptable excipient or carrier.

13. A conformation specific antibody or a conformation-specific antibody fragment produced by a method comprising
   a. administering to an animal or a human the immunogenic construct or the composition of claim 7 such that an immune response is induced in said animal or human and an antibody produced; and
   b. obtaining said antibody.

14. A method of obtaining compounds capable of interfering with the β-sheet structure and/or aggregation of peptides, or peptides associated to cell membranes, comprising:
   i. contacting the compound to be tested with an immunogenic construct of claim 7 or 9 determining the extent of β-sheet structure and/or aggregation of the membrane embedded peptide molecules before and after contact with the test compound;
   ii. calculating the β-sheet aggregation or disaggregation activity of the test compound; and
   iii. obtaining the test compound with the desired activity.

15. The method of claim 14, wherein said immunogenic construct comprises at least two features selected from the group consisting of:
   a. a net negative surface potential of the liposome of at least <0mV, of at least <−10 mV, or of at least <−40 mV, in PBS;
   b. a length of the individual hydrophobic anchor molecule of at least 6 carbon atoms, at least 12 carbon atoms, at least 14 carbon atoms, or at least 18 carbon atoms;
   c. a number of hydrophobic moieties covalently bound to the N-terminus and the C-terminus of the peptide molecule and to the C-terminus and N-terminus, respectively, of 3:0; 4:0; or
   d. presence of one or more compounds which are capable of stabilising the formation of β-sheet aggregates; and
   e. absence of metal ions due to the presence of a metal chelating agent.

16. The method of claim 14, wherein said
   a. Aβ peptide is an $A\beta_{1-30}$; an $A\beta_{1-20}$; an $A\beta_{1-16}$; an $A\beta_{1-15}$; an $A\beta_{1-9}$; or any other Aβ fragment and/or truncated Aβ fragment longer than 5 amino acids; and
   b. said tau protein has an amino acid sequence identity to
      i. SEQ ID NO: 2 of at least 95%, and has substantially the same immunogenic activity as said antigenic peptide of SEQ ID NO: 2, wherein the amino acid residue corresponding to amino acid residue 18 ($P\text{-}Tyr_{18}$) of SEQ ID NO: 2 is phosphorylated;
      ii. SEQ ID NO: 3 of at least 95%, and has substantially the same immunogenic activity as said antigenic peptide of SEQ ID NO: 3, wherein at least one, or at least 2 of amino acid residues corresponding to amino acid residues 212 ($P\text{-}Thr_{212}$) and 214 ($P\text{-}Ser_{214}$) of SEQ ID NO: 3 are phosphorylated;
      iii. SEQ ID NO: 4 of at least 95%, and has substantially the same immunogenic activity as said antigenic peptide of SEQ ID NO: 4, wherein at least one, or at least 2 of amino acid residues corresponding to amino acid residues 202 ($P\text{-}Ser_{202}$) and 205 ($P\text{-}Thr_{205}$) of SEQ ID NO: 4 are phosphorylated;
      iv. SEQ ID NO: 5 of at least 95%, and has substantially the same immunogenic activity as said antigenic peptide of SEQ ID NO: 5, wherein at least one, or all of amino acid residues corresponding to amino acid residues 396 ($P\text{-}Ser_{396}$) and 404 ($P\text{-}Ser_{404}$) of SEQ ID NO: 5 are phosphorylated;
      v. SEQ ID NO: 6 of at least 95%, and has substantially the same immunogenic activity as said antigenic peptide of SEQ ID NO: 6, wherein at least one, or all of amino acid residues corresponding to amino acid residues 404 ($P\text{-}Ser_{404}$) and 409 ($P\text{-}Ser_{409}$) of SEQ ID NO: 6 are phosphorylated; or
      vi. SEQ ID NO: 7 of at least 95%, and has substantially the same immunogenic activity as said antigenic peptide of SEQ ID NO: 7, wherein at least one, at least 2, a least 3, or all of amino acid residues corresponding to amino acid residues 202 ($P\text{-}Ser_{202}$), 205 ($P\text{-}Thr_{205}$), 212 ($P\text{-}Thr_{212}$), and 214 ($P\text{-}Ser_{214}$) of SEQ ID NO: 7 are phosphorylated.

17. The immunogenic construct of claim 7, wherein the increased extent of β-sheet structure and/or β-sheet aggregation is between 80-100% as compared prior to modulation.

18. The method of claim 14, wherein the increased extent of β-sheet structure and/or β-sheet aggregation in said immunogenic construct is between 80-100% as compared prior to modulation.

* * * * *